United States Patent
Grafstrom et al.

(10) Patent No.: US 10,665,323 B2
(45) Date of Patent: May 26, 2020

(54) IN VITRO TOXICOGENOMICS FOR TOXICITY PREDICTION USING PROBABILISTIC COMPONENT MODELING AND A COMPOUND-INDUCED TRANSCRIPTIONAL RESPONSE PATTERN

(71) Applicants: Roland Grafstrom, Stockholm (SE); Pekka Kohonen, Stockholm (SE); Juuso Parkkinen, Espoo (FI); Samuel Kaski, Helsinki (FI)

(72) Inventors: Roland Grafstrom, Stockholm (SE); Pekka Kohonen, Stockholm (SE); Juuso Parkkinen, Espoo (FI); Samuel Kaski, Helsinki (FI)

(*) Notice: Subject to any disclaimer, the term of this patent is extended or adjusted under 35 U.S.C. 154(b) by 522 days.

(21) Appl. No.: 15/313,493

(22) PCT Filed: May 28, 2015

(86) PCT No.: PCT/SE2015/050617
§ 371 (c)(1),
(2) Date: Nov. 22, 2016

(87) PCT Pub. No.: WO2015/183173
PCT Pub. Date: Dec. 3, 2015

(65) Prior Publication Data
US 2017/0270239 A1 Sep. 21, 2017

Related U.S. Application Data

(60) Provisional application No. 62/003,641, filed on May 28, 2014.

(51) Int. Cl.
| | | |
|---|---|---|
| *G16B 5/00* | (2019.01) | |
| *G16B 25/00* | (2019.01) | |
| *G16C 20/30* | (2019.01) | |
| *C12Q 1/6876* | (2018.01) | |
| *G16B 20/00* | (2019.01) | |
| *G16C 20/10* | (2019.01) | |
| *G16C 20/70* | (2019.01) | |

(52) U.S. Cl.
CPC ............ *G16B 5/00* (2019.02); *C12Q 1/6876* (2013.01); *G16B 25/00* (2019.02); *G16C 20/30* (2019.02); *C12Q 2600/142* (2013.01); *C12Q 2600/158* (2013.01); *G16B 20/00* (2019.02); *G16C 20/10* (2019.02); *G16C 20/70* (2019.02)

(58) Field of Classification Search
None
See application file for complete search history.

(56) References Cited

U.S. PATENT DOCUMENTS

| | | |
|---|---|---|
| 2009/0024547 A1 | 1/2009 | Lu et al. |
| 2013/0315885 A1 | 11/2013 | Narain et al. |

FOREIGN PATENT DOCUMENTS

| | | |
|---|---|---|
| EP | 2600269 A2 | 6/2013 |
| WO | WO 2003/081211 A2 | 10/2003 |
| WO | WO 2006/050124 A2 | 5/2006 |
| WO | 2006/096649 A2 | 9/2006 |
| WO | WO 2008/060620 A2 | 5/2008 |

OTHER PUBLICATIONS

Bai, J. P. F. and Abernethy, D. R., "Systems Pharmacology to Predict Drug Toxicity: Integration Across Levels of Biological Organization", *Annual Rev. Pharmacol. Toxicol.*, vol. 53; 451-473 (2013).
Bugrim, A., et al., "Early prediction of drug metabolism and toxicity: systems biology approach and modeling", *DDT*, vol. 9; No. 3; 127-135 (2004).
Caldas, J., et al., "Probabilistic retrieval and visualization of biologically relevant microarray experiments", *Bioinformatics*, vol. 25; i145-i153 (2009).
Carrella, D., et al., "Mantra 2.0: An online collaborative resource for drug mode of action and repurposing by network analysis", *Bioinformatics Advance Access*; published Feb. 20, 2014; [retrieved Apr. 10, 2014]. Retrieved from Internet URL: http://gioinformatics.oxfordjournals.org/.
Cheng, F., et al., "In vitro transcriptomic prediction of hepatotoxicity for early drug discovery", *Journal of Theoretical Biology*, vol. 290; 27-36 (2011).
Chung, F., et al., "Functional Module Connectivity Map (FMCM): A Framework for Searching Repurposed Drug Compounds for Systems Treatment of Cancer and an Application to Colorectal Adenocarcinoma", *PLOS One*, vol. 9; Issue 1; e86299; 1-18 (2014).
Covell, D. G., "Integrating Constitutive Gene Expression and Chemoactivity: Mining the NCI60 Anticancer Screen", *PLOS One*, vol. 7; Issue 10; e44631; 1-15 (2012).
Foster, W. R., et al., "A Retrospective Analysis of Toxicogenomics in the Safety Assessment of Drug Candidates", *Toxicology Pathology*, vol. 35; 621-635 (2007).
Harrill, A. H. and Rusyn, I., "Systems biology and functional genomics approaches for the identification of cellular responses to drug toxicity", *Expert Opinion Drug Metab. Toxicol.*, vol. 4; No. 11; 1379-1389 (2008).
International Preliminary Report on Patentability for International Application No. PCT/SE2015/050617, entitled: "In Vitro Toxicogenomics for Toxicity Prediction", dated Nov. 29, 2016.
International Search Report and Written Opinion for International Application No. PCT/SE2015/050617, entitled: "In Vitro Toxicogenomics for Toxicity Prediction", dated Sep. 16, 2015.
Iorio, F., et al., "Discovery of drug mode of action and drug repositioning from transcriptional responses", *PNAS*, vol. 107; No. 33; 14621-14626 (2010).

(Continued)

*Primary Examiner* — G Steven Vanni
(74) *Attorney, Agent, or Firm* — Hamilton, Brook, Smith & Reynolds, P.C.

(57) ABSTRACT

A novel method to predict toxicity and dose-dependent effects of an agent based on transcriptomic data analysis, by determining a predictive toxicogenomics space (PTGS) score. The PTGS score helps to predict and model the toxicity of compounds typically consisting of chemicals, pharmaceuticals, cosmetics and agrochemicals. The invention further comprises methods of deriving the PTGS score, as well as computer programs to calculate PTGS scores.

20 Claims, 17 Drawing Sheets

(56) References Cited

OTHER PUBLICATIONS

Iskar, M., et al., "Drug-Induced Regulation of Target Expression", *PLOS Comput. Biol.*, vol. 6; Issue 9; e1000925; 1-8 (2010).
Iskar, M., et al., "Drug discovery in the age of systems biology: the rise of computational approaches for data integration", *Current Opinion in Biotechnology*, vol. 23; 609-616 (2012).
Iskar, M., et al., "Characterization of drug-induced transcriptional modules: towards drug repositioning and functional understanding", *Molecular Systems Biology*, vol. 9; 662; 1-13 (2013).
Judson, R. S., et al., "Using pathway modules as targets for assay development in xenobiotic screening", *Molecular Biosystems*, vol. 8; 531-542 (2012).
Khan, S. A., et al., "Comprehensive data-driven analysis of the impact of chemoinformatic structure on the genome-wide biological response profiles of cancer cells to 1159 drugs", *BMC Bioinformatics*, vol. 13; No. 112; 1-15 (2012).
Lee, A. C., et al., "Data Mining the NCI60 to Predict Generalized Cytotoxicity", *J. Chem. Inf. Model.*, vol. 48; 1379-1388 (2008).
Lee, S., et al., "Building the process-drug-side effect network to discover the relationship between biological Processed and side effects", *BMC Bioinformatics*, vol. 12; Suppl. 2; s2; 1-12 (2011).
Liu, X., "Prediction of drug class and adverse side effects based on induced gene expression profiles—a feasibility study", *Degree project in bioinformations*, 38 pages (2012).
Parkkinen, J., "Probabilistic components of molecular interactions and drug responses", Aalto University publications series Doctoral Dissertations 105/2014; 1-70 (2014).
Parkkinen, J. A., et al., "Probabilistic drug connectivity mapping", *BMC Bioinformatics*, vol. 15; No. 113; 1-10 (2014).
Parkkinen, J., et al., "Probabilistic Toxicogenomics Studies in Vitro", *Toxicology Letters*; 211S; S43-S216; Abstract P32-03; Abstract (2012).
Shedden, K., et al., "Gene expression associations with the growth inhibitory effects of small molecules on live cells: specificity of effects and uniformity of mechanisms", *Stat. Anal. Data Min.*, vol. 2; No. 3; 175-185 (2009).
Silberberg, Y., et al., "Large-Scale Elucidation of Drug Response Pathways in Humans", *Journal of Computational Biology*, vol. 19; No. 2; 163-174 (2012).
Smalley, J. L., et al., "Application of connectivity mapping in predictive toxicology based on gene-expression similarity", *Toxicology*, vol. 268; 143-146 (2010).
Smith, S. C., et al., "The COXEN Principle: Translating signatures of in vitro chemosensitivity into tools for clinical outcome prediction and drug discovery in cancer", *Cancer Research*, vol. 70; No. 5; 1753-1758 (2010).
Suter, L., et al., "Toxicogenomics in Predictive Toxicology in Drug Development", *Chemistry & Biology*, vol. 11; 161-171 (2004).
Thomas, R. S., et al., "Identification of toxicologically predictive gene sets using cDNA microarrays", *Molecular Pharmacology*, vol. 60; No. 6; 1189-1194 (2001).
Thomas, R. S., et al., "Use of Short-term Transcriptional Profiles to Assess the Long-term Cancer-Related Safety of Environmental and Industrial Chemicals", *Toxicological Sciences*, vol. 112; No. 2; 311-321 (2009).
Wang, H., et al., "Finding Complex Biological Relationships in Recent PubMed Articles Using Bio-LDA", *PLOS One*, vol. 6; No. 3; e17243; 1-14 (2011).
Wang, V., et al., "GeneTopics—interpretation of gene sets via literature-driven topic models", *BMC Systems Biology*, vol. 7; Suppl. 5; s10; 1-13 (2013).
Waters, M. D. and Fostel, J. M., "Toxicogenomics and Systems Toxicology: Aims and Prospects", *Nature Reviews*, vol. 5; 936-948 (2004).
Xing, L., et al., "LTMap: a web server for assessing the potential liver toxicity by genome-wide transcriptional expression data", *Journal of Applied Toxicology*, vol. 34; 805-809 (2014).
Zhang, J. D., et al., "Data mining reveals a network of early-response genes as a consensus signature of drug-induced in vitro and in vivo toxicity", *The Pharmacogenomics Journal*, vol. 14; 208-216 (2014).
Supplementary European search report and opinion for EP application EP 15798811.4, dated May 15, 2018.
Response to an invitation to amend the claims prior to the supplementary European search report filed with the EP Patent Office, dated May 25, 2017.
Response to the supplementary European search report and opinion filed with the EP Patent Office, dated Nov. 26, 2018.
Bisgin H. et al: "A systems approach for analysis of high content screening assay data with topic modeling", BMC Bioinformatics, Biomed Central, London, GB, vol. 14, No. Suppl 14, Oct. 9, 2013 (Oct. 9, 2013), p. S11, XP021163004, ISSN: 1471-2105, DOI:10.1186/1471-2105-14-S14-S11.
Yang Y. et al: "Toxicogenomics in drug discovery: from preclinical studies to clinical trials", Chemico-Biological Interactions, Elsevier Science Irland, IR, vol. 150, No. 1, Nov. 1, 2004 (Nov. 1, 2004), pp. 71-85, XP004619546, ISSN: 0009-2797, DOI:10.1016/J.CBI.2004.09.013.
Lin R. et al: "Gene set enrichment analysis for non-monotone association and multiple experimental categories", BMC Bioinformatics, Biomed Central, London, GB, vol. 9, No. 1, Nov. 14, 2008 (Nov. 14, 2008), p. 481, XP021047500, ISSN: 1471-2105, DOI: 10.1186/1471-2105-9-481.
Aardema M. J. et al: "Toxicology and genetic toxicology in the new era of toxicogenomics: Impact of -omics technologies", Mutation Research, Elsevier, Amsterdam, NL, vol. 499, No. 1, Jan. 29, 2002 (Jan. 29, 2002), pp. 13-25, XP002471693, ISSN: 0027-5107, DOI: 10.1016/S0027-5107(01)00292-5.
Amir-Aslani A. et al: "Toxicogenomic predictive modeling: Emerging opportunities for more efficient drug discovery and development", Technological Forecasting and Social Change, Elsevier, New York, NY, US, vol. 75, No. 7, Sep. 1, 2008 (Sep. 1, 2008), pp. 905-932, XP023980584, ISSN: 0040-1625, DOI: 10.1016/J.TECHFORE.2007.10.002.
Glez-Pena D. et al: "WhichGenes: a web-based tool for gathering, building, storing and exporting gene sets with application in gene set enrichment analysis", Nucleic Acids Research, vol. 37, No. Web Server, Apr. 30, 2009 (Apr. 30, 2009), pp. W329-W334, XP055471133, ISSN: 0305-1048, DOI: 10.1093/nar/gkp263.
Mattingly C. J. et al: "The Comparative Toxicogenomics Database: A Cross-Species Resource for Building Chemical-Gene Interaction Networks", Toxicological Sciences, vol. 92, No. 2, May 4, 2006 (May 4, 2006), pp. 587-595, XP055471140, ISSN: 1096-6080, DOI: 10.1093/toxsci/kfl008.
Ebbels T. M. D. et al: "Prediction and Classification of Drug Toxicity Using Probabilistic Modeling of Temporal Metabolic Data: The Consortium on Metabonomic Toxicology Screening Approach", Journal of Pr0te0me Research., vol. 6, No. 11, Oct. 4, 2007 (Oct. 4, 2007), pp. 4407-4422, XP055471088, US ISSN: 1535-3893, DOI: 10.1021/pr0703021.

IN VITRO TOXICOGENOMICS FOR TOXICITY PREDICTION USING PROBABILISTIC COMPONENT MODELING AND A COMPOUND-INDUCED TRANSCRIPTIONAL RESPONSE PATTERN

This application is the U.S. National Stage of International Application No. PCT/SE2015/050617, filed May 28, 2015, which designates the U.S., published in English, and claims the benefit of U.S. Provisional Application No. 62/003,641, filed May 28, 2014.

BACKGROUND OF THE INVENTION

Field of the Invention

The present invention relates generally to predicting toxicity of compounds or agents Description of the Prior Art The societally much needed ability to predict human toxicity of chemical compounds would be helped by defining the complete, or core, set of genomic changes that could causally explain why the dose generally makes a chemical into a poison at the cellular and organismal levels. However chemical risk assessment currently proceeds without taking into account this information. A clear problem in the interpretation of the mass of data generated by genome-wide profiling technologies is both that some results cannot be mechanistically interpreted, but also that too many potential inferences can be made and the inferences therefore are not sufficiently specific or predictive.

In 2012, the Organization for Economic Co-operation and Development (OECD) launched a new program on the development of Adverse Outcome Pathways. An Adverse Outcome Pathway (AOP) is an analytical construct that describes a sequential chain of causally linked events at different levels of biological organization that lead to an adverse health or ecotoxicological effect. AOPs are the central element of a toxicological knowledge framework being built to support chemical risk assessment based on mechanistic reasoning. AOPs include chemical mode-of-action (MoA) and toxicity pathway activities that can be inferred from chemical perturbations gene expression data if it is known which gene activities contribute to them. Furthermore toxicity is predicted from the Thresholds of Toxicological Concern (TTC) concept, namely establishment of a generic exposure level for (groups of) chemicals below which there is expected to be no appreciable risk to human health. The current concept of TTC is relatively loose and relies on structure-based read-across, as well as on structural alerts for toxicity, including carcinogenicity.

Availability of large human omic's data sets (a general term for a broad discipline of science and engineering for analyzing the interactions of biological information objects in various 'omes such as genome or metabolome) enables data-driven modeling and model-driven data analysis of toxicity leading to Big Data analytics (a collection of data sets so large and complex that it becomes difficult to process using traditional database management).

There is a need for an efficient tool that can be used to predict the toxicity of an agent, such as within the chemicals, pharmaceuticals, cosmetics or agrochemicals industries.

SUMMARY OF THE INVENTION

The use of the present invention, which will be described subsequently in greater detail, is to provide new and efficient aid to predict and model the toxicity of compounds and agents typically considered by chemicals, pharmaceuticals, cosmetics and agrochemicals industries. This is done in the invention herein by a method of determining a Predictive Toxicogenomics Space (PTGS) score for an agent. To derive the PTGS score, probabilistic component modeling is used to identify specific components that are activated when a cell becomes intoxicated, meaning that the tested compound is toxic. Other aspects of the invention provides a method of generating PTGS prediction models using probabilistic components modeling from databases of compound and gene expression data, as well as computer programs for generating a PTGS score and hence predicting toxicity of a test agent.

An aspect of the embodiments relates to a method of defining a PTGS score indicative of a toxicity prediction for an agent. The method comprises transforming gene data defining, for each instance of a plurality of instances, differential gene expression of genes in a test biological sample induced by a test agent into gene set data defining, for each instance of the plurality of instances, an activation value for each gene set of a plurality of gene sets. An instance defines a unique pair of a test agent and a test biological sample. A gene set represents a collection of similar individual genes. The method also comprises performing a probabilistic component modeling on the gene set data to define multiple components representing a respective specific component-induced transcriptional response pattern active for a subset of test compounds and test cell lines. The multiple, i.e. at least two, components encapsulate the genes of the plurality of gene sets. The method further comprises determining, for a portion of the test agents, a concentration-dependent toxicity reflective of whether a concentration of a test agent applied to a test biological sample to induce a differential gene expression in the test biological sample is above, equal to or below a defined toxicity level. The method additionally comprises identifying, based on the concentration-dependent toxicities, multiple prediction components as a subset of the multiple components and being predictive of toxicity. The PTGS score is then defined as a proportion of differential gene expression, induced by an agent, that belongs to the multiple prediction components.

Another aspect of the embodiments defines a method of predicting toxicity of an agent. The method comprises obtaining gene expression data defining differential gene expression of genes in a biological sample induced by the agent. The method also comprises calculating, based on the gene expression data, a PTGS score indicative of a toxicity prediction for the agent. The PTGS score represents a portion of the differential gene expression in the biological sample, induced by the agent, that belongs to multiple prediction components. These multiple prediction components are identified using the following steps. 1) Transforming gene data defining, for each instance of a plurality of instances, differential gene expression of genes in a test biological sample induced by a test agent into gene set data defining, for each instance of the plurality of instances, an activation value for each gene set of a plurality of gene sets. An instance defines a unique pair of a test agent and a test biological sample, a gene set represents a collection of similar individual genes. 2) Performing a probabilistic component modeling on the gene set data to define multiple components representing a respective specific compound-induced transcriptional response pattern active for a subset of test compounds and test cell lines. The multiple components encapsulate the genes of the plurality of gene sets. 3) Determining, for a portion of the test agents, a concentration-dependent toxicity reflective of whether a concentration of a test agent applied to a test biological sample to induce a differential expression of genes in the test biological sample is above, equal to or below a defined toxicity level. 4) Identifying, based on the concentration-dependent toxicities, the multiple prediction components as a subset of the multiple components and being predictive of toxicity.

A further aspect of the embodiments relates to a method of predicting toxicity of an agent. The method comprises obtaining gene expression data defining differential gene expression of toxicity representing genes in a biological sample induced by the agent. The toxicity representing genes are identified by the following steps. 1) Transforming gene data defining, for each instance of a plurality of instances, differential gene expression of genes in a test biological sample induced by a test agent into gene set data defining, for each instance of said plurality of instances, an activation value for each gene set of a plurality of gene sets. An instance defines a unique pair of a test agent and a test biological sample, a gene set represents a collection of similar individual genes. 2) Performing a probabilistic component modeling on the gene set data to define multiple components representing a respective specific compound-induced transcriptional response pattern active for a subset of test compounds and test cell lines. The multiple components encapsulate the genes of the plurality of gene sets. 3) Determining, for a portion of said test agents, a concentration-dependent toxicity reflective of whether a concentration of a test agent applied to a test biological sample to induce a differential expression of genes in the test biological sample is above, equal to or below a defined toxicity level. 4) Identifying, based on the concentration-dependent toxicities, the multiple prediction components as a subset of the multiple components and being predictive of toxicity. 5) Identifying the toxicity representing genes as genes belonging to the multiple prediction components. The method also comprises predicting toxicity of the agent based on a percentage of the toxicity representing genes that are significantly differentially expressed in the biological sample as induced by the agent.

Yet another aspect of the embodiments relates to a method of predicting toxicity of an agent. The method comprises obtaining gene expression data defining differential gene expression of toxicity representing genes or at least a defined portion of the toxicity representing genes in a biological sample induced by the agent. The toxicity representing genes comprises the genes RELB, HBEGF, CCNL1, TNFAIP6, NFKBIE, REL, ARIH1, SOS1, NFKB2, TIPARP, PPP1R15A, BIRC3, FAM48A, TNFAIP3, NR4A2, THUMPD2, CNOT2, CLK4, DUSP1, KLF10, DLX2, EFNA1, NUPL1, POU2F1, NFYA, PSPC1, ZNF263, CLK1, BTG1, TSC22D1, BCL7B, FBXO9, STX3, WEE1, PPM1A, MAFG, SLC38A2, KLF6, ZNF292, IRS2, RBM15, HSF2, DUSP4, BCL6, MKLN1, CYR61, ZNF435, STK17B, AMD1, ZNF281, ZNF239, NEU1, HEXIM1, UBE2H, PRKRIP1, ZNF23, CD55, TAF5, RBM5, FSTL3, JUND, PITX2, IER5, ZBTB5, CARS, IER2, RABGGTB, STAT3, SIP1, AKAP10, MAP1LC3B, WDR67, NCOA3, ZFP161, BAG3, LRP8, BCL10, FNBP4, PNRC1, PPAT, CETN3, DMTF1, UBE2M, RYBP, YTHDC1, PDGFA, ATP2B1, TIA1, RGS3, PRNP, KLF5, CHKA, TMCC1, EPHA2, ELF1, ELF4, THUMPD1, MAFF, ZNF14, SRF, EPAS1, CLK3, ARID5B, KLHL9, POLD3, CENPA, SLC25A12, PTPN3, NPAT, BTAF1, MTMR4, SERPINH1, MCM7, RFC4, HSPA4L, DNAJA1, MCM3, RLF, FBXL5, MTF2, POGZ, BTN2A1, BRD1, FEM1C, BAZ2B, RANBP6, COIL, BACH1, ZNF3, RBM4B, ZNF45, ARID4B, ARHGEF7, CSTF1, CENPC1, NCK1, NFIL3, RPP38, CHD9, ZNF180, ZNF588, ZNF131, CDC42EP2, RNF113A, TLK2, ZNF44, RIC8B, KBTBD2, BAG5, RBM39, ZBTB24, NEDD9, STARD13, SCYL3, ZNF432, SEC31A, INTS6, JMJD1C, TCF21, FOXJ3, NUP153, ZNF217, KIF2A, ZNF195 RIPK2, GTF2E1, ZNF451, PGS1, MYC, NGDN, PNRC2, PRPF3, CRKL, ADNP, MORC3, POLS, ZCCHC8, ZNF274, ZCCHC6, EGR1, JUN, FOS, DDIT3, PMAIP1, NFKBIA, GADD45A, NR4A1, GEM, FOSL1, SLC3A2, EIF1AX, KLF2, GINS2, FHL2, FOSB, RPA1, EZH2, MCM5, RFC3. The defined portion of the toxicity representing genes comprises at least 50% of the toxicity representing genes, preferably at least 75% of the toxicity representing genes, more preferably at least 80%, or at least 85%, or at least 90% or at least 95% of the toxicity representing genes. The method also comprises predicting toxicity of the agent based on a percentage of the toxicity representing genes that are significantly differentially expressed in the biological sample as induced by the agent.

A further aspect of the embodiments relates to a method of predicting toxicity of an agent. The method comprises obtaining gene expression data defining differential gene expression of toxicity representing genes in a biological sample induced by the agent. The toxicity representing genes comprise at least one gene regulated by each transcription factor selected from the group consisting of TP53, EP300, CDKN2A, PPARG, HIF1A, RELA, RB1, NR3C1, NFKBIA, ESR1, STAT5A, JUN, STAT3, SP1, SMARCA4, SMAD7, RARB, MYC, JUNB, EGR1, E2F1, CTNNB1, BRCA1, ATF2, RBL1, NFKB1, FOS, E2F3, CREBBO, SRF, NCOR2, HTT, ELK1, CYLD, and CREM. The method also comprises predicting toxicity of the agent based on a percentage of the toxicity representing genes that are significantly differentially expressed in the biological sample as induced by the agent.

Further aspects of the embodiments define computer programs comprising instructions, which when executed by a processor, cause the processor to execute or perform operations or steps of the above described methods.

A related aspect of the embodiments defines a carrier comprising a computer program as defined above. The carrier is one of an electronic signal, an optical signal, an electromagnetic signal, a magnetic signal, an electric signal, a radio signal, a microwave signal, or a computer-readable storage medium.

BRIEF DESCRIPTION OF THE DRAWINGS

The embodiments, together with further objects and advantages thereof, may best be understood by making reference to the following description taken together with the accompanying drawings, in which:

FIG. 5. The proportion of the transcriptional variance explained by the PTGS components increases with dose and predicts toxicity above the GI50-level. (a,b) The number of differentially expressed genes (y-axis) relative to concentration-dependent toxicity (x-axis) for the 492 CMap instances. Shade and size in (b) indicate the proportion of the transcriptional variance explained by the PTGS components, i.e. the PTGS score. Concentration-dependent toxicity was defined as the difference of the logarithmic CMap concentration and GI50 values. (c,d) All instances with few differentially expressed genes that are measured at higher than GI50 have toxicity below the TGI concentration (oval). (e) Relatively few of the chemicals have been profiled at concentrations that result in overt cell killing, i.e. with higher than LC50 concentrations (circle).

FIG. 6. PTGS-component derived approach predicts dose-dependent toxicity—chemicals with PTGS score>0.12 are classified as potentially toxic (>50% probability of toxicity above the GI50 level) (a) PTGS scores (y-axis) relative to concentration-dependent toxicity (x-axis) serves to indicate how gene expression profiles couple to toxicity. Dashed vertical line indicates a cut-off for concentration-dependent toxicity at the level of GI50. (b) The proportion of CMap instances (x-axis) with PTGS score higher than the cut-off set at the GI50-level (y-axis) is used to set a threshold for considering an instance being "toxic". Horizontal dashed lines in both figures indicate a PTGS score cut-off at 0.12, set to a level where 50% of CMap instances are above the GI50-level of growth inhibition.

FIG. 7. Dose-response relationships of selected PTGS components. (a) Components A-C become primarily activated beyond TGI levels of toxicity, including some in instances measured at cell killing doses above the LC50 level (circle). (b) The components D, F and J are active at or around the TGI-level (circle). (c) Components E, K and M are active above the GI50 level but below TGI (ellipse). Together the PTGS components span a wide range of dose-responses beyond the GI50 level.

FIG. 8. Validation of PTGS-component derived prediction relative quantitative structure activity relationships (QSAR). Totally 38 non-NCI 60-selected CMap compounds were chosen for high-throughput screening-based validation applying the three CMap cell lines. Loss of survival was assessed at log concentration intervals (from $10^{-8}$ to $10^{-4}$) using the ATP assay (as surrogate for decreases in cell number and growth inhibition). PTGS scores were calculated from CMap data. ROC curves indicate the toxicity-predictive performance of a set of non-NCI-60 CMap instances using the PTGS components relative predictions made by Partial Least Squares QSAR. The areas under the ROC curve (AUC) values for PTGS (AUC=0.92) versus QSAR (AUC=0.64) show that PTGS score outperforms the QSAR approach.

FIG. 9. Combined PTGS-component derived and PTGS-associated gene-based workflow for compound safety assessments. Results 1-3 from the three analysis streams are combined to estimate compound virtual GI50, mode of action, NOEL/LOEL and BMD/BMDL. An extended of this workflow is unified into a customer service concept in FIG. 17 to constitute a PTGS-AOP conceptual framework.

Figure 17:
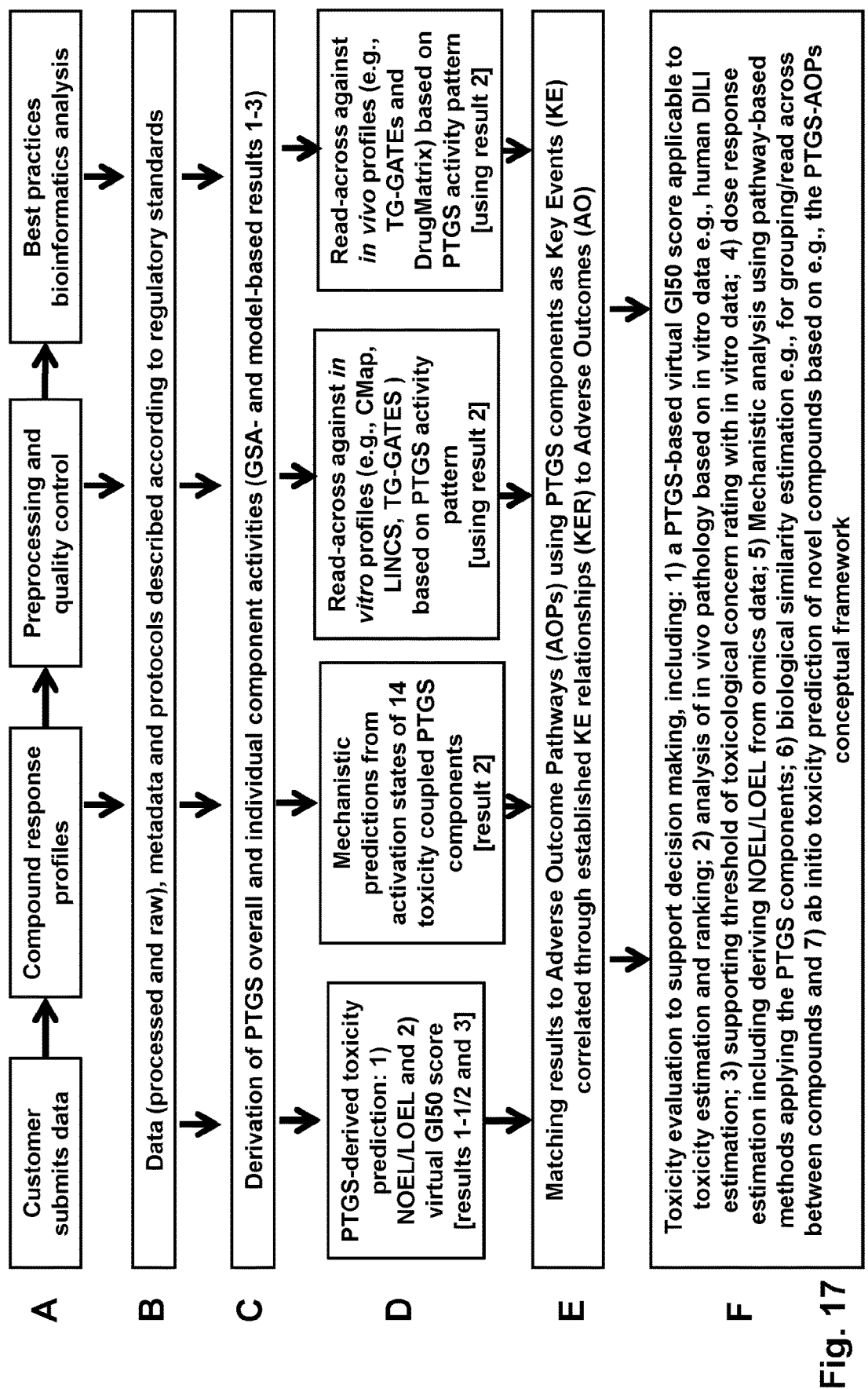

FIG. 17. Applying the PTGS concept in a contract service for predicting safety of customer compounds from omics profiles enables utilization of the PTGS-AOP conceptual framework for chemical safety evaluation and for the prediction of Drug Induced Liver Injury (DILI) potential.

DETAILED DESCRIPTION OF THE INVENTION AND PREFERRED EMBODIMENTS THEREOF

The present embodiments generally relate to predicting toxicity of a compound or agent. In particular, the present embodiments involves predicting toxicity of an agent based on the effect the agent has on gene expression in a biological sample, such as in a cell, cell line or tissue sample. In particular embodiments as disclosed herein probabilistic component models are used as a tool in analysing gene expression data in order to identify and interpret coherent components from the gene expression data. Accordingly, such probabilistic component models are applied to detect coherent drug response patterns from gene expression data. The identified test agent response components are associated to toxicological outcomes in order to provide a comprehensive view of molecular toxicogenomics responses.

Embodiments as disclosed herein thereby predict toxicity of an agent based on a predictive toxicogenomics space (PTGS) score or based on toxicity representing genes as identified using the probabilistic component models.

Definitions and Technical Manual:

The terms "agent" and "test agent" as used herein refers to an agent, compound or composition that is being tested or analyzed in a method of the invention. For instance, an agent may be a pharmaceutical candidate drug for which toxicology data is desired. The term "agent vehicle" refers to the diluent or carrier in which the agent is dissolved, suspended in or administered in, to an animal, organism or cells or other type of biological sample. Test agent refers to an agent for which gene expression data is available and used as disclosed herein to define and derive a tool, method or model, which are then used to predict toxicity of various agents.

The term "gene" as used herein, includes fully characterized open reading frames and the encoded mRNA as well as fragments of expressed RNA that are detectable by any hybridization method in the cell or tissue samples assayed as described herein. For instance, a "gene" includes any species of nucleic acid that is detectable by hybridization to a probe in a microarray, such as the "genes" associated with the PTGS. As used herein, at least one gene includes a "plurality of genes".

The term as used herein, "differential expression value" refers to a numerical representation of the expression level of a gene, genes or gene fragments between experimental paradigms, such as a test or treated biological sample, compared to any standard or control. For instance, a differential expression value may be presented as microarray-derived florescence or probe intensities for a gene or genes from a test biological sample compared to a control, such as an unexposed biological sample or a vehicle-exposed cell or tissue sample. The differential expression value may be in the form of a fold change value, signed or non-signed t-statistics, p-value or any other way of quantifying differential expression change of a gene, genes or gene fragments in a directional (up or down) or non-directional manner.

The term as used herein, a "gene expression profile" comprises any quantitative representation of the expression of at least one mRNA species in a biological sample or population and includes profiles made by various methods such as differential display, PCR, microarray, RNA-seq and other hybridization analysis, etc.

The term as used herein, "nucleic acid hybridization data" refers to any data derived from the hybridization of a sample of nucleic acids to a one or more of a series of reference nucleic acids. Such reference nucleic acids may be in the form of probes on a microarray or set of beads or may be in the form of primers that are used in polymerization reactions, such as PCR amplification, to detect hybridization of the primers to the sample nucleic acids. Nucleic hybridization data may be in the form of numerical representations of the hybridization and may be derived from quantitative, semi-quantitative or non-quantitative analysis techniques or technology platforms. Nucleic acid hybridization data includes, but is not limited to gene expression data. The data may be in any form, including florescence data or measurements of florescence probe intensities from a microarray or other hybridization technology platform. The nucleic acid hybridization data may be raw data or may be normalized to correct for, or take into account, background or raw noise values, including background generated by microarray high/low intensity spots, scratches, high regional or overall background and raw noise generated by scanner electrical noise and sample quality fluctuation.

The term as used herein "probabilistic component modeling" means a method used in this invention to define a set of gene expression response components. Briefly, probabilistic decomposition is exemplified in this invention using Latent Dirichlet allocation (LDA) Component Model (topic modeling), where the Component Model assumes that each instance i has a probabilistic assignment vector $p(z|i)$ to components z, and each component has a probabilistic assignment vector $p(z|gs)$ to a gene sets gs. Thus, each instance and gene set can be associated with multiple components following the polypharmacology assumption. Each component then represents a specific chemical-induced transcriptional response pattern, active for a subset of chemicals and cell lines. The components can be interpreted as biological processes through the gene set activities, and the assumption is that some of these capture the toxicity-associated responses. Other examples of probabilistic component models in addition to LDA include elastic net regression, non-linear regression, Group Factor Analysis (GFA), tensor-derived GFA, etc.

PTGS as used herein means Predictive Toxicogenomics Space (PTGS). A PTGS score means a numerical score generated from a toxicity model of this invention and that can be used as a cut-off score to predict at least one toxic effect of an agent. In various embodiments, the threshold for the PTGS score is set at a concentration value inducing a measurable effect on cell growth or viability. The concentration value could, for instance, represent 50% growth inhibition (GI50), total growth inhibition (TGI) or lethal concentration 50% (LC50). The PTGS score is, in an embodiment, calculated as the sum of the activities over the components of this invention (calculated by normalizing the sum of all component probabilities to 1 and then summing up the probabilities of the 14 components (A-N), where the PTGS cut-off score is 0.12 (a PTGS score of 0.2 means that 20% of the differential gene expression can be attributed to the components)). PTGS-associated genes or PTGS_core as used interchangeably herein means a list of 199 genes which are strongly associated with the PTGS in general, but not with a particular component. PTGS-component derived genes or PTGS_ALL as used interchangeably herein means a list of 1331 genes which are associated with the PTGS components (A-N).

AOP as used herein means Adverse Outcome Pathways and describes a sequential chain of causally linked events at different levels of biological organization that lead to an adverse health or ecotoxicological effect, as described by Vinken (Vinken, M 2013). TTC as used herein means Thresholds of Toxicological Concern and a generic exposure level for (groups of) chemicals below which there is expected to be no appreciable risk to human health, as described by Munro et al (Munro I C et al 2008). Virtual GI50 as used herein means a predicted toxicity value determined from gene expression profile data analysis, related to the probability of exceeding the GI50 level of cytotoxicity.

CMap, the US Broad Institute Connectivity Map (http://www.broadinstitute.org/cmap/) means Causal Mapping of a dataset of thousands of gene expression profiles of drugs, mostly FDA approved drugs, and has been used to define biologically similar chemicals for drug repurposing and to define a chemical's modes of action. CMap content include 7056 HG-U133A series of Affymetrix GeneChip® expression profiles (11948 genes based on Ensembl hg19); 1309 compounds; 6100 individual instances (i.e., one treatment and vehicle pair); 3587 compound-cell line pairs; 5 cell lines: MCF7 (3095), PC3 (1741), HL-60 (1229), SKMEL5 (17), ssMCF7 (18). Most compounds were tested at a concentration of 10 µM with a perturbation time of 6 hours.

LDA, Latent Dirichlet Allocation means a model (component model) previously described by Blei et al (Blei D M et al 2003) used for probabilistic decomposition in this invention to identify transcriptional response patterns from the gene set activation count data.

GSEA, Gene Set Enrichment Analysis means a method previously described by Subramainian et al used to reduce high dimensionality of data and incorporate prior knowledge, using 1321 curated gene sets from the Molecular Signature Database (MSigDB) (Subramainian et al 2005). Multiple possible GSEA methods exist and that can be classified as seen below (Nam & Kim 2008). Self-contained gene set testing, GSEA that tests the self-contained null hypothesis: The genes in the gene set do not have any association with the subject condition, i.e. no gene in the set is differentially expressed. This method does not care about what the genes outside the set do. (Nam & Kim 2008, Ritchie et al. 2015). Examples include R/Bioconductor limma MROAST function (Ritchie et al. 2015). Competitive gene set testing (most commonly employed GSEA method), GSEA that tests the competitive null hypothesis: The genes in the gene set do not have stronger association with the subject condition than the other genes (Goeman & Buhlmann 2007, Nam & Kim 2008). Examples include R Bioconductor limma ROMER and CAMERA functions (Ritchie et al. 2015). Broad Institute GSEA tool employs a mixture approach combining self-contained and competitive testing but is more closely classified as competitive (Nam & Kim 2008, Subramanian et al. 2005). Single sample gene set testing, that can perform GSEA profile estimations using a single instance, instead of using and summarizing a set of treatment/control instances and their biological replicates. Examples include the R/bioconductor Gene Set Variation Analysis (GSVA) tool (implements several methods, including the GSVA signature method) (Hänzelmann et al. 2013) and the Broad Institute "GseaPreranked analysis", also a pure competitive GSEA method (Subramanian et al. 2005) used in this invention to derive the PTGS. Gene set testing accounting for potential errors arising inter-gene correlations, GSEA that account for inter-gene correlation in the sense defined by literature (Ritchie et al. 2015). Positive examples include R/Biooconductor limma CAMERA, ROMER, MROAST methods and the Broad Institute GSEA tool when used with biological replicates and sample-level permutations (Subramanian et al. 2005). Negative examples include R/Bioconductor limma geneSetTest or wilcoxGST methods that perform simple gene-level permutations. Absolute gene set testing. GSEA which uses absolute values of a test statistic instead the signed (e.g., fold-change) values: incorporating the absolute gene statistic in gene-sampling gene-set analysis substantially reduces the false-positive rate and improves the overall discriminatory ability, especially for single sample GSEA e.g., GSVA (Nam 2015). This invention used absolute gene set testing for all variants of the PTGS-associated gene-based method, the preferred aspect of the former method. Most gene set testing methods can be run in either absolute or directional mode.

Figure 14:
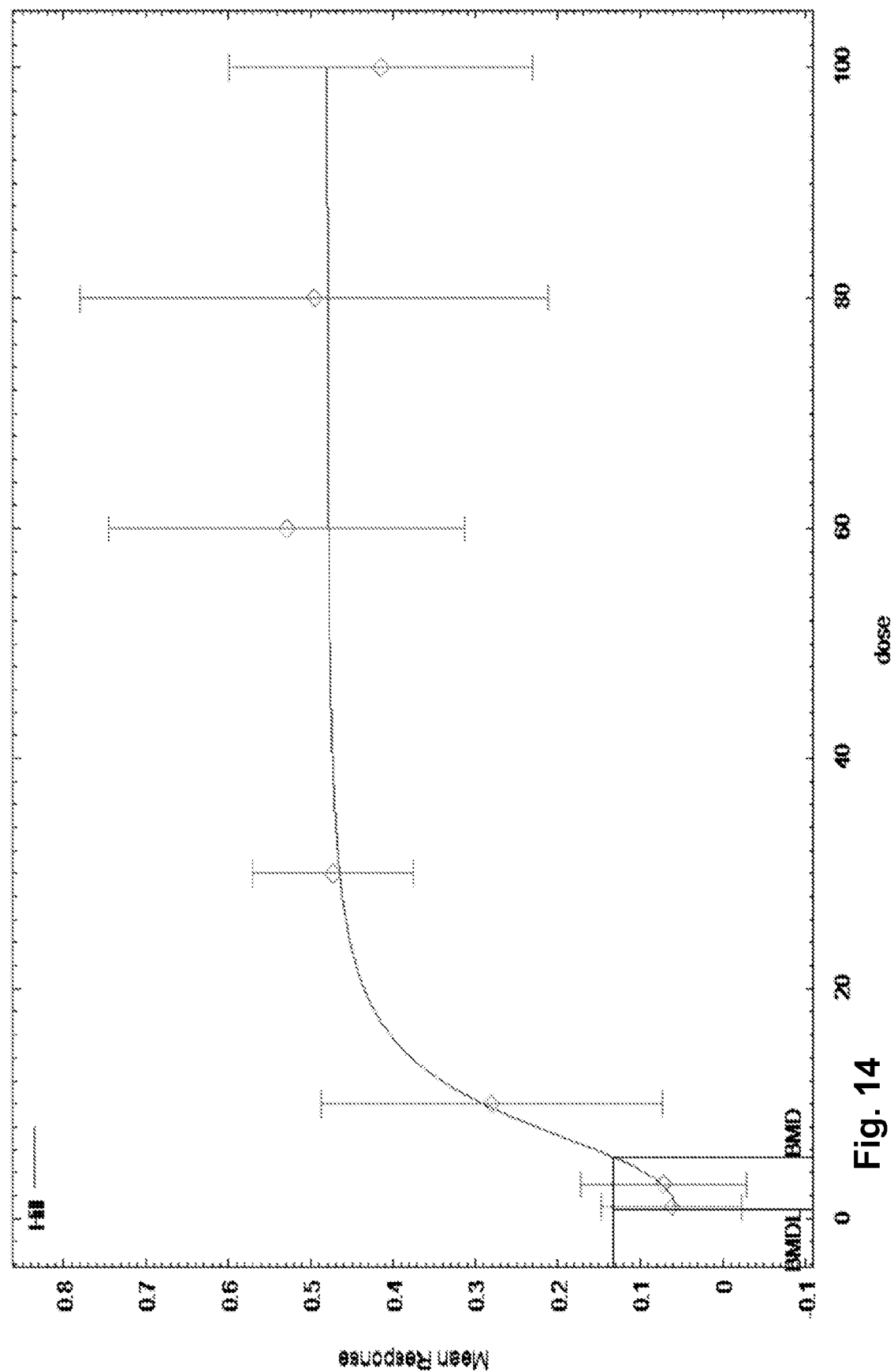
FIG. 14. Benchmark dose calculations using the PTGS-associated gene-based approach. BMD (at 0.95 confidence level) was 5.37 µM and BMDL 0.77 µM. BMDL: A dose or concentration that produces a predetermined change in response rate of an adverse effect compared to background (BMDL is the lower limit of a 95% C.I.) (Clewell et al. 2014).
Figure 15:
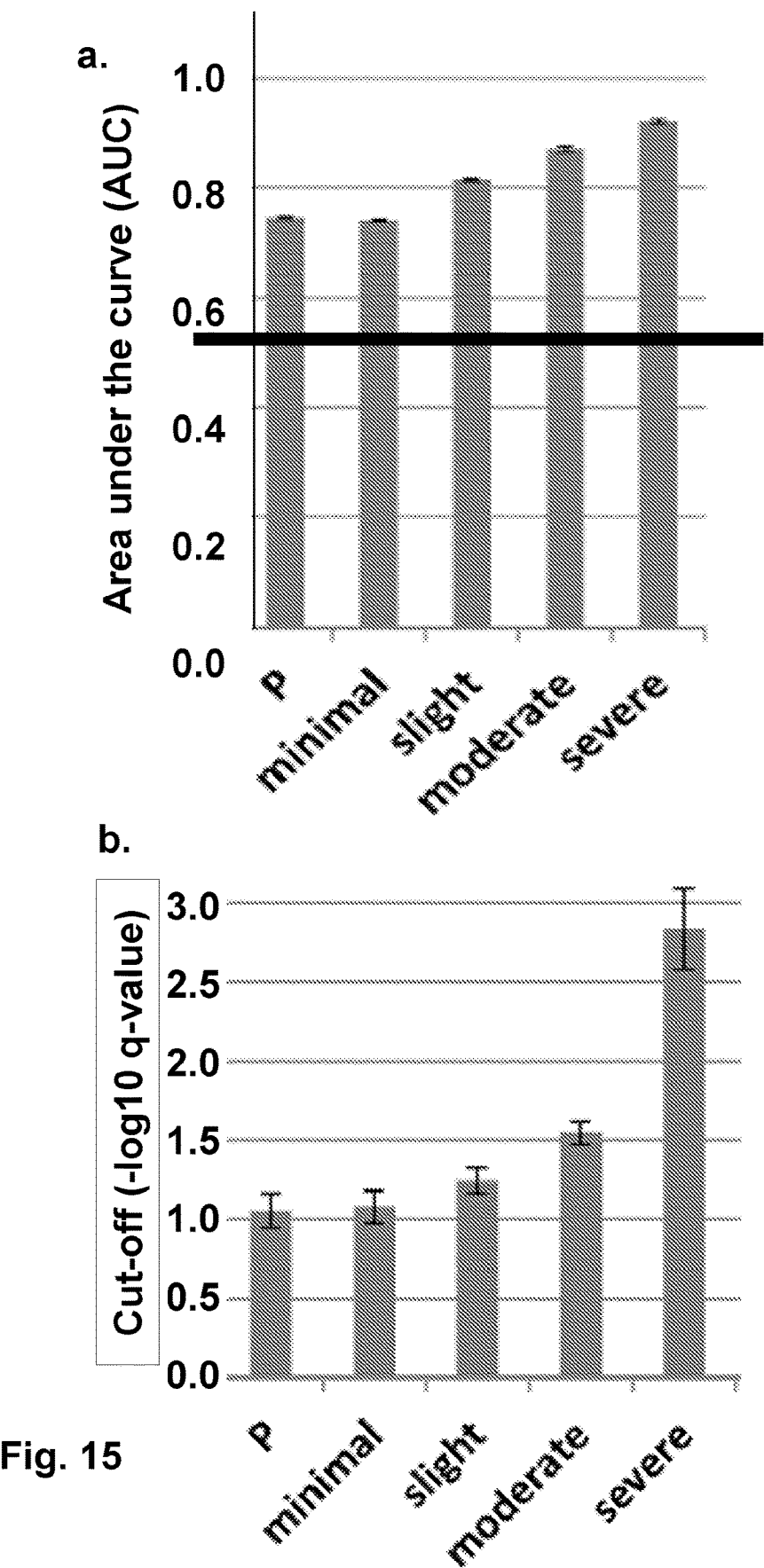
FIG. 15. Gene set analysis (GSA; MROAST) predicts the degree of severity of rat liver pathology following repeated chemical exposures. (a) Average AUC values over all PTGS components to predict the degree of severity (standard error around the mean is shown). Grades of pathological findings were statistically tested, instead of the findings themselves. (b) Decision threshold of the predictions from standard ROC curve analysis. Increasing levels of PTGS activation predict increasing severity of pathological findings.

Benchmark Dose (BMD)—a dose or concentration that produces a predetermined change in response rate of an adverse effect (called the benchmark response or BMR) compared to background (see FIG. 14). BMDL means the statistical lower confidence limit of the dose or concentration of the BMD. Benchmark response (BMR) means an adverse effect, used to define a benchmark dose from which a dose for n RfD (or RfC) can be developed. The change in response rate over background of the BMR is usually in the range of 5-10%, which is the limit of responses typically observed in well-conducted experiments in mammals, such as animals. RfD—Reference Dose (RfC—Reference Concentration) dose not expected to cause adverse health effects in humans.

Receiver operating characteristic (ROC), or ROC curve, means a graphical plot that illustrates the performance of a binary classifier system as its discrimination threshold is varied. Area Under the ROC Curve (AUC) means a statistic to measure classifier performance, commonly used in machine learning applications that encapsulates both sensitivity and specificity of the classifier performance.

Implementation Embodiments

An aspect of the embodiments relates to a method of defining a PTGS score indicative of a toxicity prediction for an agent. The method comprises transforming gene data defining, for each instance of a plurality of instances, differential gene expression of genes in a test biological sample induced by a test agent into gene set data defining, for each instance of the plurality of instances, an activation value for each gene set of a plurality of gene sets. An instance defines a unique pair of a test agent and a test biological sample. A gene set represents a collection of similar individual genes.

The method also comprises performing a probabilistic component modeling on the gene set data to define multiple components representing a respective specific component-induced transcriptional response pattern active for a subset of test compounds and test cell lines. The multiple, i.e. at least two, components encapsulate the genes of the plurality of gene sets. The method further comprises determining, for a portion of the test agents, a concentration-dependent toxicity reflective of whether a concentration of a test agent applied to a test biological sample to induce a differential gene expression in the test biological sample is above, equal to or below a defined toxicity level. The method additionally comprises identifying, based on the concentration-dependent toxicities, multiple prediction components as a subset of the multiple components and being predictive of toxicity.

The PTGS score is then defined as a proportion of differential gene expression, induced by an agent, that belongs to the multiple prediction components. The PTGS score as defined by the method described above is representative of and can thereby be used in order to predict toxicity of an agent.

The method starts with gene data defining differential gene expression of genes in at least one test cell line and where the differential gene expression is induced in the at least one test cell line by a test agent. This gene data is transformed into the gene set data. The gene set data defines an activation value for each gene set of a plurality of gene sets. This means that the gene set data represents at least one activation value for each such gene set. An activation value represents differential gene expression of a collection of similar individual genes in the gene set as induced by the test agent in the test biological sample. This means that a gene set is defined by genes for which there is evidence based on prior biological knowledge that they share a common biological function, chromosomal location, or regulation. For instance, the genes of a gene set could be involved in a same metabolic or synthesis pathway in the biological sample or share a common regulation pathway in the biological sample. This means that instead of investigating gene expression of individual genes, the transformation in the method above use differential gene expression for set of genes. This is more robust against noise and more accurately detect subtle changes in gene expression. An example of such transformation from gene data into the gene set data is to use Gene Set Enrichment Analysis (GSEA) as will be further described herein.

The transformation in the method is performed for each instance of a plurality of instances. Such an instance defines and represents a unique pair of test agent and test biological sample. In a preferred embodiment, the method involves using multiple of different test agents and/or, preferably and, multiple biological samples. For instance, if the gene data involves N test agents that have been applied to M test biological samples in order to determine the differential gene expression for each such test agent-sample pair then in total N×M instances have been tested and N×M differential gene expression profiles are available in the gene data.

Genes and proteins are typically organised into functional categories. Thus, a central task in molecular biology is to identify and analyze such functionally coherent modules. The most common gene module detection approach is clustering, where the idea is to group the genes such that similar genes are in the same groups while dissimilar genes are in different groups. The rationale is that genes with similar expression profiles that end up clustered together are typically functionally similar. A large number of methods have been developed for clustering genes, differing in how the similarity is defined and how the similarity is used for clustering. A commonly used similarity measure is Pearson correlation. Popular clustering methods include hierarchical clustering, K-means, self-organizing maps, graph-theoretic approaches, and model based methods. Biclustering is an alternative to clustering methods that operates based on the whole range of measured conditions. In biclustering, closely related to subspace clustering, subsets of genes exhibiting consistent patterns over a subset of the conditions are searched for, making the analysis local rather than global. In addition to functional similarity of genes, biclusters can be used to make hypotheses about the conditions within the cluster that exhibit consistent gene expression. For example drugs that act consistently on the set of genes can have shared mechanisms of actions through these genes.

A probabilistic component modeling is performed on the gene set data to define multiple components. Each such component represents a specific compound-induced transcriptional response pattern active for a subset of test compounds and test cell lines. Such probabilistic component modeling is applied to detect a set of robust compound-induced gene expression response components. The components can be interpreted as biological processes through the gene set activities, and the assumption is that some of these capture the toxicity-associated responses. The multiple components collectively encapsulate and encompasses the genes of the plurality of gene sets.

Concentration-dependent toxicity is then determined for a portion of the test agents. Such concentration-dependent toxicity reflects whether a concentration of a test agent applied to a test biological sample to induce a differential gene expression in the test biological sample is above, equal to or below a defined toxicity level. Thus, the concentration-dependent toxicity could be defined as defining whether the concentration of the test agent used in order to get the gene data was above, equal to or lower than the defined toxicity level. This means that if the concentration was above the toxicity level then the differential gene expression obtained in a test biological sample using the test agent is representative of a gene expression in the test biological sample using a toxic level of the test agent. Correspondingly, if concentration was below the defined toxicity level then the differential gene expression obtained in a test biological sample using the test agent is representative of a gene expression in the test biological sample using a non-toxic level of the test agent.

The determined concentration-dependent toxicities are then used in order to identify multiple prediction components among the multiple components obtained following the probabilistic component modeling. These prediction components are then identified as a subset of the multiple components and are indicative or predictive of toxicity. Thus, the concentration-dependent toxicities enable identification of those components that are most predictive of toxicity among all components. This means that in order to investigate the toxicity of an agent it is sufficient to investigate these prediction components and the genes defined by the prediction components and thereby the differential gene expression as obtained for these genes of the prediction components.

The PTGS score that is indicative of toxicity is then defined as the proportion or percentage of differential gene expression induced by an agent that belongs to the prediction components. The PTGS score can thereby assume a value between 0 and 1. Generally, the higher the value the more toxic an agent is.

The PTGS score of the embodiments can thereby be used to predict toxicity of an agent or agent. In such a case, a method of predicting toxicity of an agent comprises obtaining gene expression data defining differential gene expression of genes in a biological sample induced by the agent. The method also comprises calculating, based on the gene expression data, a PTGS score indicative of a toxicity prediction for the agent. The PTGS score represents a portion of the differential gene expression in the biological sample, induced by the agent, that belongs to multiple prediction components. These multiple prediction components are identified using the following steps.

1) Transforming gene data defining, for each instance of a plurality of instances, differential gene expression of genes in a test biological sample induced by a test agent into gene set data defining, for each instance of the plurality of instances, an activation value for each gene set of a plurality of gene sets. An instance defines a unique pair of a test agent and a test biological sample, a gene set represents a collection of similar individual genes.

2) Performing a probabilistic component modeling on the gene set data to define multiple components representing a respective specific compound-induced transcriptional response pattern active for a subset of test compounds and test cell lines. The multiple components encapsulate the genes of the plurality of gene sets.

3) Determining, for a portion of the test agents, a concentration-dependent toxicity reflective of whether a concentration of a test agent applied to a test biological sample to induce a differential expression of genes in the test biological sample is above, equal to or below a defined toxicity level.

4) Identifying, based on the concentration-dependent toxicities, the multiple prediction components as a subset of the multiple components and being predictive of toxicity.

The PTGS score is thereby calculated for an agent based on the proportion of the differential gene expression in the biological sample that belongs to the multiple prediction components identified according to the steps 1) to 4) above. This PTGS score is indicative of a toxicity prediction for the agent and can thereby be used in order to define whether the agent is toxic or not.

In an embodiment, obtaining the gene expression data comprises obtaining genome-wide gene expression data defining the differential gene expression of genes in the biological sample induced by the agent. In this embodiment, the gene expression data thereby represents the gene expression of the complete genome or at least a substantial portion of the genome in the biological sample.

In an embodiment, the biological sample is a cell, a cell line, or a tissue (which has been intoxicated or is becoming intoxicated by exposure to a test agent), preferably an animal cell, cell line, or tissue such as a mammalian cell, cell line, or tissue and more preferably a human cell, cell line or tissue.

In an embodiment, obtaining the gene expression data comprises measuring gene expression of genes in the biological sample induced by the agent. The gene expression data is then determined as differential expression value for the genes between the measured gene expression of the genes in the biological sample induced by the agent and control gene expression of the genes in the biological sample.

The differential expression value thereby represents test statistics and a difference between measured gene expression as induced by the agent and control gene expression without usage of the agent. The differential expression value may be computed as the ratio, or fold-change, for each gene between the treatment and control samples. Also other differential expression values include singed or non-signed t-statistics, p-value or any other way of quantifying differential expression change of a gene, including directional or non-directional changes.

In an embodiment, calculating the PTGS score comprises calculating, based on the gene expression data, the PTGS score representing a proportion of the differential gene expression in the biological sample, induced by the agent, that belongs to 14 prediction components A-N or to 13 prediction components A-K, M and N, wherein component A comprises, preferably consists of, the following genes: CHST3, BICD1, NDST1, VRK1, RBBP6, CYP27B1, GZMB, STIL, MAP2K3, MKLN1, B4GALT7, ZFX, RBM5, ARID4B, ABHD14A, FADS1, SOCS2, PML, MAP3K14, PIR, RBM16, AMOTL2, SNAPC1, ZNF212, FOXJ3, FNBP4, IFI30, CTSH, ABCC10, IMPA2, MTHFD1, MAP2K4, BCL10, KIF18A, UBE2L3, ZC3HAV1, IL1RAP, INTS6, NUP210, JUN, MCM3, TIMP1, BLZF1, RYBP, ZBTB24, CLK1, FBXL5, POLR3F, NDUFA9, SCYL3, KLF7, GADD45A, RPA3, NDUFB7, PRR3, PSPC1, SUV420H1, TGFB3, SLTM, PPIG, GLB1, GAL, DUSP10, DUT, PRKAB1, MORC3, ZCCHC8, EED, KLF6, AHOY, PRKRIP1, AURKA, RAB27A, TOP1, YTHDC1, TFAP2C, IDH1, TNFRSF12A, BAZ2B, ZNF44, DUSP1, GTF2B, CENPC1, JRK, TFRC, RGS2, MYBL1, NFKB1, HIST1H2AC, FKBP4, SMCHD1, IARS, TUFT1, EP300, KLF10, CSTF2T, FAM48A, USP9X, PDIA4, GRB7, NFIB, TSC22D3, BNIP1, KIAA0020, ASNS, PPP1R12A, DLX2, PHB, NEDD9, CAPN1, KIAA1033, TSC22D1, ZFP36, MEIS1, ID3, NFKBIE, ID2, ORC1L, EHD1, PRDX4, ELF3, SDCCAG1, NUDT1, ZNF131, PER1, CYP1B1, TBX3, UST, ISG20, SFRS12, NDST3, EIF2B5, ADM, SETDB1, CKAP4, PLAU, GNL2, E2F3, MAGED1, KIAA0100, LRP8, CYR61, NCK1, ITGA2, CPDX, MYCBP, ADCY9, TFE3, GARS, MGMT, RPN2, MCM6, UCHL3, TLK2, MYD88, SERPINB1, EZH2, MTHFD2, KIN, GRHL2, ZNF217, H2AFV, TCP1, ASNA1, RBM15B, DNAJB1, SAMHD1, SUOX, MAPK6, F3, PPP1R15A, FBXO38, PYCR1, IGFBP2, PRPF38B, PAPOLA, CLIC1, RCHY1, TNFAIP3, CBX5, TUBB, ERCC5, TMEM97, PEX1, CHST7, BIRC3, ICAM1, CNOT8, PGS1, CDKN1B, CTDSP2, DNMBP, NISCH, MATN2, THUMPD2, CHKA, LIMS1, WDR67 and ZCCHC6;

component B comprises, preferably consists of, the following genes: RELB, HBEGF, CCNL1, TNFAIP6, NFKBIE, REL, ARIH1, SOS1, NFKB2, TIPARP, PPP1R15A, BIRC3, FAM48A, TNFAIP3, NR4A2, THUMPD2, CNOT2, ZNF23, PTX3, HIVEP1, DPP8, PPP2R2A, NFE2L2, ELF1, KIF18A, BCL3, EED, SLC20A1, TAP1, CXCL1, ZNF267, BTG1, BTN2A1, SRP54, JUNB, RAC2, AGTPBP1, CCL11, FOS, GLRX, NUPL1, IFI16, HLA-A, RNF111, RBM15, SLC25A6, ZFP36, RYBP, AKAP10, ADORA2B, DAAM1, HLA-E, NFKBIA, IL1B, CD83, RBCK1, LF10, MAFF, RBM5, SEC24A, ZNF45, INTS6, CLK4, CHD1, AZIN1, FAM53C, TLR2, NFKB1, TXNIP, TAPBP, TNFRSF1B, MORC3, CD9, GTF2B, ZCCHC6, WAC, PSPC1, FOSB, CEBPB, IFIH1, NOC3L, NCOA3, RBM38, HLA-B, SIAH2, ATP1A1, PRKRIP1, YY1AP1, KLF6, CREB5, SOD1, PTGS2, RRAD, CDH2, PLAU, EGR1, ING3, ZNF136, TLK2, KRT10, GALNT3, XPC, IGFBP7, PMAIP1, DLX2, FSCN1, IGFBP3, LYN, MICAL2, DUSP6, BTN3A3, PPP1R16B, BAMBI, UPP1, MAP2K3, CLK1, UBC, BAG3, CASP1, IER2, CYR61, FBXO38, MTHFD2, KIN, NR4A1, PNRC1, COL15A1, CHAC1, IL8, CX3CR1, ACTG1, CCL7, NRBF2, PHF1, TRADD, ARNTL, TNF, LAMP3, FTH1, RABGAP1L, WEE1, LCP2, OTUD3, ID3, GABARAPL2, ALAD, GBP1, RABL3, WDR67, TRIB1, ZCCHC10, CREM, IL7R, FNBP4, NR4A3, TUFT1, RLF, NBN, SRPR, GEM, PRPF3, GABARAPL1, CENPC1, MX2, IKBKE, TRAF3, PDLIM7, SLTM, ETS2, AHR, PPP1R12A, ZNF180, IER3, RBM39, HLA-C, PTTG1, TBK1, EGR3, DUSP8, ID2, ERCC1, PLAUR, IGFBP2, CCL4, BCL2L11, PTN, IL15, SPTBN1, MTHFD2L, SDC4, PALM2-AKAP2, BRCA2, EHD1, ZNF588, TAF2, SFPQ, PTPRE, IRF1, IRF7, IL1RAP, COL6A1, EGFR, BAZ1A, USP12, PDGFA, NFIL3, ABCC1, OLR1, PELI1, MAP3K14, ZNF195, DUSP1, RIPK2, BCL10, SUV420H1, CCNT2, JRK, STC2 and TFEC;

component C comprises, preferably consists of, the following genes: CLK4, DUSP1, KLF10, DLX2, EFNA1, NUPL1, POU2F1, NFYA, PSPC1, ZNF263, CLK1, BTG1, TSC22D1, BCL7B, FBXO9, STX3, WEE1, PPM1A, MAFG, SLC38A2, KLF6, ZNF292, IRS2, RBM15, HSF2, DUSP4, BCL6, MKLN1, CYR61, ZNF435, STK17B, AMD1, ZNF281, CCNL1, ZNF239, NEU1, HEXIM1, THUMPD2, UBE2H, PRKRIP1, ZNF23, CD55, TAF5, RBM5, FSTL3, JUND, PITX2, IER5, ZBTB5, CARS, IER2, RABGGTB, STAT3, SIP1, AKAP10, MAP1LC3B, WDR67, NCOA3, ZFP161, BAG3, LRP8, BCL10, FNBP4, PNRC1, PPAT, CETN3, DMTF1, NR4A2, UBE2M, RYBP, YTHDC1, PDGFA, ATP2B1, TIA1, RGS3, PPP1R15A, PRNP, KLF5, CHKA, TMCC1, EPHA2, ELF1, ELF4, THUMPD1, MAFF, ZNF14, SRF, EPAS1, CLK3, EIF2B5, CALU, NRIP1, ID3, H3F3B, REL, SLC3A2, PRKAA1, LDLR, ZBTB43, PBEF1, E2F1, FOXJ3, TNRC6B, MEF2A, TOP1, HSPA1L, ELF3, TFAP2C, ADM, MYD88, TNFRSF12A, PEX13, ILF3, TCEA2, HIST1H2AE, SETDB1, WAC, THBD, IFIT5, NLE1, ARHGEF9, TIPARP, MORC3, PPM1D, DUSP8, EGR1, TCF7L2, SNX5, DNAJB4, DNAJB9, PIAS1, ZNF232, FAM48A, RRAS2, TFE3, ZNF45, PSMD8, SLC20A1, TUFT1, E2F3, DCTN6, KIAA0528, RRS1, GTF3A, SMNDC1, RIPK2, RLF, OTUD3, NOL7, PIK3R1, CCNT2, CLDN4, KIF18A, ZFP36, CFLAR, ZCCHC8, JUNB, TSC22D2, MTMR11, HIVEP1, PCK2, PPP2R1A, JUN, FAM53C, SEC24A, ZNF432, IGFBP3, CYP1B1, BACH1, RNF111, RAB5A, SMAD7, RAB3GAP1, SDCBP, EPHA4, JRK, CNOT8, POP7, TAF5L, PLSCR1, BUB3, NECAP1, BTG2, ZNF136, RIC8B, TADA2L, ZNF22, NMI, YY1AP1, GTF2A2, GRB7, RCHY1, TCF12, NR4A1, NEDD9, NFKBIB, POLR2C, SRRM2, SLCO4A1, SDC4, SHOC2, GEM, SPRY4, ERF, KCNK1, SMCHD1, STATE, KIAA0907, SMTN, MTERF, NBN, TBC1D9, FNDC3B, TDRD7, BAZ2B, ZC3HAV1, DUSP10, PELI1, CAPN1, PGS1, BRD2, NF1, FBXO38, TNFAIP3, ANAPC13, GLUL, PLAU, EIF5, HIC2, NFKBIA, EFNA5, SURF1, CDC42EP4, GADD45A, CDKN1A, SEMA4C, DYNLL1, BTN2A1, BAMBI, HYAL2, LYPLA2, MARCKSL1, ZFAND5, STK4, INHBB, TLK2, ASNS, VCL, CAP2, SOX15, RAD1, PLAUR, RBM15B, PIK3R3, ATF5, UAP1, RBM39, MYB, MYBL1, DNAJB1, TXNL4A, PIR, ABI2, CDC27, ZNF35, SLC25A16, GINS1, ARNTL, UGCG, TFAM, IFRD1, FGFR1OP, LIMA1, DAAM1, E2F5, AGTPBP1, SCYL3, MTF1, SP1, PMS2L1, TPP1, ID2, RUNX1, MXD1, KIAA0802, FOSL2, PTPN2, CNOT4, EHD1, FOSL1, KLHL2, BAZ2A, RNF7, ZNF282, ZNF195, HSP90AB1, SLC25A37, CTGF, NFIC, SFPQ, HRAS, ID4, PPP1R12A, CSNK1D, TRIO, MAP2K4, MARK3, USP1, ZNF189, TM2D1, TAF1C, GAD1, RAB5C, NCBP2, ITPR1, HIST1H2BN, PTPRE, SERPINB1, OGFR, DNAJB6, UBTF, DCLRE1C, NFIL3, TGFB2, ATF2, RAB11FIP2, COL19A1, H2AFX, SNRK, OTUD4, ZFX, CHUK, E2F4, TGFBI, SFRS12, MAP3K1, TNIP1, DTNA, H1FX, ING3, MKRN1, DIXDC1, NUP98, TXNRD1, BNIP1, MAP3K14, CHAC1, ANXA2, MYBL2, FOXM1, CENPC1, PTGES, COX7A2, DDIT4, STAT1, NONO, MNAT1, SFN, ZNF192, GRHL2, SEC61G, NAB2, DNAJC6, TAF2, PPAP2A, INTS6, CAB39, LZTFL1, KPNA5, BTF3, PPP1R13B, SHOX2, CLTB, FOS, SH3BP2, ZNF187, GTF3C4, ZNF205, CYP2J2, NIPSNAP1, CSRP1, IL11, IL15RA, CASP3, SLC9A1, PMAIP1, EIF4E, TTF1, RAB21, ZNF227, LGALS8, HBEGF, TIAL1, NR4A3, ARHGAP29, NOC3L, SPATA5L1, ZNF44, HIST1H4B, SLC7A5, BSG, CDR2, ARG2, FUSIP1, HES1, MITF, TGDS, CYP27B1, RERE, NFIB, SDCCAG1, TCEAL1, ZNF76, ELL2, ARIH1, SUV420H1, TUSC2, SERPINB5, ADFP, UPP1, PITPNB, USP9X, CPEB3, ZNF267, TRIM21, HERPUD1, CEBPG, GTF2H1, PER1, KLF9, PLK2, CREM, TFAP4, CXCR4, SNRPE, CD97, IL6, FHL1, JMJD1C, CCDC6, NHLH2, PAWR, NRBF2, FOXK2, STC2, ERGIC3, TAP1, CEBPB, FOSB, R1D1, SERPINE1, GAS2L1, PPIG, PHF1, ZNF451, DNAJB5, OXSR1, PRPF38B, ARID4B, DR1, RNF6, ZNF588, RELA and BCAR3;

component D comprises, preferably consists of, the following genes: ARID5B, KLHL9, POLD3, CENPA, SLC25A12, PTPN3, NPAT, BTAF1, CNOT2, MTMR4, CEP350, BLM, RIF1, RAD54B, TNFRSF1A, GNL2, PUM2, INSIG2, ANKMY2, BAZ2B, POLE2, GNE, NTF3, ATP2C1, SMURF2, ASXL1, CENPF, ZNF318, DTL, NCOA3, RAD51C, SFRS9, TLK2, DOPEY1, LRP6, RPP14, CHD1, SKIV2L2, SOCS6, MAGEF1, ARHGEF7, RBM39, UBR2, PEX14, SFRS3, PANX1, WAPAL, MAT2A, IGF1R, SLBP, FADD, ZBTB24, NUP153, GIPC1, ARIH1, CCT4, MLX, TOPBP1, CASK, DNAJA2, FZD2, BARD1, SACS, ZZZ3, ADORA2B, XPO1, DHX15, NIPBL, ORC2L, SIRT1, KIF5C, WWP1, CENPE, RANBP2, STARD13, MAPK6, BMPR1A, SRGAP2, TRAM2, PHF3, NCK1, HMGB2, FAM48A, COIL, CENPC1, LPP, KIAA0528, TMCC1, EFNB2, UBN1, PSMC2, TARDBP, TRIM32, TPST1, BRD8, RABGAP1, KIF11, IFRD1, MYCBP2, MEIS1, RUNX1, NR2F2, PAFAH1B1, LRIG1, HERPUD1, KIF2A, PARP1, KEAP1, SUZ12, PPP2R2A, TXNRD1, UBE2N, GBAS, TNFAIP8, CUL1, KIAA0922, GCC2, CTNND1, SMC4, GTF2E1, DNMBP, ANKRD17, SOS1, PPM1B, NRG1, CASP8, CORO1C, ZNF146, E2F5, SEC24B, PER2, CRK, RNF14, RBM5, PCNA, UBE2G1, HSPA8, MELK, HNRPDL, SMAD4, PLK4, RCOR1, RSBN1, FNBP1L, CCNA2, BCAR3, CAMSAP1L1, USP12, RRS1, CRLF3, ZFAND5, XBP1, MRFAP1L1, NCOA6, APPBP2, DDX10, SRPK2, KIAA0947, PKD2, TUBGCP3, PHF21A, FBX046, AMD1, DMTF1, PPRC1, WDHD1, PPP1CC, KIAA1279, GCLC, NET1, ZNF638, FCHSD2, FUT8, PDGFB, ABL1, ZNF451, STK3, SLC4A1AP, USP22, HSPH1, PEX1, JMJD1C, HS3ST3B1, OSBP, TCERG1, NUP98, BIRC2, USP1, ELF1, MRPL15, PIP5K2B, WEE1, ARF6, N4BP1, FNDC3A, CRKL, ADNP, SERTAD2, FRYL, MAP3K4, TBK1, PMP22, KIAA0174, UTP18, SSFA2, HMGCR, CHSY1, BAG2, R3HDM1, HIVEP1, BLCAP, PIK3C3, FAF1, REV3L, GCNT1, KIAA1012, RAB5A, FOXK2, MAP3K5, MLH3, CEP55, TRIM33, ATF2, ANKS1A, GAPVD1, MGLL, CEP135, ID11, KIF14, ZNF281, SON, R3HDM2, CKAP5, POGZ, XRCC5, TBC1D8, NAP1L1, TRIM2, SUPV3L1, SHOC2, THUMPD1, KIF23, NOC3L, CTCF, MYO10, LHFPL2, USP8, CDH2, PSMD12, IRS1, PTK2, ARID3A, WDR7, AURKA, MEGF9, EGFR, PDCD10, RASA1, RABGGTB, FBXL7, GBE1, PAPPA, USP6, LRRC42, KBTBD2, STXBP3, MORC3, USP10, STAM, MEIS2, TFAP2C, PCCA, RBM15B, PGRMC2, G6PD, TIAM1, CDC6, TRIM37, TAF5L, USP6NL, NASP, FZD1, PDE4B, MTX2, TRIP4, ENOSF1, BAZ1A, DYRK2, INPP5F, ZBED4, ELF4, SFRS4, SPOP, MAP2K1, ITSN2, MPHOSPH6, PTPRK, SMAD3, AKAP9, DICER1, PFTK1, R140, RFTN1, LARP4, MPHOSPH9, PSMD14, MTM1, TOP2A, USP3, IL4R, NFE2L2, CBLB, CTDSP2, RARS, ARHGAP29, IL7R, BAT2D1, KIAA1128, ACVR1, DCUN1D4, EMP1, GTF2H1, BACH1, TCF12, RBM25, RBM16, DYRK1A, PITPNB, FNTA, ATP6V1B2, MNAT1, ZFP36L2, ARHGEF2, GATA2, STX3, ACVR2A, RAB11A, MTMR3, RNGTT, KIAA0232, SLK, PMM2, PHC2, PCNT, GTF2F2, NPEPPS, ITSN1, CPT1A, SLC25A17, ZNF292, CUL2, GULP1, CREBBP, MAP1B and STK38;

component E comprises, preferably consists of, the following genes: SERPINH1, MCM7, RFC4, HSPA4L, DNAJA1, MCM3, E2F1, AHSA1, MAFG, MCM6, DDX11, RFC5, NASP, CDC45L, PRIM1, BRCA1, RBM5, ATP6V1G1, MSH6, MCM5, FEN1, MCM4, TMEM97, ZFAND5, GTF3C3, MCM10, TPP1, CCNB1, CDC25A, CHEK1, RAD51C, APEX1, BAG2, BLM, POLE2, ATAD2, UNG, CCND1, RMI1, PLOD1, USP1, DNAJB6, EXO1, RAD51, CDC2, CDC7, PMS1, PCNA, PRNP, VRK1, CDCA4, ME1, CHAF1A, KCNK1, HDAC6, TMEM106C, CCNE1, DLEU1, MLLT11, CEBPG, XRCC5, POLD2, UBE2B, EED, RFC2, UMPS, PKMYT1, PA2G4, TYMS, MNAT1, PPIH, PSMD11, POLD1, FLAD1, TFE3, CDKN2C, FKBIA, MAZ, CDK4, CCNE2, RECQL4, EZH2, TRIP13, MCM2, INTS6, TFDP1, RAB27A, CCNH, DNTTIP2, DDB2, RELA, HDAC2, FANCL, PTTG1, CDK7, PIK3R1, SOD1, ATP6V0A1, MSH2, ADFP, SLBP and IL10RA;

component F comprises, preferably consists of, the following genes: ARID5B, RLF, FBXL5, KLHL9, MTF2, ZNF435, POGZ, BTN2A1, BRD1, FEM1C, BAZ2B, RANBP6, COIL, BACH1, ZNF3, RBM4B, ZNF45, ARID4B, ARHGEF7, CSTF1, CLK4, NCOA3, CENPC1, NCK1, NFIL3, RPP38, CHD9, ZNF180, ZNF588, ZNF131, CDC42EP2, RNF113A, TLK2, ZNF44, RIC8B, KBTBD2, BAG5, RBM39, RBM15, ZBTB24, NEDD9, STARD13, SCYL3, ZNF432, SEC31A, INTS6, JMJD1C, ZNF14, TCF21, ZNF23, FOXJ3, NUP153, ZNF217, CLK1, DUSP4, KIF2A, ZNF195, RIPK2, GTF2E1, ZNF451, TIPARP, PGS1, MYC, NGDN, PNRC2, PRPF3, CRKL, ADNP, ZNF292, MORC3, POLS, RBM5, ZCCHC8, ZNF274, ZCCHC6, KIAA0907, TBK1, IER2, ZNF187, STC2, RNF111, KLF6, CNOT2, CHD1, DYRK2, ZNF146, SUV420H1, DCLRE1C, FNBP4, ZNF267, CEP76, CDKN1B, MGMT, MEIS1, KIAA0174, ZNF148, IRS1, DMTF1, E2F3, BCL10, SHOC2, CCNT2, CDK7, SMAD3, TNFAIP8, THUMPD2, EIF5, ING3, RBM16, FADD, ETFB, WEE1, SETDB1, RND3, AMOTL2, ID2, SIX1, ARIH1, DUSP8, AKAP10, MAST4, FAM48A, NTF3, PSPC1, DNMBP, SOCS2, NRBF2, ANKRD46, JUNB, WSB1, CENPA, TNFRSF1A, IFRD1, NFKBIA, BIRC2, ZNF227, KIF18A, TSC22D1, BCL7A, CCNL1, CEBPB, EPM2AIP1, TUFT1, ITPKB, HF3, FBXO38, REV3L, WDR67, ADORA2B, HMGCR, RRS1, NR2F2, ZNF165, N4BP1, PPWD1, RCHY1, KIN, BRD8, CTCF, CEBPG, YY1AP1, KLF5, POLR3F, SPOP, ETS2, NOC3L, FZD2, ASB1, PELI1, TCF7L2, SIAH1, RYBP, SFRS12, PIM1, DDIT4, OLFM4, ZZZ3, ZNF35, PGRMC2, AMD1, AHDC1, JUN, UMPS, BICD1, CSTF2T, TSPYL5, WAC, RABGGTB, SOX4, GAS1, KIAA1462, SIAH2, SLC25A44, ASNS, ZNF331, SKIV2L, YTHDC1, SACS, PRKRIP1, HSPB3, PRR3, BRWD1, RBBP6, PPP1R12A, PHC2, ZCCHC10, FRMPD4, NFKBIE, IL4R, KLF7, MARK3, CITED2, TRAM2, BLCAP, MYST3, ERCC5, PRPF38B, AURKA, OSR2, MYO10, GNRH1, CASP8, PTN, SDCCAG1, TRAF4, HMGB2, FAM53C, GATA3, PTGS2, CEP68, ZNF136, TNFRSF9, PIK3R4, HSPB6, KLF10, PIWIL1, SCHIP1, SLK, SNAI2, VPS13D, CYR61, ERF, MAFF, GCNT1, BDKRB2, DYRK1A, CHAC1 and ZNF629;

component G comprises, preferably consists of, the following genes: EGR1, JUN, FOS, DDIT3, TNFAIP3, PMAIP1, NFKBIA, GADD45A, NR4A1, GEM, DUSP1, FOSL1, SLC3A2, IER2, EIF1AX, KLF10, KLF2, GINS2, FHL2, FOSB, AKT1, NR4A2, JUNB, HES1, CD55, IER3, DNAJB9, IL8, PCNA, DUSP4, TIMP3, PLAU, SLC39A14, RGS2, TSC22D1, CEBPB, ALAD, SNAI1, HIST1H3B, DAG1, IRF7, CREM, CD59, BCL6, AHR, BTG2, BRCA2, HMGCR, NR4A3, MAPK9, FSCN1, HBEGF, EGR3, MVD, LIF, KLF4, CDC45L, ARMET, HIST1H2BC, BAIAP2, PRNP, ETS2, POP4, SHC1, ELF3, OASL, C10orf119, CPEB3, CSTF2, FGFR3, CCL5, CRKL, BRAF, ISG20, TSFM, KIAA0146, JUND, GLA, GTF2B, ITPR1, CYP1B1, SYK, MAP1B, RELB, STAT3, LITAF, PPAN, SLC9A1, GLRX, NR1D1, EGR4, NP, ABCF2, FST, CSE1L, FTSJ3, HIST1H3G, RDH11, MYD88, RANBP1, C8orf4, CTGF, RXRA, GRB7, NFKB2, MAFG, TRAP1, TOMM20, CDKN2C, ANGPTL4, HDAC5, RRAD, PPARA, SF3A3, EGR2, FGF18, FBP2, TXNIP, MRPS18B, CTH, SLC12A7, CBFA2T3, ID3, ASAH1, PES1, C21orf33, F11R, SULF1, GAL, PIK3R1, KRT17, SRF, BCR, CLDN4, FOSL2, RUNX1 and SAC3D1;

component H comprises, preferably consists of, the following genes: OPTN, CD8B, IGFBP3, LAMA4, BTG1, TF, YKT6, ANXA2P3, CTSL2, ALDOA, IGFBP2, KRT7, RHOB, RREB1, NEU1, GRN, CDKN1A, S100P, IFI30, SERPINE1, ERCC2, KCNA1, GEM, TGM2, ITM2B, RPS27L, DUSP1, CSRP1, AKR7A2, MDK, RNASET2, ACAA1, ADM, GPS2, CEBPB, SNAI1, ZFP36, NR4A2, KLF4, CITED2, B2M, ECHS1, TNFAIP3, EIF4E, CD44, MPV17, ASNA1, LITAF, LCN2, BSG, MMP1, PTGES2, MAP1LC3B, ARMET, HRSP12, TNFSF9, ID2, CLTB, SOX15, AAMP, FOS, CTGF, SERPINB2, SIPA1, GUK1, TPP1, TSPYL2, PSAP, NR4A1, ERCC1, HADHB, CD9, FURIN, IMP2, FOSB, RPS6KB2, CGREF1, IL18RAP, JUNB, C10orf119, LENG4, CLU, WDR12, SCG5, FTSJ1, NFKB2, PHLDA2, GABARAPL1, SH3BGRL3, HBEGF, TGFBI, SCD, ULBP2, RELA, RPS4Y1, SURF1, KRT17, GADD45A and CACNA1G;

component I comprises, preferably consists of, the following genes: INPP4B, PDGFB, PHC2, SMAD3, KRT7, IGFBP3, IFNG, STC2, IL18, DKK1, LIMA1, SLC2A1, ACTG1, PLAT, SMURF2, CYR61, UAP1, CTSE, IL8, EFEMP1, PLK2, IL7R, BIK, SERPINE1, NMT2, HDAC9, ADORA2B, CXCL1, DUSP14, TACSTD2, CST6, BASP1, TGFB2, PTX3, GPRC5A, MT2A, TGM2, TNFAIP3, PHLDA1, CDH2, PLA2G4A, TMEM47, CXCL2, LIPG, GADD45A, TSG101, PLOD2, MAPK9, NFKBIA, LAMB3, CTGF, CXCL6, FHL2, LAMA5, EPHA2, FGF2, PLAU, TUFT1, GLIPR1, MAP2K3, CDKN1A, TEK, IFRD1, PTGS2, ID2, MLLT11, BNIP3, BAG3, ATP1B1, NCF2, IGF2, CXCR7, ADM, FLRT2, CD83 and IGF2BP3;

component J comprises, preferably consists of, the following genes: PSPC1, NEDD9, CAB39, RYBP, SEC31A, PPP1R15A, MAFF, PCDH9, JUN, DAAM1, CNN1, ZCCHC6, ADM, DIXDC1, TNFAIP3, PMAIP1, ADFP, TSC22D3, ZNF432, ZNF267, AGTR1, NFIL3, BCL6, ZNF588, KLF6, PTPRE, TNFRSF9, RLF, SFPQ, PER1, ADORA2B, ASNS, NCOA3, PPAP2A, CLK1, INTS6, FEM1C, MEF2A, TPM2, ELF1, DUSP1, FBXO38, ZNF3, GLUL, DMTF1, BBC3, BACH1, USP12, CRY1, SFRS12, TXNIP, LIMK2, RBM15, RAC2, ENC1, SCYL3, JMJD1C, NAT1, TBCC and SEC24A;

component K comprises, preferably consists of, the following genes: RPA1, EZH2, MCM5, RFC3, TOPBP1, MCM3, FLAD1, CDC7, MCM2, PRC1, E2F8, UNG, DCK, MAD2L1, TYMS, POLG, BRCA1, HELLS, BARD1, CCNE1, DDX11, MCM7, ORC1L, CDC45L, FEN1, MSH2, TFDP1, FOXM1, CHAF1A, ILF2, KIF4A, MCM4, ASF1B, PCNA, ORC6L, RAD51, RACGAP1, CDK2, MYBL2, RAD51AP1, PRPS1, RFC5, RRM2, POLD3, CCNE2, NEK4, NASP, GMNN, DDX23, UCHL5, USP1, MCM6, MCM10, TRIP13, SNRPD1, RFC2, SLBP, TSFM, RFC1, POLE, KIF20A, POLE2, TFAM, DTL, KIF11, POLD2, BLM, RFC4, MK167, MRPS12, POLA1, CDC20, SMC2, DTYMK, ZWINT, PRIM1, SLC29A1 and RAD51C;

component L comprises, preferably consists of, the following genes: HMGCL, ABAT, ADH5 and PGD;

component M comprises, preferably consists of, the following genes: EIF4EBP1, ASS1, MARS, LARS2, PSPH, SARS, EPRS, PHGDH, XPOT, CEBPG, PCK2, GARS, TARS, SLC1A5, CARS, SLC1A4, FYN, AARS, ASNS, VLDLR, CEBPB, MTHFD2, WARS, HAX1, YARS, HARS, ITGB3BP, LAPTM5, MAP1LC3B, TRIB3, IARS and NARS; and component N comprises, preferably consists of, the following genes: RELB, NFKBIA, SUOX, TNFAIP3, ETS2, NFKB2, HIVEP1, NFKBIE, CD83, RXRA, CEBPB, JUNB, IKBKE, NFKB1, BIRC3, ICAM1, ADAM8, IER3, TNIP1, CXCL2, PTX3, BCL3, GADD45A, TAP1, TNFAIP2, PDGFA, IL8, CFLAR, JUN, BTG2, PLXNB2, ARID5B, SDC4, IL1B, RGS16, KRT14, IL7R and CXCL3.

The above listed components A-N constitute the prediction components identified as previously described herein. The respective genes of each prediction component are presented above using Ensembl gene identifiers.

In an embodiment, all 14 prediction components A-N are used in the calculation of the PTGS score. In another embodiment, 13 prediction components A-K, M, and N are used in the calculation of the PTGS score. In yet another aspect of the invention combinations of components motivated by co-clustering of components (as defined in example 4) and, preferably, also by shared functionality seen in the validation against external data, for instance, components G, H, N and I can be used for predicting liver in vivo and in vitro intoxication (as described in examples 4 and 6), components E and K can be used for the strong associations to cell cycle regulation (as described in example 4) and components N and I for the high sensitivity as early biomarkers for overall toxicity (as described in example 5). In a further aspect of the invention, the overlap of PTGS-associated genes and genes regulated as targets of PTGS-associated transcriptional regulators can be used as a sub-set of PTGS-associated genes to assess transcription factor mediated toxicity pathways in the context of the PTGS (as described in example 5). Thus, embodiments as disclosed herein involve using different combinations of the 14 prediction components A-N, for instance prediction components G, H, N and I, prediction components E and K, prediction components N and I, in order to predict toxicity of an agent, such as by calculating a PTGS score. Related embodiments involve predicting toxicity of an agent by investigating differential gene expression for genes belonging to prediction components in such combinations, such as the genes, or at least a portion thereof, belonging to prediction components G, H, N and I, belonging to prediction components E and K, or belonging to prediction components N and I.

Another aspect of the embodiments relates to a method of predicting toxicity of an agent. The method comprises obtaining gene expression data defining differential gene expression of toxicity representing genes in a biological sample induced by the agent. The toxicity representing genes are identified by the following steps:

1) Transforming gene data defining, for each instance of a plurality of instances, differential gene expression of genes in a test biological sample induced by a test agent into gene set data defining, for each instance of said plurality of instances, an activation value for each gene set of a plurality of gene sets. An instance defines a unique pair of a test agent and a test biological sample, a gene set represents a collection of similar individual genes.

2) Performing a probabilistic component modeling on the gene set data to define multiple components representing a respective specific compound-induced transcriptional response pattern active for a subset of test compounds and test cell lines. The multiple components encapsulate the genes of the plurality of gene sets.

3) Determining, for a portion of said test agents, a concentration-dependent toxicity reflective of whether a concentration of a test agent applied to a test biological sample to induce a differential expression of genes in the test biological sample is above, equal to or below a defined toxicity level.

4) Identifying, based on the concentration-dependent toxicities, the multiple prediction components as a subset of the multiple components and being predictive of toxicity.

5) Identifying the toxicity representing genes as genes belonging to the multiple prediction components.

The method also comprises predicting toxicity of the agent based on a percentage of the toxicity representing genes that are significantly differentially expressed in the biological sample as induced by the agent.

In an embodiment, the toxicity representing genes are the above listed genes for the prediction components A-N or for the prediction components A-K, M and N. In another embodiment, the toxicity representing genes are the above listed genes for a combination of the prediction components A-N.

In this method, gene expression of the toxicity representing genes are determined in order to calculate the percentage of the toxicity representing genes that are significantly differentially expressed in the biological sample as induced by the agent. Generally, the larger the percentage of the toxicity representing genes that are significantly upregulated or downregulated as induced by the agent the more toxic the agent is.

In an embodiment, transforming the gene data comprises transforming the gene data into the gene set data defining, for each instance of said plurality of instances, a positive activation value and a negative activation value for each gene set of said plurality of gene sets. In this embodiment, the positive activation value represents a probability value for increased differential gene expression of the collection of similar individual genes in the gene set as induced by a test agent in a test biological sample. Correspondingly, the negative activation value represents a probability value for decreased differential gene expression of the collection of similar individual genes in the gene set as induced by the test agent in said the cell line.

In an embodiment, transforming the gene data comprises computing gene set enrichment analysis, GSEA, on the gene data to get, for each gene set of the plurality of gene sets, the positive activation value based on a false discovery rate q-value (FDRq) representing the strength and direction of positively activated genes of the gene set and the negative activation value based on a FDRq value representing the strength and direction of negatively activated genes of the gene set.

In an embodiment, performing the probabilistic component modeling comprises performing Latent Dirichlet allocation (LDA) modeling on the gene set data to define the multiple components.

In an embodiment, performing the LDA modeling comprises defining, for each instance i of the plurality of instances, a probabilistic assignment vector p(z|i) to component z. A probabilistic assignment vector p(z|gs) to a gene set gs is defined for each component z of the multiple components. A minimum number of components is selected while maximizing mean average precision of the LDA modeling based on the probabilistic assignment vectors. The result of such LDA modeling is the previously mentioned multiple components.

In an embodiment, determining the concentration-dependent toxicity comprises calculating, for each test compound of the portion of said test agents, a difference of the logarithmic concentration of the test agent as applied to the test biological sample to induce the differential gene expression in the test biological sample and a concentration value inducing a measurable effect on cell growth or viability in the test biological sample.

In an embodiment, the concentration value inducing a measurable effect on cell growth or viability in the test biological sample is a concentration value inducing 50% growth inhibition (GI50), total growth inhibition (TGI), or lethal concentration 50% (LC50).

In an embodiment, identifying the multiple prediction components comprises ranking the multiple components based on their probability-weighted mean concentration-dependent toxicity values $TOX_z$ over the portion of the test agents as training instances i. In an embodiment, $TOX_z = \Sigma_i [p_n(i|z) \cdot TOX_i]$ and the normalized probabilities $p_n(i|z)$ for the training instances i to belong to component z is computed as $$p_n(i|z) = \frac{p(z|i)}{\Sigma_{i'} p(z|i')}.$$

Cumulative concentration-dependent toxicity classification performance for the multiple components is evaluated in ranked order by calculating area under receiver operating characteristic (ROC) curve (AUC) value for each component count. The multiple prediction components are identified as the highest ranked components resulting in an AUC value corresponding to a defined percentage, preferably 95%, of the highest AUC value.

In an embodiment, identifying the multiple prediction components comprises identifying the previously mentioned prediction components A-N.

In an embodiment, performing the probabilistic component modeling comprises performing the probabilistic component modeling on the gene set data to define 100 components representing a respective specific compound-induced transcriptional response pattern active for the subset of test compounds and test cell lines. In this embodiment, identifying the multiple prediction components comprises identifying, based on the concentration-dependent toxicities, 13 or 14 prediction components as a subset of the 100 components and being predictive of toxicity. These 13 or 14 prediction components are preferably components A-K, M and N or A-N mentioned above.

In an embodiment, transforming the gene data comprises transforming the gene data derived from the U.S. Broad Institute Connective Map (CMap) dataset of gene expression induced by drugs in human breast cancer cell line MCF-7, human prostate cancer cell line PC3 and human promyelocytic leukemia cell line HL60 into the gene set data. In this embodiment, determining the concentration-dependent toxicity comprises calculating, for each test compound common to the CMap dataset and the NCI-60 DTP Human Tumor Cell Line Screen, a difference of the logarithmic concentration of the test agent as applied to the MCF-7, PC3 or HL60 cell line according to the CMap dataset and a concentration value inducing 50% growth inhibition (GI50) in the MCF-7, PC3 or HL60 cell line according to the NCI-60 DTP Human Tumor Cell Line Screen.

In a particular embodiment, the raw data derived from the CMap data set is robust multi-array (RMA) normalized. The method also comprises selecting RMA normalized raw data obtained using microarray platform HT-HG-U133A for the MCF-7, PC3 and HL60 cell lines. In this particular embodiment, gene expression data corresponding to the 5% of the genes displaying highest variance in control measurements for the MCF-7, PC3 and HL60 cell lines are removed. Differential gene expression is then calculated as $\log_2$ ratio between drug-induced gene expression and control gene expression for the MCF-7, PC3 and HL60 cell lines.

This particular embodiment thereby pre-processes the raw data from the CMap data set prior to transforming it into the gene set data. Such pre-processing reduces noise and generally improves the gene data.

A further aspect of the embodiments relates to a method of predicting toxicity of an agent. The method comprises obtaining gene expression data defining differential gene expression of toxicity representing genes or at least a defined portion of the toxicity representing genes in a biological sample induced by the agent.

The toxicity representing genes comprises the genes RELB, HBEGF, CCNL1, TNFAIP6, NFKBIE, REL, ARIH1, SOS1, NFKB2, TIPARP, PPP1R15A, BIRC3, FAM48A, TNFAIP3, NR4A2, THUMPD2, CNOT2, CLK4, DUSP1, KLF10, DLX2, EFNA1, NUPL1, POU2F1, NFYA, PSPC1, ZNF263, CLK1, BTG1, TSC22D1, BCL7B, FBXO9, STX3, WEE1, PPM1A, MAFG, SLC38A2, KLF6, ZNF292, IRS2, RBM15, HSF2, DUSP4, BCL6, MKLN1, CYR61, ZNF435, STK17B, AMD1, ZNF281, ZNF239, NEU1, HEXIM1, UBE2H, PRKRIP1, ZNF23, CD55, TAF5, RBM5, FSTL3, JUND, PITX2, IER5, ZBTB5, CARS, IER2, RABGGTB, STAT3, SIP1, AKAP10, MAP1LC3B, WDR67, NCOA3, ZFP161, BAG3, LRP8, BCL10, FNBP4, PNRC1, PPAT, CETN3, DMTF1, UBE2M, RYBP, YTHDC1, PDGFA, ATP2B1, TIA1, RGS3, PRNP, KLF5, CHKA, TMCC1, EPHA2, ELF1, ELF4, THUMPD1, MAFF, ZNF14, SRF, EPAS1, CLK3, ARID5B, KLHL9, POLD3, CENPA, SLC25A12, PTPN3, NPAT, BTAF1, MTMR4, SERPINH1, MCM7, RFC4, HSPA4L, DNAJA1, MCM3, RLF, FBXL5, MTF2, POGZ, BTN2A1, BRD1, FEM1C, BAZ2B, RANBP6, COIL, BACH1, ZNF3, RBM4B, ZNF45, ARID4B, ARHGEF7, CSTF1, CENPC1, NCK1, NFIL3, RPP38, CHD9, ZNF180, ZNF588, ZNF131, CDC42EP2, RNF113A, TLK2, ZNF44, RIC8B, KBTBD2, BAG5, RBM39, ZBTB24, NEDD9, STARD13, SCYL3, ZNF432, SEC31A, INTS6, JMJD1C, TCF21, FOXJ3, NUP153, ZNF217, KIF2A, ZNF195 RIPK2, GTF2E1, ZNF451, PGS1, MYC, NGDN, PNRC2, PRPF3, CRKL, ADNP, MORC3, POLS, ZCCHC8, ZNF274, ZCCHC6, EGR1, JUN, FOS, DDIT3, PMAIP1, NFKBIA, GADD45A, NR4A1, GEM, FOSL1, SLC3A2, EIF1AX, KLF2, GINS2, FHL2, FOSB, RPA1, EZH2, MCM5, RFC3.

In an embodiment, the defined portion of the toxicity representing genes comprises at least 50% of the toxicity representing genes, preferably at least 75% of the toxicity representing genes, more preferably at least 80%, or at least 85%, or at least 90% or at least 95% of the toxicity representing genes.

The method also comprises predicting toxicity of the agent based on a percentage of the toxicity representing genes that are significantly differentially expressed in the biological sample as induced by the agent.

The above listed 199 genes constitute the most representative toxicity representing genes among the 1331 genes in the prediction components A-N.

This means that instead of calculating the PTGS score or predicting the percentage of the toxicity representing genes of the prediction components A-N or A-K, M and N that significantly differentially expressed as mentioned above only the above 199 genes or the defined portion thereof are used to assess the toxicity of an agent.

Yet another aspect of the embodiments relates to a method of predicting toxicity of an agent. The method comprises obtaining gene expression data defining differential gene expression of toxicity representing genes in a biological sample induced by the agent.

In an embodiment, the toxicity representing genes comprise at least one gene regulated by each transcription factor selected from the group consisting of TP53, EP300, CDKN2A, PPARG, HIF1A, RELA, RB1, NR3C1, NFKBIA, ESR1, STAT5A, JUN, STAT3, SP1, SMARCA4, SMAD7, RARB, MYC, JUNB, EGR1, E2F1, CTNNB1, BRCA1, ATF2, RBL1, NFKB1, FOS, E2F3, CREBBO, SRF, NCOR2, HTT, ELK1, CYLD, and CREM.

The method also comprises predicting toxicity of the agent based on a percentage of the toxicity representing genes that are significantly differentially expressed in the biological sample as induced by the agent.

In this embodiment, the toxicity representing genes are a set of genes with at least one gene regulated by each of the transcription factors listed above. The list comprises 35 transcription factors. Accordingly, there is in total at least 35 toxicity representing genes in this embodiment.

Experimental data as represented herein indicates that genes regulated by these transcription factors are in particular representative of toxicity of an agent. The genes regulated by these transcription factors are preferably selected among the 1331 genes of the prediction components A-N or among the 199 toxicity representing genes previously mentioned herein.

In the above described embodiments, predicting toxicity of the agent comprises predicting the agent to be toxic if at least 25% of the toxicity representing genes are significantly differentially expressed in the biological sample as induced by the agent.

This means that if the agent is capable of inducing a significant upregulation or downregulation of at least 25% of the toxicity representing genes in the biological sample, such as cell or cell line, the agent is predicted to be toxic. If less than 25% of the toxicity representing genes are significantly differentially expressed in the biological sample as induced by the agent then the agent is predicted to be non-toxic.

In an embodiment, obtaining the gene expression data comprises measuring gene expression of the toxicity representing genes in the biological sample induced by the agent. The gene expression data is then determined as differential expression values, such as fold change values, for the toxicity representing genes between the measured gene expression of said toxicity representing genes in the biological sample induced by the agent and control gene expression of the toxicity representing genes in the biological sample.

The methods of the various aspects may be implemented as a computer program comprising instructions, which when executed by a processor, cause the processor to perform the above listed steps or operations. Thus, at least some of the steps, functions, procedures, modules and/or blocks described herein are implemented in a computer program, which is loaded into a memory for execution by processing circuitry including one or more processors. The processor and memory are interconnected to each other to enable normal software execution.

The term 'processor' should be interpreted in a general sense as any system or device capable of executing program code or computer program instructions to perform a particular processing, determining or computing task. The processing circuitry including one or more processors is thus configured to perform, when executing the computer program, well-defined processing tasks such as those described herein. The processing circuitry does not have to be dedicated to only execute the above-described steps, functions, procedure and/or blocks, but may also execute other tasks.

The proposed technology also provides a carrier comprising the computer program. The carrier is one of an electronic signal, an optical signal, an electromagnetic signal, a magnetic signal, an electric signal, a radio signal, a microwave signal, or a computer-readable storage medium.

By way of example, the software or computer program may be realized as a computer program product, which is normally carried or stored on a computer-readable medium, preferably non-volatile computer-readable storage medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blue-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processor thereof.

In an embodiment, the computer program comprises instructions, which when executed by a processor, cause the processor to transform gene data defining, for each instance of a plurality of instances, differential gene expression of genes in a test biological sample induced by a test agent into gene set data defining, for each instance of the plurality of instances, an activation value for each gene set of a plurality of gene sets. An instance defines a unique pair of a test agent and a test biological sample and a gene set represents a collection of similar individual genes. The processor is also caused to perform a probabilistic component modeling on the gene set data to define multiple components representing a respective specific compound-induced transcriptional response pattern active for a subset of test compounds and test cell lines. The multiple components encapsulate the genes of the plurality of gene sets. The processor is further caused to determine, for a portion of the test agents, a concentration-dependent toxicity reflective of whether a concentration of a test agent applied to a test biological sample to induce a differential gene expression in the test biological sample is above, equal to or below a defined toxicity level. The processor is additionally caused to identify, based on the concentration-dependent toxicities, multiple prediction components as a subset of the multiple components and being predictive of toxicity. The PTGS score is defined as a proportion of differential gene expression, induced by an agent, that belongs to the multiple prediction components.

In another embodiment, the computer program comprises instructions, which when executed by a processor, cause the processor to obtain gene expression data defining differential gene expression of genes in a biological sample induced by the agent. The processor is also caused to calculate, based on the gene expression data, a predictive toxicogenomics space, PTGS, score indicative of a toxicity prediction for the agent. The PTGS score represents a proportion of the differential gene expression in the biological sample, induced by the agent that belongs to multiple prediction components. The multiple prediction components are identified by:

1) Transforming gene data defining, for each instance of a plurality of instances, differential gene expression of genes in a test biological sample induced by a test agent into gene set data defining, for each instance of the plurality of instances, an activation value for each gene set of a plurality of gene sets. An instance defines a unique pair of a test agent and a test biological sample and a gene set represents a collection of similar individual genes.

2) Performing a probabilistic component modeling on the gene set data to define multiple components representing a respective specific compound-induced transcriptional response pattern active for a subset of test compounds and test cell lines. The multiple components encapsulate the genes of the plurality of gene sets.

3) Determining, for a portion of the test agents, a concentration-dependent toxicity reflective of whether a concentration of a test agent applied to a test biological sample to induce a differential expression of genes in the biological sample is above, equal to or below a defined toxicity level.

4) Identifying, based on the concentration-dependent toxicities, the multiple prediction components as a subset of the multiple components and being predictive of toxicity.

A further embodiment defines a computer program comprising instructions, which when executed by a processor, cause the processor to obtain gene expression data defining differential gene expression of toxicity representing genes in a biological sample induced by the agent. The toxicity representing genes are identified by:

1) Transforming gene data defining, for each instance of a plurality of instances, differential gene expression of genes in a test biological sample induced by a test agent into gene set data defining, for each instance of the plurality of instances, an activation value for each gene set of a plurality of gene sets. An instance defines a unique pair of a test agent and a test biological sample and a gene set represents a collection of similar individual genes.

2) Performing a probabilistic component modeling on the gene set data to define multiple components representing a respective specific compound-induced transcriptional response pattern active for a subset of test compounds and test cell lines. The multiple components encapsulate the genes of the plurality of gene sets.

3) Determining, for a portion of the test agents, a concentration-dependent toxicity reflective of whether a concentration of a test agent applied to a test biological sample to induce a differential expression of genes in the biological sample is above, equal to or below a defined toxicity level.

4) Identifying, based on the concentration-dependent toxicities, the multiple prediction components as a subset of the multiple components and being predictive of toxicity.

5) Identifying the toxicity representing genes as genes belonging to the multiple prediction components.

The processor is also caused to predict toxicity of the agent based on a percentage of the toxicity representing genes that are significantly differentially expressed in the biological sample as induced by the agent.

In a further embodiment, the computer program comprises instructions, which when executed by a processor, cause the processor to obtain gene expression data defining differential gene expression of toxicity representing genes or at least a defined portion of the toxicity representing genes in a biological sample induced by the agent. The toxicity representing genes comprises the genes RELB, HBEGF, CCNL1, TNFAIP6, NFKBIE, REL, ARIH1, SOS1, NFKB2, TIPARP, PPP1R15A, BIRC3, FAM48A, TNFAIP3, NR4A2, THUMPD2, CNOT2, CLK4, DUSP1, KLF10, DLX2, EFNA1, NUPL1, POU2F1, NFYA, PSPC1, ZNF263, CLK1, BTG1, TSC22D1, BCL7B, FBXO9, STX3, WEE1, PPM1A, MAFG, SLC38A2, KLF6, ZNF292, IRS2, RBM15, HSF2, DUSP4, BCL6, MKLN1, CYR61, ZNF435, STK17B, AMD1, ZNF281, ZNF239, NEU1, HEXIM1, UBE2H, PRKRIP1, ZNF23, CD55, TAF5, RBM5, FSTL3, JUND, PITX2, IER5, ZBTB5, CARS, IER2, RABGGTB, STAT3, SIP1, AKAP10, MAP1LC3B, WDR67, NCOA3, ZFP161, BAG3, LRP8, BCL10, FNBP4, PNRC1, PPAT, CETN3, DMTF1, UBE2M, RYBP, YTHDC1, PDGFA, ATP2B1, TIA1, RGS3, PRNP, KLF5, CHKA, TMCC1, EPHA2, ELF1, ELF4, THUMPD1, MAFF, ZNF14, SRF, EPAS1, CLK3, ARID5B, KLHL9, POLD3, CENPA, SLC25A12, PTPN3, NPAT, BTAF1, MTMR4, SERPINH1, MCM7, RFC4, HSPA4L, DNAJA1, MCM3, RLF, FBXL5, MTF2, POGZ, BTN2A1, BRD1, FEM1C, BAZ2B, RANBP6, COIL, BACH1, ZNF3, RBM4B, ZNF45, ARID4B, ARHGEF7, CSTF1, CENPC1, NCK1, NFIL3, RPP38, CHD9, ZNF180, ZNF588, ZNF131, CDC42EP2, RNF113A, TLK2, ZNF44, RIC8B, KBTBD2, BAG5, RBM39, ZBTB24, NEDD9, STARD13, SCYL3, ZNF432, SEC31A, INTS6, JMJD1C, TCF21, FOXJ3, NUP153, ZNF217, KIF2A, ZNF195 RIPK2, GTF2E1, ZNF451, PGS1, MYC, NGDN, PNRC2, PRPF3, CRKL, ADNP, MORC3, POLS, ZCCHC8, ZNF274, ZCCHC6, EGR1, JUN, FOS, DDIT3, PMAIP1, NFKBIA, GADD45A, NR4A1, GEM, FOSL1, SLC3A2, EIF1AX, KLF2, GINS2, FHL2, FOSB, RPA1, EZH2, MCM5, RFC3. The defined portion of the toxicity representing genes comprises at least 50% of the toxicity representing genes, preferably at least 75% of the toxicity representing genes, more preferably at least 80%, or at least 85%, or at least 90% or at least 95% of the toxicity representing genes.

The processor is also caused to predict toxicity of the agent based on a percentage of the toxicity representing genes that are significantly differentially expressed in the biological sample as induced by the agent.

In yet another embodiment, the computer program comprises instructions, which when executed by a processor, cause the processor to obtain gene expression data defining differential gene expression of toxicity representing genes in a biological sample induced by the agent. The toxicity representing genes comprise at least one gene regulated by each transcription factor selected from the group consisting of TP53, EP300, CDKN2A, PPARG, HIF1A, RELA, RB1, NR3C1, NFKBIA, ESR1, STAT5A, JUN, STAT3, SP1, SMARCA4, SMAD7, RARB, MYC, JUNB, EGR1, E2F1, CTNNB1, BRCA1, ATF2, RBL1, NFKB1, FOS, E2F3, CREBBO, SRF, NCOR2, HTT, ELK1, CYLD, and CREM.

The processor is also caused to predict toxicity of the agent based on a percentage of the toxicity representing genes that are significantly differentially expressed in the biological sample as induced by the agent.

Probabilistic Modeling to Define the PTGS and/or PTGS Score

Prediction of the toxicity of chemical compounds would be helped by broadly defining gene expression changes that could causally explain why the dose generally makes a chemical into a poison at the cellular and organismal levels. To this effect, the inventors analysed the overlay of the Connectivity Map (CMap) and the NCI-60 DTP Human Tumor Cell Line Screen, including GI50 (50% growth inhibition), TGI (total growth inhibition) and LC50 (50% lethal concentration) measurements in the cancer cell lines MCF7 (breast), PC3 (prostate) and HL60 (leukemia), using a probabilistic modeling approach to generate a predictive toxicogenomics space (PTGS) composed of overlapping components. The PTGS of this invention captures both known and potentially novel toxicity and stress-related transcriptional regulators, as well as a multitude of cytopathological states in cells and internal organs, including liver. The PTGS also outperforms toxicity predictions from quantitative structure-activity relationships (QSAR) analysis, and moreover, serves to score the dose-dependency of chemical treatments of, for example, human hepatocytes. Component modeling of large data sets therefore offers a novel way of predicting dose-dependent toxicity.

Figure 3:
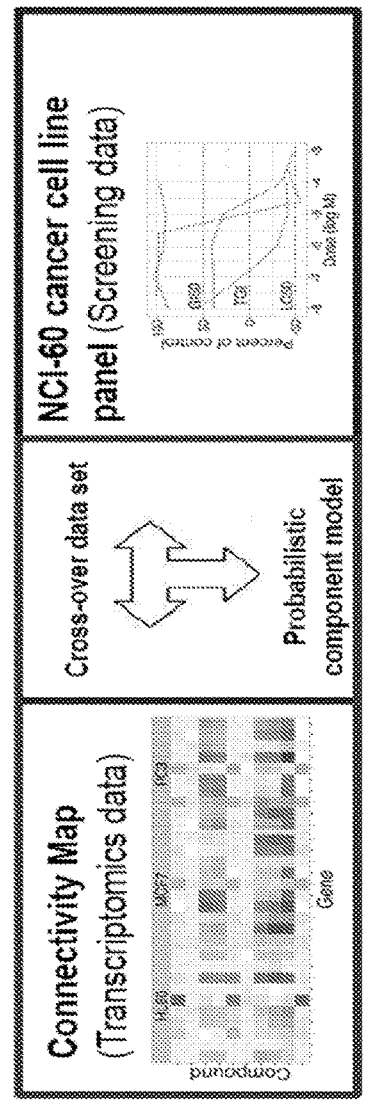
FIG. 3. Results summary for creating the PTGS.
Figure 3:
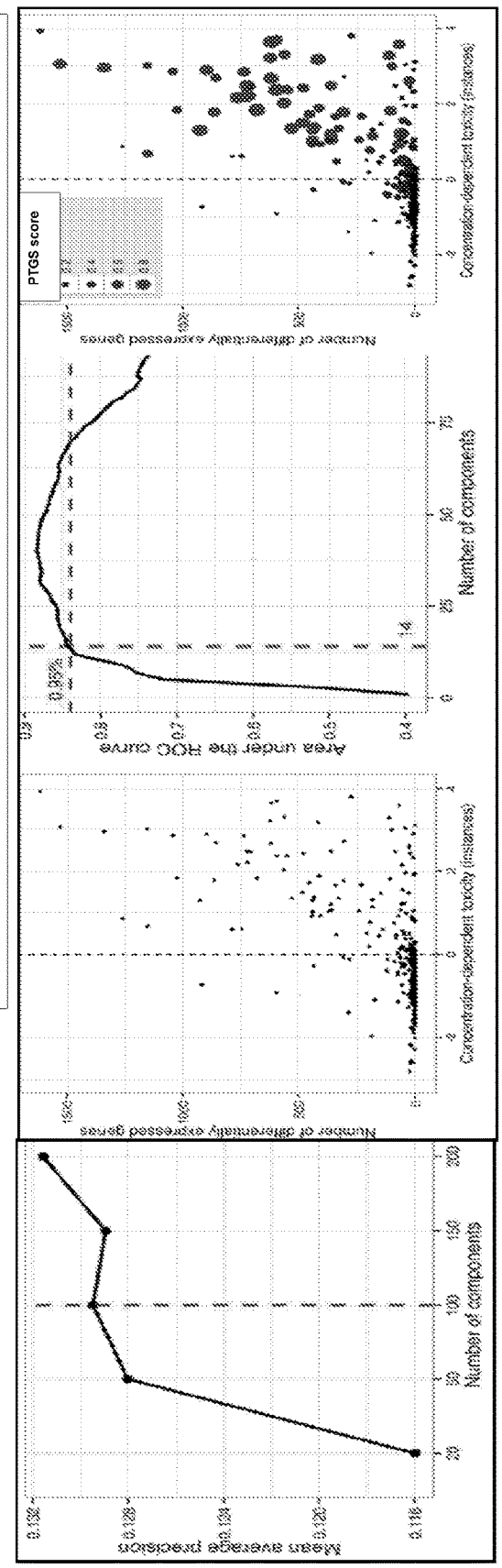
Figure 4:
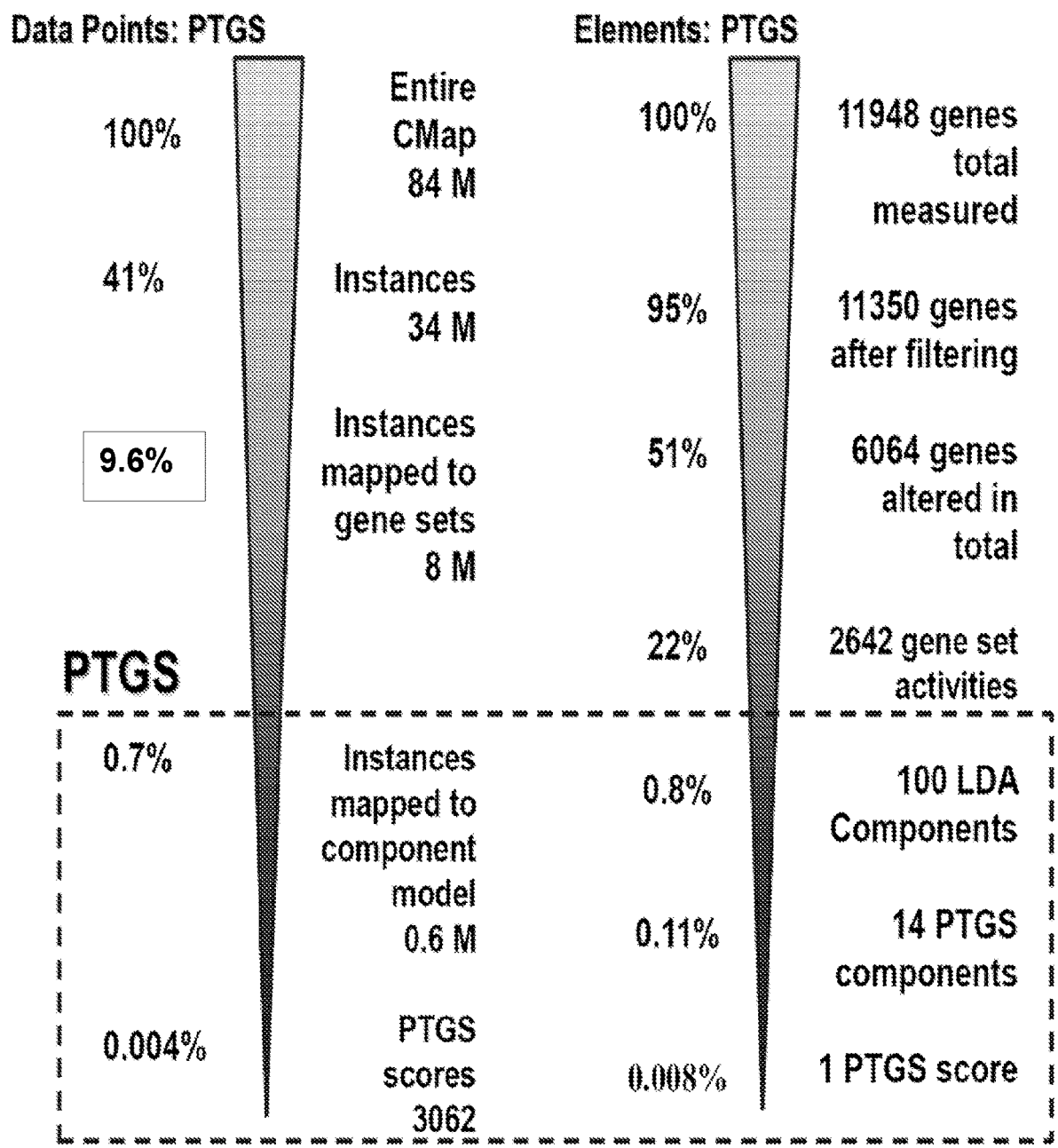
FIG. 4. Numerical details of the data points and elements reduction steps for creating the PTGS. Data points are calculated, in decreasing order of size, from a p-gene, g-gene set or c-component by n-sample matrix. Percentages calculated from the first item in the category; M=1 million data points.
Figure 5:
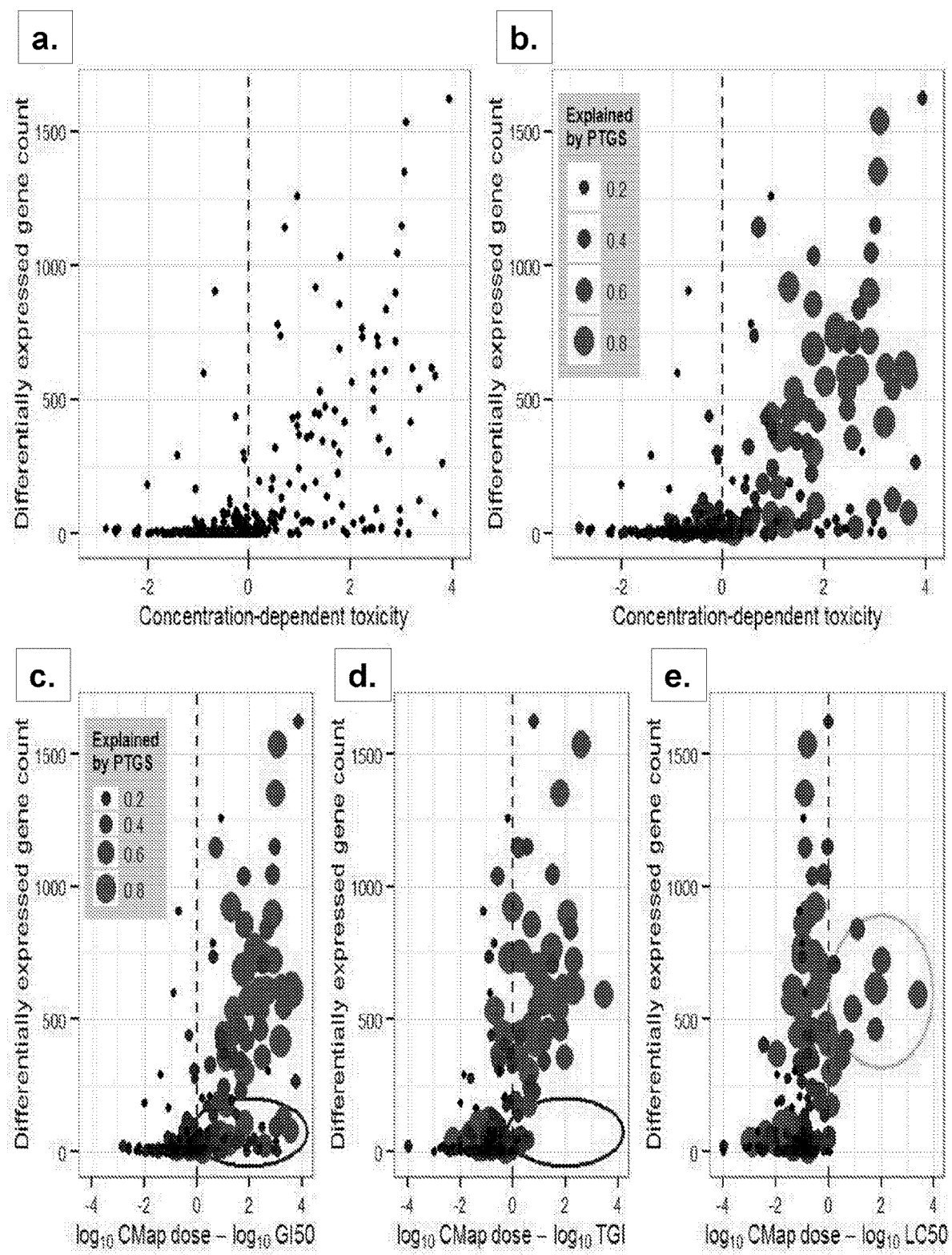
FIGS. 5-9 include the detailed steps at each stage.
Figure 6:
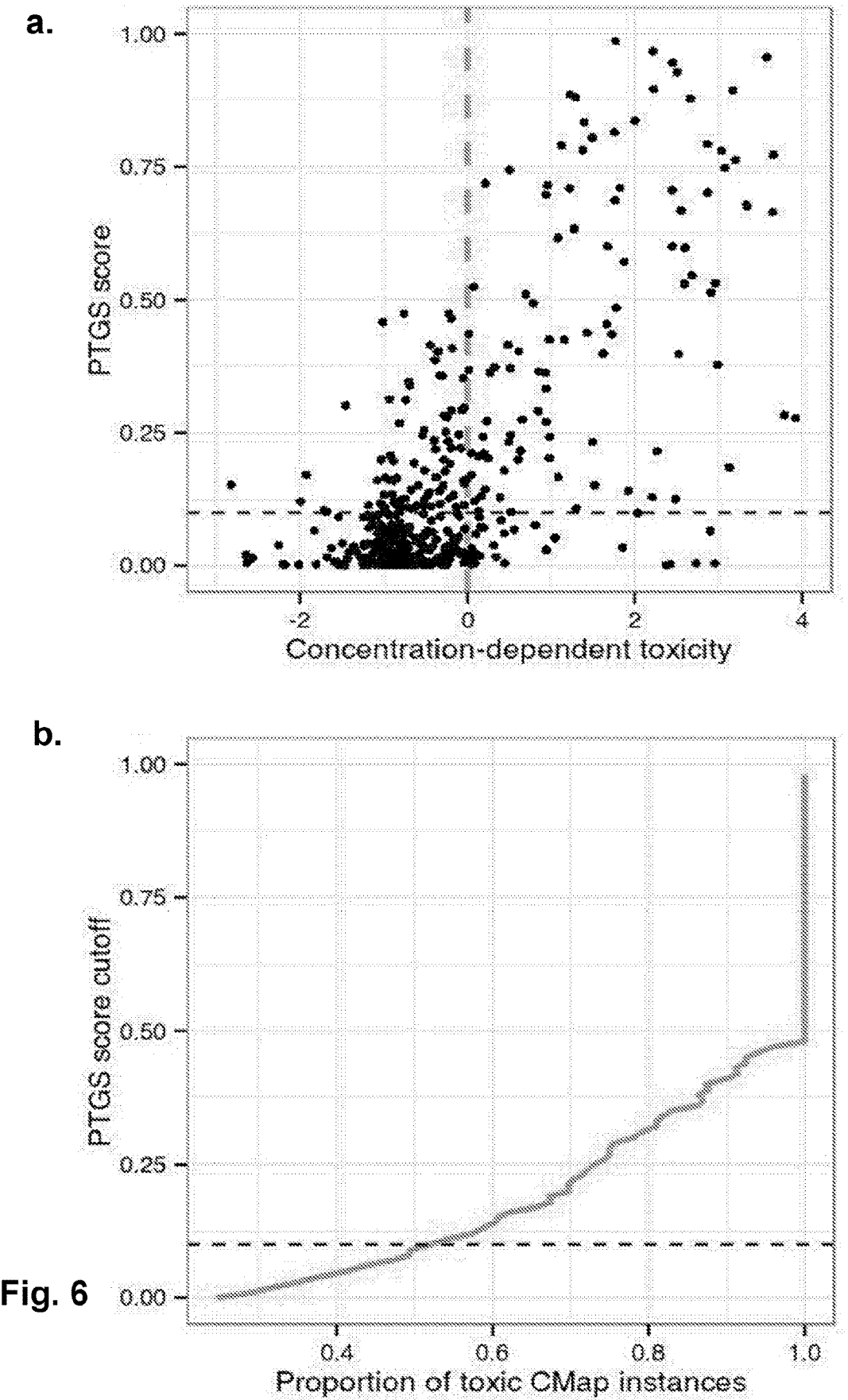
Figure 7:
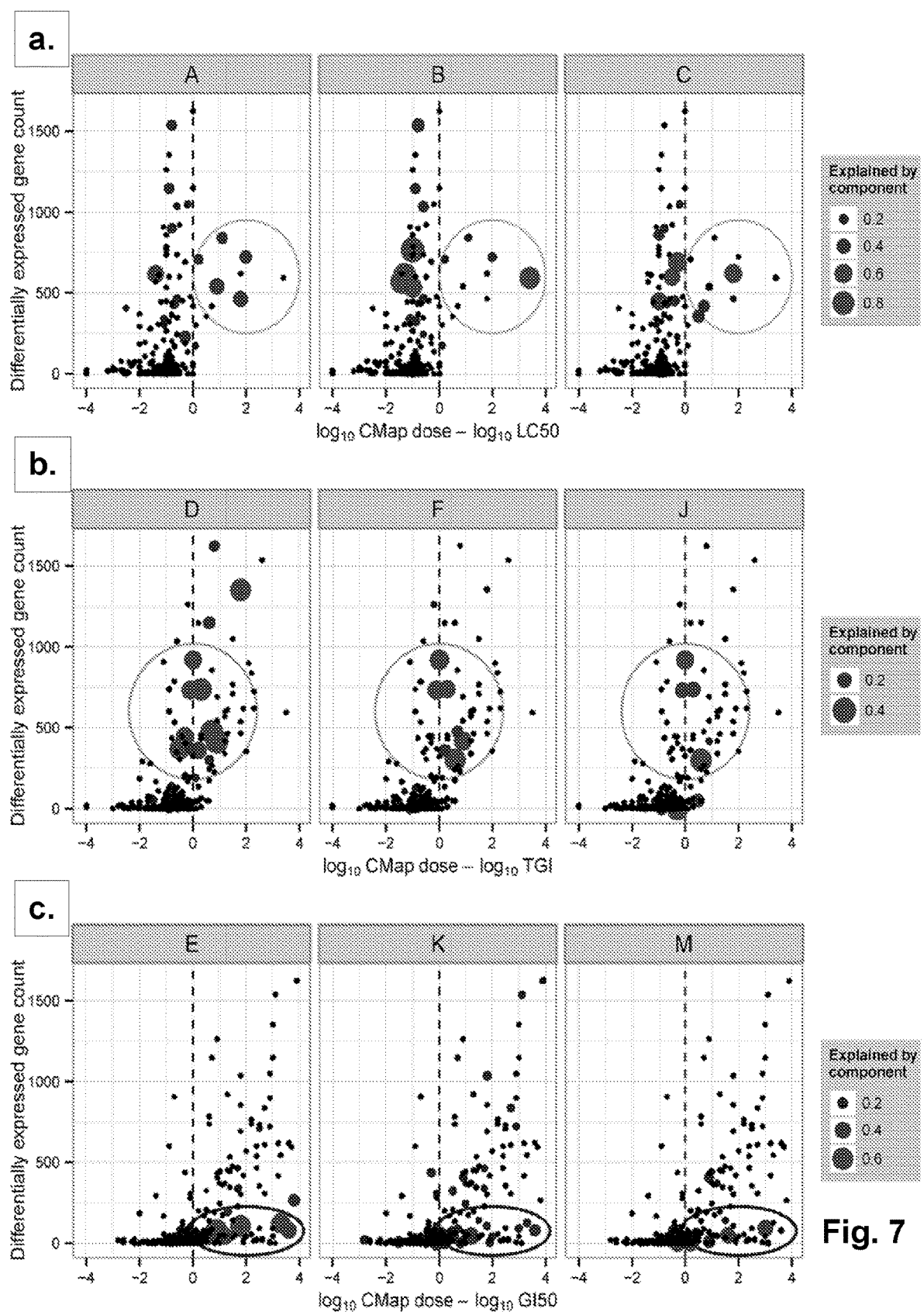

The PTGS score of this invention was defined using probabilistic component modeling of the combined CMap and NCI-60 data, as the minimally sized component space that captured dose-dependent toxicity within the complete data set; FIG. 3 depicts the analysis strategy that generated the PTGS. The protocol extracted and reduced the number of data points, chemicals and genes, providing ultimately combined gene expression and toxicity data coverage for 492 CMap microarray data instances (an instance represents one chemical treatment in one cell line) relative to the toxicity effect of 222 CMap chemicals. Positive concentration-dependent data indicated that the CMap measurement instances had been produced at higher concentration than their GI50 value and therefore reflected a growth-inhibitory and potentially intoxicating response (FIG. 5a, b). Probabilistic component modeling decomposed the entire pre-processed CMap data, consisting of 3062 instances, to 100 partially overlapping components (FIG. 3). Superimposing the NCI-60 data enabled thereafter a selection of an optimally sized set of 14 components for predicting toxicity of the 492 instances (FIG. 3). Most components were proportionally active in all cell lines, while only components B and I showed over-representation for a particular cell line (HL60 and PC3, respectively). Hierarchical clustering of the PTGS revealed clustering of the components into one group comprising a majority of the components, another less distinct cluster, and one outlier component (L), demonstrating that most of the components had overlapping gene activities. Activation of any of the PTGS components indicated dose-dependent toxicity (FIGS. 3 and 5-7). The toxicity effects of the chemicals correlated with the transcriptional variation (Pearson correlation is 0.69; p-value<$2.2*10^{-16}$; FIG. 5a). The 14 components primarily become active at or above the GI50-dose (FIG. 5b). The components covered a wide range of dose-dependent responses. Some CMap instances represented toxicities above the TGI level; such instances tended to have many differentially expressed genes and highly active PTGS components, primarily A-C (FIGS. 5d and 7a). On the other hand, instances belonging to the smaller cluster and especially component E but also K and M tended to be active at around the GI50 growth-inhibitory level and displayed smaller numbers of differentially expressed genes (FIGS. 5c, 5d and 7c). Few instances reflected cell-killing doses (FIG. 5e). To rank chemicals for probability of toxicity, a PTGS score was defined as the sum of the contributions of the 14 components (FIGS. 3, 5). The outcome of the analysis strategy in regards to the alterations of the data points, instances, chemicals, components and genes are shown (FIG. 4). Generation of the predictive model reduced, transformed and decomposed the millions of data points extracted from the CMap to 0.7% of the original data size. Altogether, 11% of the genes (22% of the responsive genes, i.e., 1331 versus 6064 genes) were ultimately connected to toxicity-related transcriptomic changes.

As such, one aspect of the invention is a method of defining a predictive toxicogenomics space (PTGS) comprising the following steps:

1. Pre-processing CMap raw data to select the highest effect instances as follows:

(a) normalizing the data using the RMA method (robust multi-array with R-package aroma;

(b) selecting an abundant microarray platform, e.g., HT-HG-U133A and mapping to Ensembl gene identifiers (custom cdf version 12, http://brainarray.mbni.med.umich.edu/Brainarray/Database/CustomCDF/CDF_download.asp) to decrease low-intensity noise in the data;

(c) reducing the noise in the expression data further by removing 5, 10, 15% etc, preferably 5% of genes displaying the highest variance in control measurements;

(d) computing differential expression as the log 2 ratio between drug treatments and respective control measurements. In the case of multiple controls per batch, a more robust control can be calculated as the mean of the control measurements after first removing, as an outlier, the control with the highest (Euclidean) distance to the other controls; and (e) selecting the highest effect instances. To balance between the varying sample sizes for different compounds in the CMap data, the instance for each compound and cell line with the strongest effect, measured as the highest (Euclidean norm of) response, was selected for further analysis. For 18 compounds with multiple concentrations available, only one instance per concentration value was included. The resulting gene expression data consisted of 3062 treatment instances (compound and cell line pairs), profiles for 1217 distinct compounds in the three cell lines (MCF7, PC3, and HL60, with 1203, 1131, and 728 instances per cell lines, respectively) over 11,350 genes.

2. Transforming instances from genes to gene sets as follows:

(a) firstly by using GSEA (Java software package, version 2-2.05, http://www.broadinstitute.org/gsea) to reduce high dimensionality of data; and (b) secondly, to incorporate prior biological knowledge using the 1321 gene sets of Canononical pathways (Biocarta, KEGG, Reactome) and curated gene sets from the Molecular Signature Database (MSigDB) (C2-curated gene sets v2.5 (http://www.broadinstitute.org/gsea/msigdb)). The false discovery rate q-value (FDRq), which GSEA produces to represent the strength and direction of the gene set activation, was quantised to non-negative integer values with the transformation min(round(−log 2 FDRq))−1, 0), separately for the positively and negatively activated genes in the gene sets, resulting in activation counts for 3062 instances over 2642 gene sets.

3. Performing probabilistic component modeling to define components as follows:

(a) first by applying a Latent Dirichlet allocation (LDA) model to identify transcriptional response patterns from the gene set activation count data, each resulting component associates probabilistically a subset of the treatments with a subset of the gene sets. Each component thus represents a specific chemical-induced response pattern, interpretable based on the associated gene sets; and (b) second, the component count was chosen (from the set 20, 50, 100, 150, 200, to be 100 where the performance stabilized; see FIG. 3) by external validation, to maximize empirical performance in retrieving drugs that share protein targets and fourth level Anatomical Therapeutic Chemical classification codes.

4. Associating toxicological profiles to the transformed CMap data as follows:

(a) first, downloading Toxicological profile data e.g., from the NCI-60 database DTP human tumour cell line screen (http://dtp.nci.nih.gov/docs/cancer/cancer_data.html). This data set has three reported drug response values: GI50 (50% growth inhibition), TGI (total growth inhibition), and LC50 (50% lethal concentration) for 59 different cell lines. The former values have been inferred from measurements covering typically 5 concentration values, most common range being from 10 nM to 100 µM (or from −8 to −4 log 10 M);

(b) second, matching the toxicological profile (NCI-60) data from step (a) with the CMap instances based on the compound names. Additionally, alvespimycin and tanespimycin, named 17-DMAG and 17-AAG in NCI-60, respectively, were added manually. The three drug response values were extracted from NCI-60 data for in total 222 CMap compounds and 492 measurement instances on the three cell lines (MCF7, PC3 and HL60; with 197, 179, and 116 instances per cell line, respectively), averaging over multiple measurements when available.

(c) third, defining concentration-dependent toxicity as the difference of the logarithmic CMap concentration and GI50 values. A positive concentration-dependent value indicates that the CMap measurement instance has been produced at higher concentration than its GI50 value and therefore reflects a growth-inhibitory response interpreted as reflecting toxicity. The concentration-dependent toxicity of zero was therefore used as a rough cut-off to classify the instances in a dose-dependent manner. Histograms of the CMap and NCI-60 endpoint concentration values are shown ed that most CMap instances were obtained around 10 µM, inducing a very high correlation between the concentration-dependent toxicity and intrinsic potency values (Pearson correlation 0.94). As the CMap generally includes one concentration assessment (10 µM), the data was analysed under the a priori assumption that toxicity-related transcriptomic responses are subject to the chemicals' intrinsic potency to cause toxicity. The 100 components produced by probabilistic modeling covered the full space of transcriptional responses caused by the 3062 CMap measurement instances; and (d) fourth, evaluating the components association to toxicity by their ability to predict the concentration-dependent toxicity for the 492 CMap instances with toxicity data. For this, a five-fold cross-validation procedure was repeated ten times. The 100 components were first ranked based on their probability-weighted mean concentration-dependent toxicity values $TOX_z$ over the training instances i. The mean toxicity values were computed as $TOX_z = \Sigma_i [p_n(i|z) \cdot TOX_i]$ wherein the normalized probabilities $p_n(i|z)$ for the training instances i to belong to component z were computed as $$p_n(i|z) = \frac{p(z|i)}{\Sigma_{i'} p(z|i')}.$$

The cumulative concentration-dependent toxicity classification performance over the test instances was then evaluated for the components in the ranked order, providing area under the ROC curve values (AUC) for each component count. The mean AUC values over the repeated cross-validations as a function of the component count were used to select the component number (FIG. 3). The most highly ranked components are strongly associated with toxicity on test data, with AUC peaking at 40 components. To focus on the components with the highest relevance to toxicity, the number of components was chosen where the AUC value reached 95% of the highest value, resulting in a trade-off between interpretability and the highest predictive performance. The resulting top 14 components were chosen to define the Predictive Toxicogenomics Space (PTGS). The top 14 components identified in this invention were labeled from A-N, with component A having the highest probability-weighted mean concentration-dependent toxicity value. The probability of an instance to belong to the PTGS components was used thereafter as a predictive score for its toxicity.

In another aspect of the invention, a method of defining a predictive toxicogenomics space (PTGS) score may comprise using alternative databases and toxicity-associated gene expression profile data, for example, instead of the CMap database, 1000 LINCS landmark genes (http://lincscloud.org/), Drugmatrix, TG-GATE, active genes differentially expressed above 2-fold within the CMap database (6100) and LINCS (Library of Integrated Network based gene signatures) databases could be used for gene expression data. In a further aspect of the invention different version of the MSigDB could be used as sources of signatures (e.g. 1.0, 3.0, 4.0, 5.0) or different parts of the MSigDB, GeneSigDB, the Comparative Toxicogenomics Database, predictive signatures from the DrugMatrix database (ftp://anonftp.niehs.nih.gov/drugmatrix/Differentially-_expressed_gene_lists_directly_from_DrugMatrix/), and combinations of these or other sufficiently comprehensive signature collections. In yet other aspects of the invention, a method of defining a PTGS score may comprise deriving the components, representative of toxicity-induced differential gene expression, using alternative probabilistic modeling approaches (e.g., replacing probabilistic modeling using LDA), for instance, elastic net regression, non-linear regression, Group Factor Analysis (GFA), tensor GFA etc and it can further be demonstrated that the components derived using the former alternative probabilistic modeling approached can behave in the same, or in similar, ways as the components defined in this invention.

Validating the Predictive Toxicogenomics Space (PTGS) Score

Figure 8:
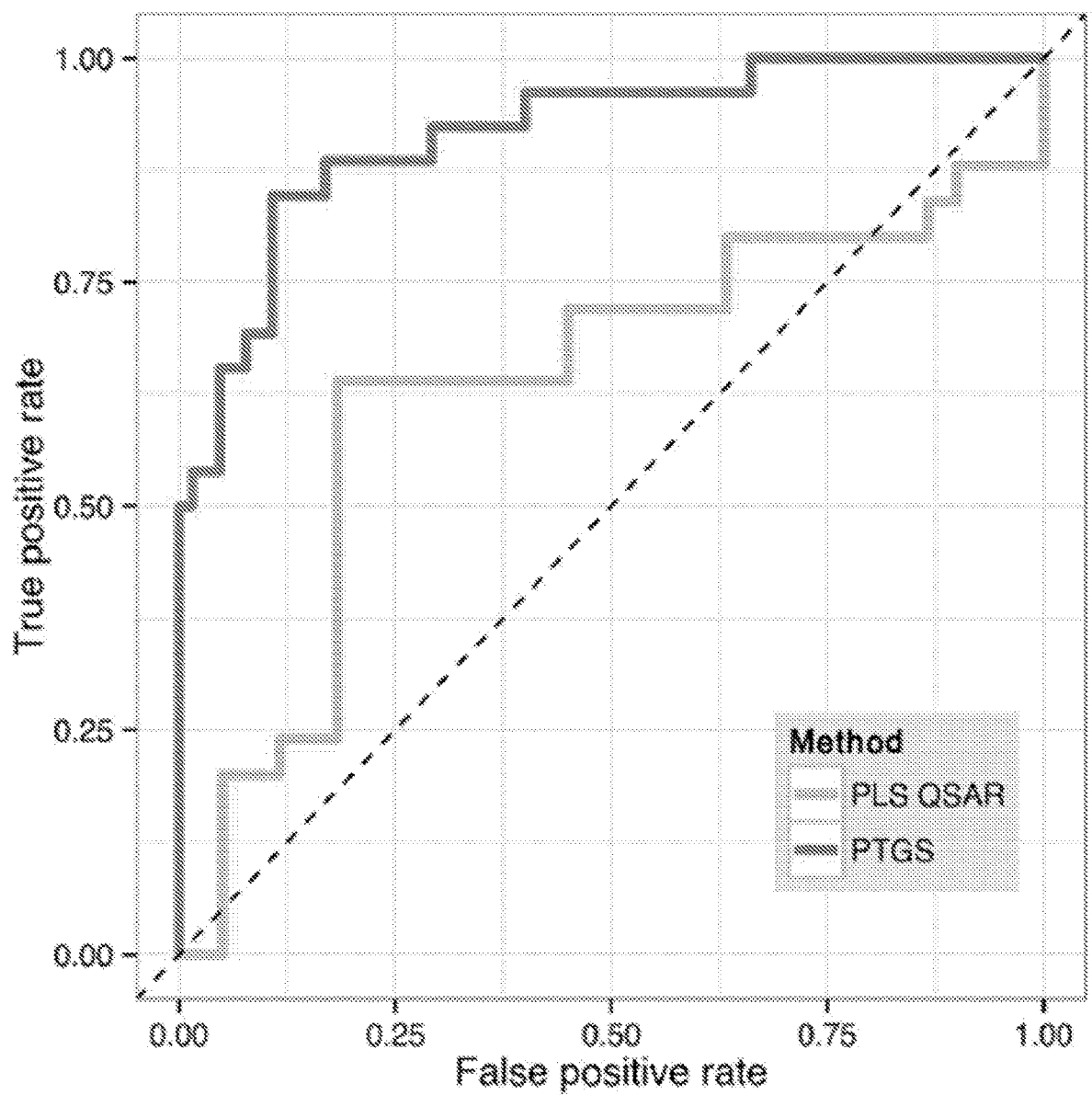

To validate the predictive performance of the PTGS, a set of CMap instances that were not included in the NCI-60 data set were assessed (FIG. 8). Data quality was first verified by replicating the measurements for 36 instances for 16 different compounds already measured in NCI-60. The replicated measurements were well in agreement with the NCI-60 measurements with a Pearson correlation of 0.86. Importantly, the classification of toxic vs. non-toxic was repeated in 32 of 36 instances, and the four instances where this changed had a score close to the cut-off in both data sets. A separate set of data from 16 NCI-60-assessed chemicals also verified the quality of the applied cytotoxicity assay relative to the NCI-60 results. For the actual validation, all the CMap instances without NCI-60 data were ranked based on their PTGS scores. In total 91 instances for 38 unique compounds were then chosen for measurement, including instances from the very top of the list (highest expected toxicity) as well as instances with very low score (controls with expected low toxicity). Assessment of the 38 non-NCI-60-assessed chemicals profiled as part of the CMap for cytotoxicity at concentrations between 10 nM to 100 µM demonstrated a wide range of toxicity effects. The PTGS score predicted the toxicity of the non-NCI-60-assessed chemicals with a high sensitivity and specificity (FIG. 8). The PTGS score of this invention further outperformed data generated from quantitative structure-activity relationships (QSAR) (FIG. 8). QSAR analysis encompassed structures for 201 of the 222 chemicals (448 of the 492 instances). The validation set was based on the experimental validation data, and resulted in 35 structures of the 38 chemicals (85 of the 91 instances). QSAR modeling did not result in models significantly better than random models, and always performed worse than the predictions based on the PTGS components.

To further validate the results of the PTGS described in this invention, in an independent data set, the 'Toxicogenomics Project-Genomics Assisted Toxicity Evaluation system' (TG-GATEs) data set was used, as it constitutes a resource that spans both in vitro and in vivo analyses of 158 hepatotoxic chemicals. These validation analyses demonstrated that the PTGS scores increased with the treatment concentration of the compounds profiled in human hepatocytes within the TG-GATEs toxicogenomics database (783 instances were analyzed), supporting similar dose-dependent gene expression changes in dividing tumor-originating CMap cell lines as in non-dividing normal tissue-originating hepatocytes. Interestingly, drugs withdrawn from market due to unexpected hepatic adverse effects produced strong positive scores, including bendazac, benzbromarone, benziodarone, chlormezanone, iproniazid, moxisylyte, nimesulide and perhexiline. A total of 3 of 20 liver pathological scores (i.e., necrosis, acidophilic change and fibrosis), generated significant positive associations for the PTGS within the TG-GATEs repeated-dose toxicity studies in rats. Decomposing the results to the component level, regularised logistic regression analysis of rat repeated dose liver treatments for up to 28 days using the individual component scores as inputs indicated that the components G, H, N and I (together and in various combinations) are especially prominent among models that successfully predict liver pathology after cross-validation, including acidophilic changes, fibrosis, cellular infiltration, necrosis and swelling.

Therefore, in a one embodiment of the invention the predictive toxicogenomics space (PTGS) score is validated by techniques known to those skilled in the art. Preferably, an external dataset to the model building data set is used (e.g. data external to the CMap).

Characterizing PTGS-Component Derived (A-N) Genes and PTGS-Associated Genes

To assess the mechanisms and modes-of-action ascribed to the PTGS, the 14 overlapping components were annotated with the most active genes for each component, 1331 genes in total (PTGS_ALL). As expected, these genes showed enrichment for a variety of basic biological and metabolic processes known to be associated to growth inhibition, cellular toxicity and stress response pathways. Further analysis pointed to 35 transcription factors regulating the genes within the components. Generally the components within the most prominent PTGS cluster enriched for TP53, NR3C1, RELA, NFKBIA, HIF1A and STAT3 regulatory factors, and inflammation-related gene ontology categories, such as toll-like receptor signaling pathways, as well as stress from DNA damage and reactive oxygen. Components E and K enriched cell cycle and cell division related categories, e.g., S phase of mitotic cell cycle and DNA strand elongation involved in DNA replication, as well as related regulators including MYC, CDKN2A, RB1 and E2F1. Of all the regulators, P53, EP300 and CDKN2A were associated with the largest numbers of components.

The gene set overlap analysis using Fishers exact test and a database of toxicity related gene signatures (Ingenuity Pathway Analysis software toxLists) indicated enrichment for pathological changes in major internal organs typically associated with adverse drug reactions and those seen in repeated-dose toxicity studies of laboratory animals. Genes associated with components A-C enriched most strongly for liver necrosis/cell death, renal necrosis/cell death and PPARa/RXRa activation, whereas components E and K enriched for G1/S checkpoint regulation, aryl hydrocarbon receptor signaling and p53 signaling. Various components in the large cluster also enriched for cardiac and hepatic fibrosis, including component G. Some components enriched for particular structural and functional classes among the CMap compounds, e.g., components A-C enriched protein synthesis inhibitors and cardenolide glycosides, components E and K enriched HSP90 inhibitors, and components D and F for DNA topoisomerase inhibitors. Although without marked component-association, 199 genes had strong PTGS-association, e.g. the PTGS-associated genes (PTGS_core). In support of this component-driven approach, the majority of enrichment from this gene set were recovered from individual components, and the component-level enrichment analysis produced overall higher significance p-values.

As such, one aspect of the invention is a method of defining predictive toxicogenomics space (PTGS) score, including PTGS-component derived and PTGS-associated genes, comprising the following steps:

1. Pre-processing CMap raw data to select the highest effect instances as previously described herein and comprising the sub-steps:
   (a) normalizing the data using the RMA method);
   (b) selecting an abundant microarray platform and mapping to Ensembl gene identifiers;
   (c) reducing the noise in the expression data;
   (d) computing differential expression;
   (e) selecting the highest effect instances.

2. Transforming instances from genes to gene sets as previously described herein and comprising the sub-steps:
   (a) firstly by using GSEA;
   (b) secondly, to incorporate prior biological knowledge using the 1321 gene sets of Canononical pathways and curated gene sets from the Molecular Signature Database (MSigDB).

3. Performing probabilistic component modeling to define components as previously described herein and comprising the sub-steps:
   (a) first by applying a Latent Dirichlet allocation (LDA) model;
   (b) second, the component count was chosen by external validation.

4. Associating toxicological profiles to the transformed CMap data as previously described herein and comprising the sub-steps:
   (a) first, downloading Toxicological profile data;
   (b) second, matching the toxicological profile (NCI-60) data from step (a) with the CMap instances based on the compound names;
   (c) third, defining concentration-dependent toxicity;
   (d) fourth, evaluating the components association to toxicity.

5. Elucidating PTGS-component derived and PTGS-associated genes as follows:
   (a) choosing the most active sets of instances and genes (where the top instances have the largest p(instance|component), thresholding at cumulative probability reaching 0.2).

For all genes included in the top gene sets, evaluating their differential expression with a standard two-sided t-test and generating a list of PTGS-associated genes based on t-test p-value cut-off value of 0.01, after Bonferroni correction for multiple testing. The identified 199 genes strongly associated to the PTGS in general, but not with particular components and;

(b) characterizing genes of individual components from a total of 1331 of the most active genes, as indicated by the p-values. For this analysis, and considering that Bonferroni correction would be too conservative, a ranked list of genes thresholded at the 0.01 level was generated, assuming that the higher a gene is on the list, the more evidence there is for it being informative in characterizing the component. The gene lists for the 14 components (A-N) and the PTGS overall set are described in this invention.

(c) performing enrichment analysis on the component associated genes identified in (b) using Ingenuity Pathway Analysis (IPA, application version 220217, content version 16542223) and Gene Ontology (GO) (R package topGO39, version 2.12.0). The enrichment results were thresholded at p-value 0.001, and at least three genes were required to be annotated to each GO category, IPA toxList or IPA regulator providing 38 toxicological functions, and 62 Biological Processes. The IPA upstream regulator analysis results were further filtered to include regulators that were enriched in the overall gene set of 199 genes (PTGS_Core) identified in (a) as well as in at least one of the components and that were connected to other regulators via a mechanistic network (Krämer et al. 2014) (to give further evidence of a genuine regulatory relationship). Furthermore since the overall gene set did not cover all biological functions, as indicated by the GO enrichment analysis and the other analyses, highly enriched regulators (p-value<10-5) that occurred in at least one third of the components were included, giving a total of 35 upstream regulators.

Methods of Predicting Toxicological Effects Using the PTGS Score

One aspect of the invention comprises of the following steps:

1. The invention is based on a new strategy of modeling and new aid for efficient relevance analysis, in a data-driven way, all the reproducibly identifiable responses in a data set consisting of gene expression profiles of a large collection chemicals or drugs in a number of cellular model systems. A subset of toxicity associated component models is selected using the invention herein by calculating activity-weighted mean concentration-dependent toxicity values of the all models by integrating with a database of matching toxicities. A Predictive Toxicogenomics Space (PTGS) score is produced by integrating the activities of all toxicity associated component models.

2. Disclosed herein are the methods for generating a set of toxicity-predictive probabilistic models and of using such a collection to establish a toxicity predictive PTGS score.

3. Comparing the PTGS score of the test substance with a database of PTGS scores associated with toxicity values establishes a threshold for safe levels of the compound when toxicity-predictive component-models are not perturbed at the concentration of the test substance. The PTGS score is thus in the invention herein utilized as an in vitro TTC score, involving also the application of a safety margin for exposure to the organism level.

4. Computer program product having a plurality of instructions stored thereon which, when executed by a computer processor, cause that computer processor to a) compute activities of the component models and the PTGS score, said model activities for the concentration of the test substance having been generated by performing one or more assays that measure genome-wide or equivalent gene expression profiles; and b) determine whether the PTGS score of the test substance exceeds the threshold at the specified concentration.

In one preferred embodiment of the invention a single Predictive Toxicogenomics Space (PTGS) score is derived based on analyzing the CMap dataset. Modeling formalism referred to as probabilistic component modeling, for example Latent Dirichlet Allocation (LDA), is used to derive 100 components that probabilistically describe the cellular changes caused by exposure to 1217 chemicals (see FIGS. 1-3).

In one embodiment of the invention a single PTGS score is derived based on analyzing the CMap dataset (see FIGS. 1-4). Modeling formalism referred to as Latent Dirichlet Allocation (LDA) is used to derive 100 partially overlapping components that probabilistically describe the cellular changes caused by exposure to 1217 chemicals profiled using MCF7, PC-3 and HL60 cell lines. Data reduction starts with the 84 million data points that make up the unprocessed CMap (100%), proceeds via a filtering/normalization step (41%), to mapping of gene activities to gene set activities (9.5%) to the LDA model which is 0.7% size of the original data (FIG. 4). Toxicity values (GI50, TGI and LC50) for 222 compounds and 492 distinct measurements from the NCI-60 DTP panel are used to define 14 PTGS components that are activated when a cell becomes intoxicated. Mechanistic interpretation of the PTGS components associates them to various biological pathways, transcriptional regulators and toxicity related biomarker signatures, implying that individual component activities enable risk assessment strategies based on toxicity pathways or Adverse Outcome Pathways (AOP). The PTGS score is calculated as the sum of the activities over the 14 components; and therefore reflects the plurality of mechanisms that lead to toxicity. Threshold for the PTGS score is set at the level where 50% of the measurements reach the GI50 half-maximal growth inhibitory concentration. PTGS scores predict toxicity from 38 untested CMap compounds better than state-of-the-art quantitative structure-activity relationship models. Furthermore, PTGS scores from 152 chemicals (2605 measurements in total) tested in human hepatocytes from the TG-GATEs dataset correlate with the dose-level of the chemical and PTGS scores from repeated dose studies in rats correlate with necrosis and fibrotic changes in the liver. Therefore predictive models developed using metabolically limited but data rich cellular models (e.g., the CMap) can be applied to evaluate results from metabolically competent models, which tend to be difficult to use for mechanistic in vitro studies.

An additional aspect of the invention is the "PTGS-component derived" method of predicting toxicity of a test compound by calculating a PTGS score comprising the following steps:

Normalizing gene expression data to remove systematic variation;

Calculating fold-change values ($\log 2_{Treatment} - \log 2_{Control}$);

Performing Gene Set Enrichment Analysis (GSEA) for the MSigDB database (v.2.5); using the Broad Institute GSEA tool;

Estimating the activities (probabilities) for all 100 components identified in this invention from the gene sets using Gibbs sampling; probabilities are based on the CMap-derived PTGS model;

Normalizing the sum of all component probabilities to 1 and;

Summing up probabilities of the 14 PTGS components, thereby calculating the PTGS score.

In an embodiment, the PTGS-component derived method tests the hypothesis that the PTGS components are more active than the non-PTGS-associated components following exposure to a test agent at a particular concentration or range of concentrations.

In an embodiment, the PTGS-component derived method requires gene expression data from genome-wide gene expression profiles (e.g., transcriptome-wide measurement technologies can include RNA-seq, microarray etc, or emerging high-throughput transcriptomics technologies such as nanostring, LINCS, Ampli-RNA seq etc) or from a defined number of genes representative of the entire genome, e.g., using LINCS 1000 technology.

In an embodiment, the PTGS-component derived method is used, preferably, for analysing the modes-of-action (MoA) for: 1) biomarker discovery related to Adverse Outcome Pathways (AOPs); and 2) read-across/grouping/categorization of chemicals.

In an embodiment, the PTGS-component derived analysis enables grouping of chemicals into mechanistically similar classes by component activity (in vitro or in vivo data) for read-across assessment of toxicity. The former could include, for instance, assessing a TTC score whereby, preferably, in vitro omics data is used to reduce the uncertainty and hence the assessment factor linked with a TTC-type toxicity assessment, or to establish, using the toxicity pathway approach (e.g., demonstrated with PTGS_TP53 in example 5) in combination with read-across, whether a chemical is likely to be causative of cancer.

Still another aspect of the invention is a PTGS-associated gene-based method of predicting toxicity of a test compound comprising the following steps:

Normalizing the gene expression data to remove systematic variation;

Fitting treatments and controls to a linear model using R/Bioconductor limma package;

Calculating activities of the PTGS-component derived gene sets of components A-N and the PTGS-associated (PTGS_ALL) gene set with all of the genes, applying the limma MROAST Gene Set Analysis (GSA) tool (where the GSA tool derives significance to reject the self-contained null hypothesis that genes in the gene set do not have any association with the subject condition i.e., no gene in the set is differentially expressed; depending on the test statistic usually meaning that 25% or less of the genes in the set are not differentially expressed). Using the most sensitive GSA result for LOEL (Lowest Observable Effect Level) calculation and PTGS_ALL to predict GI50 level of activation. Employ sets of components A-N as positive controls (the majority of these components should be active if PTGS_ALL is active).

In an embodiment, the PTGS-associated gene-based method tests the hypothesis that the PTGS-associated genes are more active in the treated versus control following exposure to a test agent at a particular concentration or range of concentrations, irrespective of whether other genes or gene sets are also active and where the activation (significant differential expression above the noise level of the experiment) of at least 25% of the toxicity representing genes of this invention can be used to predict at least one toxic effect of a test agent.

In an embodiment, the PTGS-associated gene-based method can be applied from the use of PTGS-component derived or PTGS-associated gene expression profiles only, for instance from component derived (A-N) genes (PTGS_ALL (a total of 1331 genes), as opposed to genome wide gene expression data.

In an embodiment, the PTGS-associated gene-based method can be applied from the use of PTGS-component derived or PTGS-associated gene expression profiles only, for instance, from component derived (G, H, N and I) genes to predict liver in vivo and in vitro toxicity (as described in examples 4 and 6).

In an embodiment, the PTGS-associated gene-based method can be applied from the use of PTGS-component derived or PTGS-associated gene expression profiles only, for instance, from component derived (E and K) genes to predict associations to cell cycle regulation (as described in examples 4).

In an embodiment, the PTGS-associated gene-based method can be applied from the use of PTGS-component derived or PTGS-associated gene expression profiles only, for instance, from component derived (N and I) genes as early biomarkers to predict overall toxicity due to the high sensitivity (as described in example 5).

In an embodiment, calculating activities of the PTGS-component derived gene sets of components A-N and the PTGS-associated (PTGS_ALL) gene set with a single sample GSA tools such as the R/Bioconductor Gene Set Variation Analysis tool (GSVA) (where the tool derives the significance to reject the hypothesis that the genes in the gene set do not have stronger association with the subject condition than other genes not in the set). Conceptually, GSVA transforms a p-gene by n-sample gene expression matrix into a g-gene set by n-sample pathway enrichment matrix. This facilitates many forms of statistical analysis in the 'space' of pathways rather than genes, providing a higher level of interpretability.

In one preferred aspect of the method R/Bioconductor limma package is used to fit an experiment-specific linear model to the data and then given a microarray linear model fit, compute moderated t-statistics, moderated F-statistic, and log-odds of differential expression by empirical Bayes moderation of the standard errors towards a common value, where by the moderated t-statistic is used to calculate statistical significance of rejecting the null hypothesis that the gene set is not more active in treatment than in control biological samples. Using the most sensitive GSA result for LOEL (Lowest Observable Effect Level) calculation and PTGS_ALL to predict GI50 level of activation. Employ sets of components A-N as positive controls (the majority of these components should be active if PTGS_ALL is active).

In an embodiment, calculating activities of the PTGS-component derived gene sets of components A-N and the PTGS-associated (PTGS_ALL) gene set with all of the genes, applying a competitive gene set testing tool such as the R/Bioconductor limma ROtation testing using MEan Ranks (ROMER) gene set analysis tool (where the tool derives the significance to reject the hypothesis that the genes in the gene set do not have stronger association with the subject condition than other genes not in the set). In order to derive the statistical significance of the GSVA. Using the most sensitive GSA result for LOEL (Lowest Observable Effect Level) calculation and PTGS_ALL to predict GI50 level of activation. Employ sets of components A-N as positive controls (the majority of these components should be active if PTGS_ALL is active).

In an embodiment, the PTGS-associated gene-based method is preferably used for dose-response analysis (since it reflects toxicity-associated genes) and therefore is suitable for calculating LOEL (Lowest Observable Effect Level), BMD (Bench Mark Dose) and BPAC (Biological Pathway Activating Concentration) values. The PTGS-associated gene-based method is also suited to assessing severity grade of toxic and pathological effects, in in vitro and in vivo models.

In an embodiment of the PTGS-associated gene-based method Bench Mark dose (BMD) and BMDL calculations are carried out preferably using the PTGS-associated gene-based method approach: 1) Single sample gene set enrichment analysis (ssGSEA) is used to derive for each PTGS component and each biological replicate measurement in the study an enrichment factor. In a preferred embodiment of the method the R/Bioconductor package GSVA (Gene Set Variation Analysis) was carried out. Conceptually, GSVA transforms a p-gene by n-sample gene expression matrix into a g-gene set by n-sample pathway enrichment matrix. This facilitates many forms of statistical analysis in the 'space' of pathways rather than genes, providing a higher level of interpretability (Hänzelmann et al. 2013). 2) Each measurement is then compared to their respective control to derive a quasi-fold-change as a gene set score: GSVAscore=GSVAtreat−GSVAcont.

In an embodiment of the PTGS-associated gene-based method for each distinctive treatment the sample number, mean and standard deviation in GSVAscore is obtained by standard statistical methods.

In an embodiment of the PTGS-associated gene-based method the a limma linear model is fitted (referred to as "fit") to the g-gene set by n-sample pathway enrichment matrix, moderated t-statistics are calculated for each comparison (or contrast in limma terminology) and quasi fold-change values (referred to as coefficients by limma) are obtained, number of samples is obtained as above and standard error by se=sqrt(fit\$s2.post)*fit\$stdev.unscaled (this is used to derive standard deviation by the EPA BMDS software).

An embodiment of the PTGS-associated gene-based method uses e.g., the EPA Bench Mark Dose software as instructed in user documentation (BMDS Wizard v1.10-continuousStDev.xlsm is used in this example) and following instructions (e.g., European Food Safety Authority; 2011. EN-113. Available online: www.efsa.europa.eu) the BMD and BMDL concentrations are calculated from models recommended by the software. 4) The analysis is repeated for all PTGS components and the best supported component with lowest BMDL is selected as the endpoint for defining the Reference Point (RP).

In an embodiment of the invention, alternatively, Bench Mark Dose calculations can be performed using the PTGS-component derived approach: 1) For each biological replicate calculate log 2-fold-changes separately, 2) Calculate for each measurement GSEA-profile using the Broad Institute tool (utilizing the MSigDB version 2.5), 3) Calculate from the PTGS model component activities for the 100 components, 4) Using Gibbs sampling estimate component activities from the CMap-derived model, 5) Normalize component activities to 1: component=component/sum(all components), 6) Calculate PTGS scores for all replicates by summing up the normalized activities of the PTGS components, 7) Use a regulatory-toxicology software to estimate Bench Mark Dose (and BMDL) and dose response models for the PTGS score e.g., with US ePA BMDS software or the R/PROASTpackage, to obtain the Reference Point dose as the BMDL value.

In a preferred embodiment of the invention, the PTGS-component derived method and the PTGS-associated gene-based methods (as described above) are combined and/or performed sequentially (see FIG. 9) to determine toxicity of an agent, following exposure of at least one biological sample, such as cell or tissue, by the agent (over a range of concentrations), by deriving; a PTGS score, a virtual GI50 score, dose-response assessment (such as LOEL, BMD and BPAC values), inferring a test agents' concentration-dependent modes-of-action (MoA) for AOP (Adverse Outcome Pathway)-based risk assessment etc. Combined, the PTGS-component derived and PTGS-associated gene-based approaches enable more sensitive and specific in vivo toxicity prediction, i.e., from gene expression profiles of, for example, rat liver (e.g., acidophilic changes, fibrosis, necrosis), mechanistic analysis and prediction of Drug Induced liver Injury (DILI).

In an embodiment of the invention, the combined workflow (see FIG. 9) is used to calculate: 1) A virtual GI50 estimation and LOEL/NOEL estimation using the PTGS-associated genes approach (combined workflow results 1-1 and 1-2), 2) Defining modes-of-action using the PTGS-component derived method (combined workflow result 2) and 3) the Bench Mark Dose (BMD) and BMDL with the PTGS-associated gene-based approach (combined workflow result 3). The combined workflow results 1-1 and 1-2 are derived as follows: 1) Normalize data to remove systematic variation. 2) Fit treatments and controls to a linear model using R/Bioconductor limma package to calculate the gene set analysis test statistics (limma/eBayes moderated t-statistic; Ritchie et al. 2015). 3) Calculate activities of the PTGS-component derived gene sets and the PTGS_ALL gene set (which contains all of the PTGS-associated genes), applying the R/Bioconductor limma ROtation testing using MEan Ranks (ROMER) gene set analysis tool (Ritchie 2015) 4) Use the most sensitive GSA result for LOEL calculation and PTGS_ALL to predict GI50 level of activation. The combined workflow result 2 is derived as follows: 1) Starting from normalized data log 2 fold-change values is determined using the R/Bioconductor limma package, taking into account the study's experimental design and weighing treatments according to estimates relative quality for each array. 2) GSEA is run on the differential expression vector and the output was quantised, as for the CMap data. 3) The p(component|instance)-distribution for the component model is estimated using 100 Gibbs sampler iterations for each treatment sample using the p(gene set|component) probabilities learned from the CMap data to calculate individual component activities. 4) Unlike when calculating the PTGS scores, non-normalized component activities are used in order to visualize the activity levels of the component-associated mechanisms more directly, irrespective of the activity levels of the other components. The combined workflow result 3 is derived as follows: Bench Mark Dose calculations using the PTGS-associated genes approach: 1) Single sample gene set enrichment analysis (ssGSEA) is used to derive for each PTGS component and each biological replicate measurement in the study an enrichment factor. As an example the use of the R/Bioconductor package GSVA (Gene Set Variation Analysis) can be utilized. 2) Each measurement is then compared to their respective control to derive a quasi-fold-change as a gene set score: GSVAscore=GSVAtreat−GSVAcont. 3) For each distinctive treatment the sample number, mean and standard deviation in GSVAscore is obtained. 3) Using e.g., the EPA Bench Mark Dose software as instructed in user documentation (BMDS Wizard v1.10-continuousStDev.xlsm is used in this example) and following instructions (e.g., European Food Safety Authority; 2011. EN-113. Available online: www.efsa.europa.eu) the BMD and BMDL concentrations are calculated from models recommended by the software. 4) The analysis is repeated for all PTGS components and the best supported component is selected as the endpoint for defining the Reference Point (RP).

In another preferred embodiment of the invention, the PTGS-component derived method and the PTGS-associated gene-based methods (as described above) are combined and/or performed sequentially to predict drug induced liver injury (DILI) of a test compound, following exposure of at least one hepatocyte or liver tissue to the test compound (over a range of concentrations).

In yet another embodiment of the invention, a PTGS-AOP conceptual framework workflow is utilized for integrated toxicity assessment (FIG. 17). The PTGS invention overall serves as an omics-based adverse outcome pathway (AOP) framework (PTGS-AOP). Thus the combined toxicity predictive workflow (FIG. 9) enables a "21st Century Toxicology-inspired" pathway-based risk assessment to be carried out using gene expression omics data. Since the workflow is using PTGS to elucidate Adverse Outcome Pathway (AOP)-based toxicity pathway activations (e.g., TP53 pathway activity; example 5) while operating within a space of genes and processes that are toxicity predictive, this approach can be termed and defines the PTGS-AOP conceptual framework. This concept, as defined in the example 5 and elaborated in examples 1-4 and 6, is used to match results derived from omics profiles to Adverse Outcome Pathways (AOPs) by using PTGS components as Key Events (KE), correlated through KE relationships (KER) to Adverse Outcomes (AO). PTGS can be employed in combination with AOPs defined e.g., in the AOP Knowledge Base (AOP-KB), by substituting as evidence PTGS-component derived results where they occur in e.g., AOP-KB schemata. Results that can be substituted include liver pathology-related AOs (example 4 and 6) along with use of PTGS for virtual GI50 estimation, LOEL/NOEL, BMDL and for dose-dependent elucidation of PTGS-coupled transcription factor mediated toxicity pathways (e.g., TP53-mediated) in examples 1-5. Examples of the PTGS and the concept being applied as workflows are detailed in FIGS. 9 and 17.

The PTGS-AOP conceptual framework is advantageously applied as a contract service for predicting safety of customer test compounds from omics profiles (FIG. 17) under the aegis of the European Chemicals Agency (EChA) advocated flexible and extensible 'conceptual framework' coupled with reproducible science as a basis for rational combination of information derived from new predictive tools and existing evidence. The PTGS-AOP conceptual framework can serve to build up a WoE-enriched Integrated Approach to Testing and Assessment (IATA), with rules detailed in Registration Evaluation and Authorization of Chemicals (REACH) Annexes VII-X (column 2) and XI. Use of PTGS improves on mainly structure-based methods for read-across by implementing more advanced and toxicity-specific methods giving higher weight to expression of toxicity-related pathways and biological processes. Making the PTGS-based product(s) available in, for example, a cloud platform reduces the burden of procuring and maintaining an IT hardware infrastructure; the costs are easy to quantify and manage, and will enable to scale resources based on planning and demand. The workflow can be used either wholly, or in part, according to the customers' needs. Possible levels in analysis include, for example, (also see FIG. 17): A) that a customer submits a profile for analysis, e.g., generated either by the customer directly or in partnership with a contract research laboratory, or other service providers that can generate gene expression data. Data quality control, pre-processing, normalization and basic bioinformatics is carried out to identify, minimally, differentially expressed genes and pathways; B) in order to facilitate reliable data analysis the raw and normalized data, metadata and protocols can be described according to emerging regulatory standards (e.g., ISA-Tab); C) preferably, that both the PTGS-component derived and the PTGS-associated gene-based workflows are run to derive overall and individual component activities (details FIG. 9); D) in addition to the results from the workflows covered by step C above, component-level results (PTGS-component derived or PTGS-associated gene-based result-2) are used for read-across versus toxicogenomics databases with pre-calculated component activities according to the protocols of this invention. Read-across uses in this case correlation measures (e.g., Pearson correlation) for ranking compounds according to similarity profiles of toxicity-related components (details FIG. 9); E) the concept enables matching of the results to Adverse Outcome Pathways (AOPs) by using PTGS components as Key Events (KE) correlated through established KE relationships (KER) to Adverse Outcomes (AO). Relationships to liver pathology-related AOs have been demonstrated (FIGS. 15-16) and F) the toxicity evaluation to support decision making further includes: 1) a PTGS-based virtual GI50 score applicable to toxicity estimation and ranking (FIG. 5-6, 10); 2) analysis of in vivo pathology based on in vitro data e.g., rat liver pathology and human DILI estimation (FIGS. 15-16); 3) supporting threshold of toxicological concern rating with in vitro data (FIGS. 5-8; 10); 4) dose-response estimation including deriving NOEL/LOEL (FIGS. 10-12); 5) Mechanistic analysis using pathway-based methods applying the PTGS components (FIG. 13); 6) biological similarity estimation e.g., for grouping/read across between compounds (Example 4) and 7) ab initio toxicity prediction of compounds based on the PTGS-AOPs conceptual framework (FIG. 5-6, 9-16). Parts A, C and D as described above can be fully automated as part of a toxicity evaluating computer system, B requires at least semi-supervised human curation, part E can be also fully automated, but benefits from human evaluation. In part F, a toxicity report can be generated in a fully automated way for expert evaluation of the results (e.g., for evaluating DILI potential of drugs under development or for regulatory decision making on chemical safety).

Overall, the composite analysis in this invention surprisingly suggested that the PTGS performs well in predicting dose-dependent effects across several cell types and toxicity endpoints. The complete component set reflects a broad collection of compounds with different modes of action, and therefore, plausibly represents a multitude of toxicity mechanisms. Thus, the data-driven modeling approach taken in this invention likely served to remove or minimize gene expression changes that related to the pharmacological (non-intoxicating) actions of the drugs tested in the CMap. Different to the common belief that biological responses to chemicals are determined by many undefined interactions with cellular components and processes, the results indicate that overall a relatively limited set of gene-activity components or pathways might account for cellular toxicity reactions.

Generating Gene Expression Data and/or Nucleic Acid Hybridization Data

Any assay format to detect gene expression may be used to produce nucleic acid hybridization data. For example, traditional Northern blotting, dot or slot blot, nuclease protection, primer directed amplification, RT-PCR, semi- or quantitative PCR, RNA-seq, branched-chain DNA and differential display methods may be used for detecting gene expression levels or producing nucleic acid hybridization data. Those methods are useful for some embodiments of the invention. In cases where smaller numbers of genes are detected, amplification based assays may be most efficient. Methods and assays of the invention, however, may be most efficiently designed with high-throughput hybridization-based methods for detecting the expression of a large number of genes. To produce nucleic acid hybridization data, any hybridization assay format may be used, including solution-based and solid support-based assay formats. Solid supports containing oligonucleotide probes for differentially expressed genes of the invention can be filters, polyvinyl chloride dishes, particles, beads, microparticles or silicon or glass based chips, etc. Such chips, wafers and hybridization methods are widely available, for example, those disclosed by Beattie (WO 95/11755). Any solid surface to which oligonucleotides can be bound, either directly or indirectly, either covalently or non-covalently, can be used. A preferred solid support is a high density array or DNA chip. These contain a particular oligonucleotide probe in a predetermined location on the array. Each predetermined location may contain more than one molecule of the probe, but each molecule within the predetermined location has an identical sequence. Such predetermined locations are termed features. There may be, for example, from 2, 10, 100, 1000 to 10,000, 100,000 or 400,000 or more of such features on a single solid support. The solid support, or the area within which the probes are attached may be on the order of about a square centimeter. Probes corresponding to the genes listed in this invention or from the related applications described above may be attached to single or multiple solid support structures, e.g., the probes may be attached to a single chip or to multiple chips to comprise a chip set. Oligonucleotide probe arrays, including bead assays or collections of beads, for expression monitoring can be made and used according to any techniques known in the art (see for example, Lockhart et al. 1996; McGall et al. 1996). Such probe arrays may contain at least two or more oligonucleotides that are complementary to or hybridize to two or more of the genes described in this invention. For instance, such arrays may contain oligonucleotides that are complementary to or hybridize to at least about 2, 3, 4, 5, 6, 7, 8, 9, 10, 20, 30, 50, 70, 100, 500, 1000, 1300 or more of the genes described herein.

Databases, Computer Systems and Kits

Databases and computer systems of the present invention typically comprise one or more data structures comprising toxicity or toxicology models as described in this invention, including models comprising individual toxicogenomics databases with for instance, pre-calculated component activities, or PTGS scores etc. Such databases and computer systems may also comprise software that allows a user to manipulate the database content or to calculate or generate PTGS scores as described herein from nucleic acid hybridization data or gene expression profiles. Software may also allow a user to predict, assay for or screen for at least one toxic response, including toxicity, hepatotoxicity, renal toxicity, etc, to include gene or protein pathway information and/or to include information related to the mechanism of toxicity, including possible cellular and molecular mechanisms. The databases and computer systems of this invention may comprise equipment and software that allow access directly or through a remote link, such as direct dial-up access or access via a password protected Internet link.

Any available hardware may be used to create computer systems of the invention. Any appropriate computer platform, user interface, etc. may be used to perform the necessary comparisons between sequence information, gene or toxicology marker information and any other information in the database or information provided as an input. For example, a large number of computer workstations are available from a variety of manufacturers. Client/server environments, database servers and networks are also widely available and appropriate platforms for the databases of the invention.

The databases may be designed to include different parts, for instance a sequence database and a toxicology reference database. Methods for the configuration and construction of such databases and computer-readable media containing such databases are widely available, for instance, see U.S. Publication No. 2003/0171876, WO 02/095659, and U.S. Pat. No. 5,953,727, which are herein incorporated by reference in their entirety. The databases of the invention may be linked to an outside or external database such as KEGG (www.genome.ad.jp/kegg); Reactome (http://www.reactome.org/); HUGO (www.gene.ucl.ac.uk/hugo); Swiss-Prot (www.expasy.ch.sprot); Prosite (www.expasy.ch/tools/scnpsitl.html); chEMBL (https://www.ebi.ac.uk/chembl/); OMIM (www.ncbi.nlm.nih.gov/omim); Adverse Outcome Pathway Knowledge Base (AOP-KB) (https://aopkb.org/); ToxCast DB (http://www.epa.gov/ncct/toxcast/); Tox21 (http://www.epa.gov/ncct/Tox21/); ToxRefDB (http://www.epa.gov/ncct/toxrefdb/); Liver Toxicity Knowledge Base (LTKB) (http://www.fda.gov/ScienceResearch/BioinformaticsTools/LiverToxicityKnowledgeBase/ucm2024036.htm); PharmGKB (https://www.pharmgkb.org/); ENCODE (https://www.encodeproject.org/); ENCODE ChIP-Seq Significance Tool (http://encodeqt.simple-encode.org/); Comparative Toxicogenomics Database (CDT) (http://ctdbase.org/); GeneSigDB (http://compbio.dfci.harvard.edu/genesigdb/); Molecular Signatures database (MSigDB) (http://www.broadinstitute.org/gsea/msigdb/index.jsp); DrugMatrix (https://ntp.niehs.nih.gov/drugmatrix/index.html); Library of Integrated Network-based Cellular Signatures) (LINCS) (http://www.lincsproject.org/), TG-GATEs (http://toxico.nibio.go.jp/); Human Protein Atlas (http://www.proteinatlas.org/); STRING 10 (http://string-db.org/); Stitch 4.0 (http://stitch.embl.de/); Gene Ontology (http://geneontology.org/); PubChem (https://pubchem.ncbi.nlm.nih.gov/); ToxBank data warehouse (http://www.toxbank.net/data-warehouse); Connectivity Map database (http://www.broadinstitute.org/cmap/); NCI-60 DTP (http://dtp.nci.nih.gov/branches/btb/ivclsp.html); DrugBank (http://www.drugbank.ca/); SIDER 2 (http://sideeffects.embl.de/); and In a preferred embodiments, the external databases are the CMap/LINCS or TG-GATEs for gene expression data, MSigDB for pathway data.

As such, another aspect the invention includes a computer system comprising a computer readable medium containing a toxicity model for predicting the toxicity of a test agent and software that allows a user to predict at least one toxic effect of a test agent by calculating a PTGS score for the test agent.

The invention further includes kits combining, in different combinations, high-density oligonucleotide arrays, reagents for use with the arrays, signal detection and array-processing instruments, toxicology databases and analysis and database management software described above. The kits may be used, for example, to predict or model the toxic response, or PTGS score, of a test compound. The databases that may be packaged with the kits are described above. In particular, the database software and packaged information may contain the databases saved to a computer-readable medium, or transferred to a user's local server. In another format, database and software information may be provided in a remote electronic format, such as a website, the address of which may be packaged in the kit.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

EXAMPLES

Example 1

Figure 1:
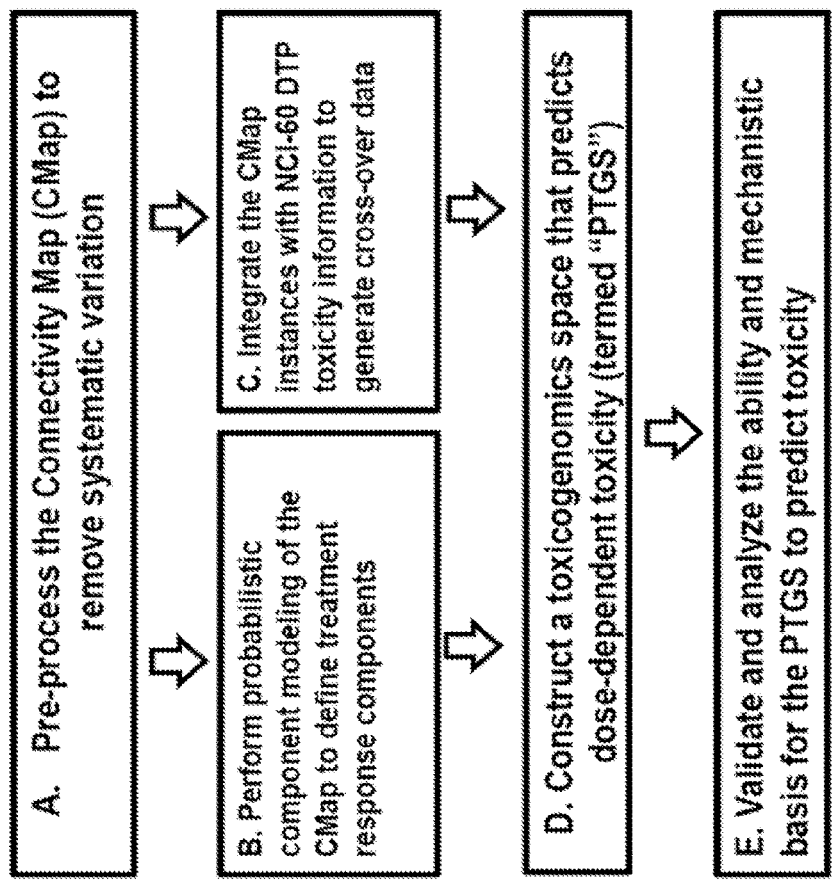
FIG. 1. Key features and steps underlying derivation of the Predictive ToxicoGenomics Space (PTGS). Probabilistic modeling was applied to the overlay of the Connectivity Map and the NCI-60 DTP Human Tumor Cell Line Screen. It generated a genomics space of 14 overlapping components annotated with 1331 genes for wide generalized prediction of the dose-dependency of toxicity effects.
Figure 1:
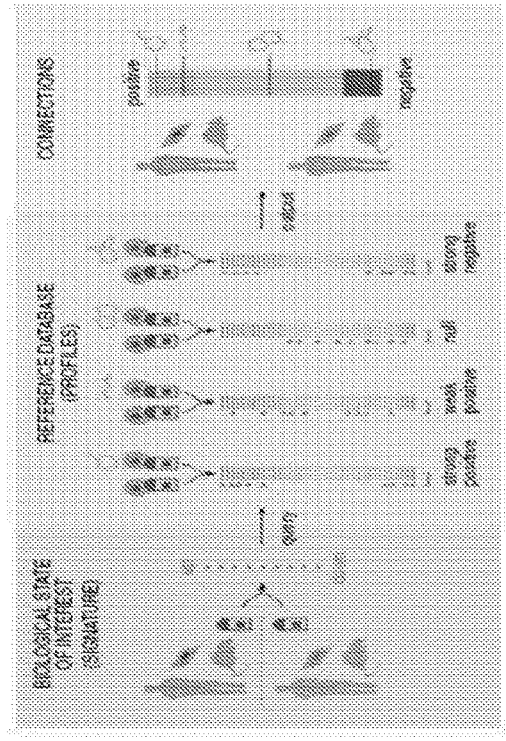
Figure 1:
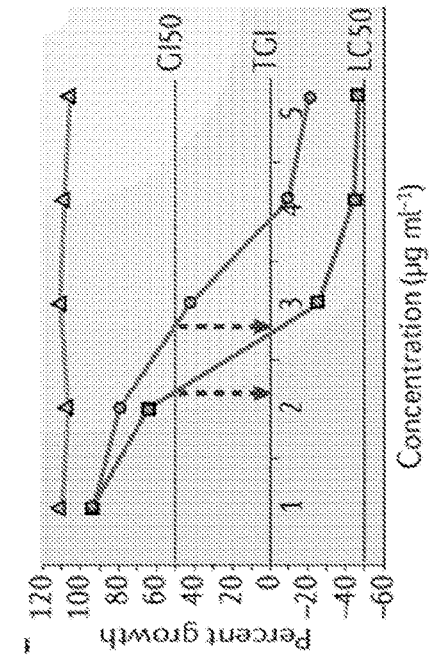
Figure 2:
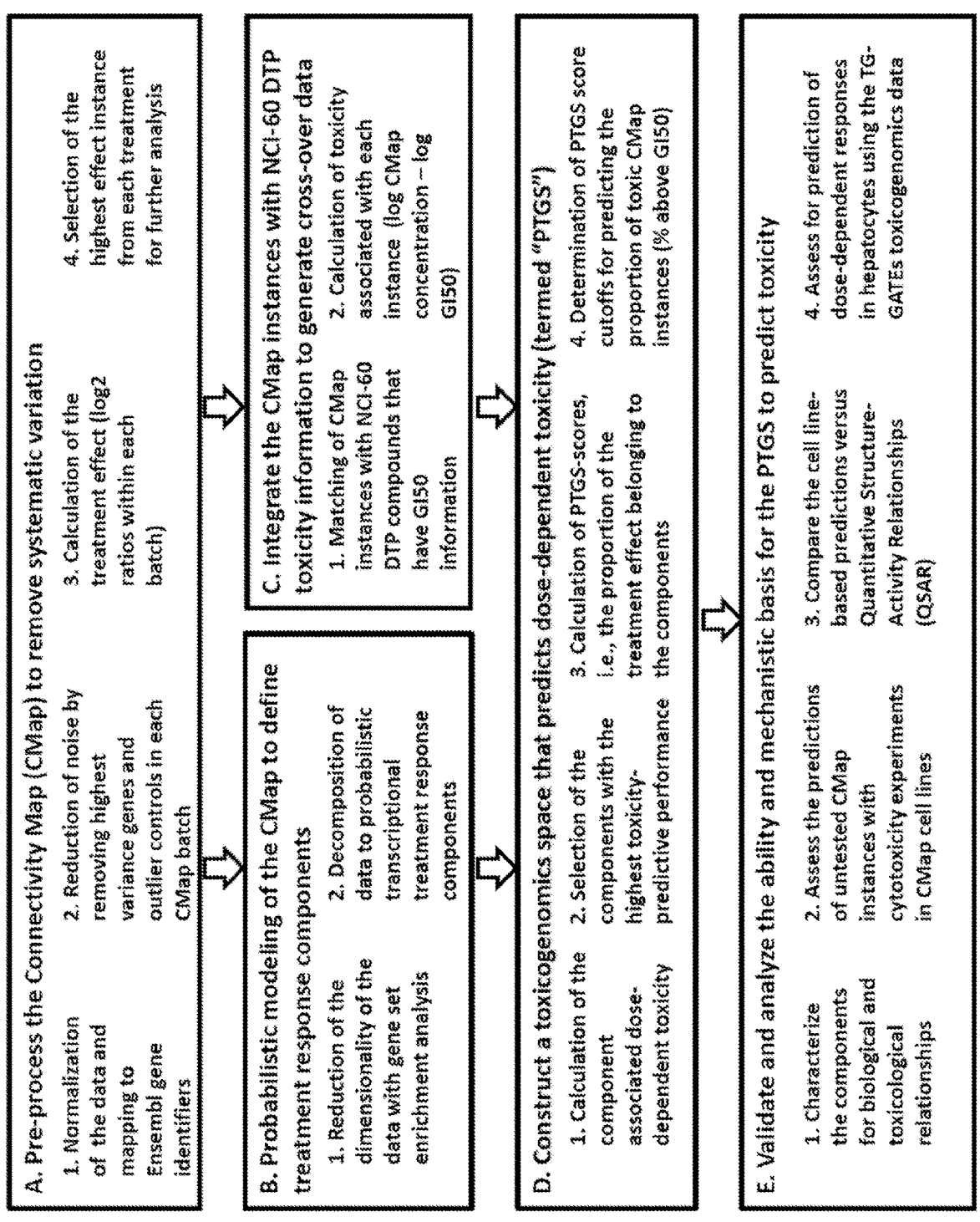
FIG. 2. Component modeling for generating the PTGS. The figure depicts the steps (boxes) and the flow of information (arrows) through the modeling process, including four steps (A-D) to establish the predictive model for calculation of the PTGS score and primary examples of the internal and external validation steps (E).

An integrated data set was produced with 492 measurement instances for 222 unique compounds on three cell lines (MCF7, PC3, HL60), with transcriptional response data from the Connectivity Map (Lamb et al 2006) and toxicological profiles (GI50, TGI, LC50) from the NCI-60 cancer cell line screen (Shoemaker R H 2006) (FIGS. 1-3). Association patterns were sought between the concentration-dependent toxicity (log 10 CMap concentration minus log 10 GI50) and gene expression perturbations, with probabilistic modeling using the combination of Gene Set Enrichment Analysis (Subramanian et al 2005) (GSEA) and Latent Dirichlet Allocation (Blei et al 2003 and Caldas et al 2009) (FIG. 3). The result was a set of components having characteristic profiles over both the compounds and gene sets, representing specific biological processes and pathways activated by the corresponding treatments. A subset of 14 of in total 100 components showed excellent toxicity-predictive performance and was termed the Predictive Toxicogenomics Space (PTGS) (FIGS. 3, 5-6).

The PTGS components were characterized and interpreted with Gene Ontology enrichment analysis and Ingenuity Pathway Analysis based on top differentially expressed genes for each component (Alexa et al 2006 and Kramer et al 2013). The toxicity-prediction performance of the PTGS components was evaluated on independently measured toxicological profiles for non-NCI-60 instances in CMap, and compared against quantitative structure-activity relationship (QSAR) regression models (Willighagen E L et al 2006) which applied Partial Least Squares (PLS) to both molecular and signature descriptors (FIG. 8). The performance was measured by the area under the ROC curve values, and additionally compared to random PLS regression models using y-randomization. The PTGS components were also evaluated on predicting dose-dependent toxicity in human hepatocytes, for a set of selected compounds in the TG-GATEs (Uehara et al 2010) toxicogenomics database against both human and rat in vitro hepatocytes and rat in vivo repeated dose toxicity data relative to pathological findings.

Example 2

A database of toxicity values and associated PTGS scores was produced (FIGS. 1-6). Toxicological profile data were downloaded from the NCI-60 database 10 DTP human tumour cell line screen web site (http://dtp.nci.nih.gov/docs/cancer/cancer_data.html). The data set has three reported drug response values: GI50 (50% growth inhibition), TGI (total growth inhibition), and LC50 (50% lethal concentration) for 59 different cell lines. These values have been inferred from measurements covering typically 5 concentration values, most common range being from 10 to 100,000 nM (or from −8 to −4 log 10 M). The NCI-60 and CMap instances were matched based on the compound names. Additionally, alvespimycin and tanespimycin, named 17-DMAG and 17-AAG in NCI-60, respectively, were added manually. The three drug response values were extracted from NCI-60 data for in total 222 CMap compounds and 492 measurement instances on the three cell lines (MCF7, PC3 and HL60; with 197, 179, and 116 instances per cell line, respectively), averaging over multiple measurements when available. Concentration-dependent toxicity was defined as the difference of the logarithmic CMap concentration and GI50 values. A positive concentration-dependent value indicates that the CMap measurement instance has been produced at higher concentration than its GI50 value and therefore reflects a growth-inhibitory and toxic response. The concentration-dependent toxicity of zero was therefore used as a rough cut-off in the database to classify the instances in a dose-dependent manner. PTGS score values, corresponding to the instances with toxicity data were calculated from the CMap profiling data as outlined in example 1.

Example 3

The test of a new chemical X is done as described above and the sample handling as known in the art (Freshny R I 2010). The PTGS score is calculated as the sum of the activities over the 14 components as in example 1. The level of toxicity of the test compound X is then determined by comparing the PTGS score of the compound X with a database of PTGS scores associated with toxicity values from example 2 to establish a threshold Y for safe levels of the compound when toxicity-predictive component-models are not active at the concentration of the compound X. Using the methods and the database as outlined in examples 1 and 2 (see FIGS. 1-4) there is a 50% empirically derived probability that the toxicity of the compound exceeds the GI50 value when the PTGS score value exceeds 0.1 or 0.12, preferably 0.12 (threshold Y) (FIG. 5-6). If the level of the PTGS score for compound X exceeds threshold Y it means that compound X is toxic.

Example 4

Methods
Pre-Processing of the Connectivity Map Dataset
The Connectivity Map (CMap) raw data CEL-files (http://www.broadinstitute.org/cmap/) were robust multi-array (RMA) normalized with R-package aroma.affymetrix (Bengtsson H et al 2008 and R Core Team 2014) and mapped to Ensembl gene identifiers (custom cdf version 12, http://brainarray.mbni.med.umich.edu/Brainarray/Database/CustomCDF/CDF_download.asp) to decrease the low-intensity noise in the data. Results from the most abundant microarray platform (HT-HG-U133A) were used, containing measurements for the three cell lines MCF7, PC3 and HL60. To further reduce the noise in the expression data, the 5% of the genes displaying the highest variance in the control measurements were removed. Differential expression was next computed as the log 2 ratio between the drug treatments and respective control measurements. The CMap measurements had been made in batches, with batch-specific control measurements. In the case of multiple controls per batch, a more robust control was formed by calculating the mean of the control measurements after first removing, as an outlier, the control with the highest (Euclidean) distance to the other controls. To balance between the varying sample sizes for different compounds in the CMap data, the instance for each compound and cell line with the strongest effect, measured as the highest (Euclidean norm of) response, was selected for further analysis. For the 18 compounds with multiple concentrations available, one instance per concentration value was included. The resulting gene expression data consisted of 3062 treatment instances (compound and cell line pair) profiles for 1217 distinct compounds in the three cell lines (MCF7, PC3, and HL60, with 1203, 1131, and 728 instances per cell lines, respectively) over 11,350 genes.

Probabilistic Component Modeling

It was presupposes that compound treatments may activate multiple response patterns, each of which may be shared by several compounds. These patterns were identified with probabilistic modeling that decomposes the chemical-induced transcriptional variation into components of inter-related activity. Biological prior knowledge was brought into the analysis while also reducing the data dimensionality with Gene Set Enrichment Analysis (GSEA) (Subramanian et al 2005), combined with Latent Dirichlet allocation (Blei et al 2003 and Caldas et al 2009). GSEA was computed with the Java software package (version 2-2.05, http://www.broadinstitute.org/gsea), using 1321 distinct C2-curated gene sets v2.5 from the Molecular Signature Database (http://www.broadinstitute.org/gsea/msigdb). The false discovery rate q-value (FDRq), which GSEA produces to represent the strength and direction of the gene set activation, was quantised to non-negative integer values with the transformation min(round(-log 2 FDRq))-1, 0), separately for the positively and negatively activated genes in the gene sets, resulting in activation counts for 3062 instances over 2642 gene sets.

The Latent Dirichlet allocation model was next used to identify transcriptional response patterns from the gene set activation count data. Each resulting component associates probabilistically a subset of the treatments with a subset of the gene sets. Each component thus represents a specific chemical-induced response pattern, interpretable based on the associated gene sets. The component count was chosen (from the set 20, 50, 100, 150, 200, to be 100 where the performance stabilized; FIG. 3) by external validation, to maximize empirical performance in retrieving drugs that share 38 protein targets and fourth level Anatomical Therapeutic Chemical classification codes. The posterior distribution of the model parameters was computed with collapsed Gibbs sampling. For the hyperparameters controlling the sparsity of the model, Gamma hyperpriors were applied with fixed parameters, and their posterior was estimated with Metropolis sampling.

Toxicological Profiles from NCI-60

Toxicological profile data were downloaded from the NCI-60 database DTP human tumour cell line screen web site (http://dtp.nci.nih.gov/docs/cancer/cancer_data.html) (Shoemaker 2006). The data set has three reported drug response values: GI50 (50% growth inhibition), TGI (total growth inhibition), and LC50 (50% lethal concentration) for 59 different cell lines. These values have been inferred from measurements covering typically 5 concentration values, most common range being from 10 nM to 100 µM (or from −8 to −4 log 10 M). The NCI-60 and CMap instances were matched based on the compound names. Additionally, alvespimycin and tanespimycin, named 17-DMAG and 17-AAG in NCI-60, respectively, were added manually. The three drug response values were extracted from NCI-60 data for in total 222 CMap compounds and 492 measurement instances on the three cell lines (MCF7, PC3 and HL60; with 197, 179, and 116 instances per cell line, respectively), averaging over multiple measurements when available.

Concentration-Dependent Toxicity

Concentration-dependent toxicity was defined as the difference of the logarithmic CMap concentration and GI50 values. A positive concentration-dependent value indicates that the CMap measurement instance has been produced at higher concentration than its GI50 value and therefore reflects a growth-inhibitory response interpreted as reflecting toxicity. The concentration-dependent toxicity of zero was therefore used as a rough cut-off to classify the instances in a dose-dependent manner. CMap and NCI-60 endpoint concentrations comparisons indicate that most CMap instances were obtained around 10 µM, inducing a very high correlation between the concentration-dependent toxicity and intrinsic potency values (Pearson correlation 0.94).

Defining the Predictive Toxicogenomics Space (PTGS)

As the CMap generally includes one concentration assessment (10 µM), the data was analysed under the a priori assumption that toxicity-related transcriptomic responses are subject to the chemicals' intrinsic potency to cause toxicity. The 100 components produced by the probabilistic model covered the full space of transcriptional responses caused by the 3062 CMap measurement instances. Associations of the components to toxicity were sought by evaluating their ability to predict the concentration-dependent toxicity for the 492 CMap instances with toxicity data. For this, a five-fold cross-validation procedure was repeated ten times. The 100 components were first ranked based on their probability-weighted mean concentration-dependent toxicity values over the training instances. The mean toxicity values were computed as $TOX_z = \Sigma_i [p_n(i|z) \cdot TOX_i]$, where the normalized probabilities $p_n(i|z)$ for the training instances i to belong to component z were computed as $$p_n(i|z) = \frac{p(z|i)}{\Sigma_{i'} p(z|i')}.$$

The cumulative concentration-dependent toxicity classification performance over the test instances was then evaluated for the components in the ranked order, providing area under the ROC curve values (AUC) for each component count. The mean AUC values over the repeated cross-validations as a function of the component count were used to select the component number (FIG. 3). The most highly ranked components are strongly associated with toxicity on test data, with AUC peaking at 40 components. To focus on the components with the highest relevance to toxicity, the number of components was chosen where the AUC value reached 95% of the highest value, resulting in a trade-off between interpretability and the highest predictive performance. The resulting top 14 components were chosen to define the Predictive Toxicogenomics Space (PTGS). The components were labelled from A-N, with component A having the highest probability-weighted mean concentration-dependent toxicity value. The probability of an instance to belong to the PTGS components was used thereafter as a predictive score for its toxicity.

Biological Characterization of the PTGS

The PTGS and each of the 14 components were characterized by the set of instances and set of genes that are the most active given that the component is active. The most active genes were obtained for each component as follows: top instances having the largest p(instance|component) were chosen, thresholding at cumulative probability reaching 0.2. The same was done for the gene sets. For all genes included in the top gene sets, their differential expression was evaluated within the top instances with a standard two-sided t-test. A set of PTGS-associated genes was defined based on t-test p-value cut-off 0.01, after Bonferroni correction for multiple testing (labelled PTGS_Core). These 199 genes thus strongly associated to the PTGS in general but not with particular components. A total of 1331 most active genes, as indicated by the p-values, were used to characterize individual components. For this analysis, and considering that Bonferroni correction would be too conservative, a ranked list of genes thresholded at the 0.01 level was generated, with the rationale that the higher a gene is on the list, the more evidence there is for it being informative in characterizing the component. The gene lists for the 14 components and via them PTGS overall set are enclosed herein.

Enrichment analysis of the PTGS components using Ingenuity Pathway Analysis (IPA, application version 220217, content version 16542223) and Gene Ontology (GO) enrichment analysis (R package topGO39, version 2.12.0) enabled biological interpretation of the components. The enrichment results were visualized with eye diagrams to aid interpretation 37. The enrichment results were thresholded at p-value 0.001, and at least three genes were required to be annotated to each GO category, IPA toxList or IPA regulator providing 38 toxicological functions, and 62 Biological Processes. IPA upstream regulator analysis results were further filtered to include regulators that were enriched in the overall gene set of 199 genes (PTGS_Core) as well as in at least one of the components and that were connected to other regulators via a mechanistic network (Kramer 2013) (to give further evidence of a genuine regulatory relationship). Furthermore since the overall set did not cover all biological functions, as indicated by the GO enrichment analysis and the other analyses, highly enriched regulators (p-value<10-5) that occurred in at least one third of the components were added, giving a total of 35 upstream regulators (listed elsewhere). Upstream regulator analysis results were correlated with the ToxCast assay information. Information on genes associated with assays was downloaded (http://actor.epa.gov/actor/faces/ToxCastDB/GenesAssocAssays.jsp) and matched with Ingenuity upstream regulators on the basis of the gene symbol.

In Vitro Toxicity Predictions

To validate the predictive performance of the PTGS, a set of CMap instances that were not included in the NCI-60 data set were assessed. Data quality was first verified by replicating the measurements for 36 instances for 16 different compounds already measured in NCI-60. The replicated measurements were well in agreement with the NCI-60 measurements with a Pearson correlation of 0.86. Importantly, the classification of toxic vs. non-toxic repeated in 32 of 36 instances, and the four instances where this changed had a score close to the cut-off in both data sets.

For the actual validation, all the CMap instances without NCI-60 data were ranked based on their PTGS scores. In total 91 instances for 38 unique compounds were then chosen for measurement, including instances from the very top of the list (highest expected toxicity) as well as instances with very low score (controls with expected low toxicity). These 91 instances were then measured using CellTiter-Glo® Luminescent Cell Viability Assay (Promega) on cells treated with the compounds at five concentrations spanning a 10,000-fold range for 72 h in 384-well plates. The raw concentration response data were processed as explained in the NCI-60 web page (http://dtp.nci.nih.gov/), and GI50 values were computed using vehicle (DMSO)-only treated cells cultured in the plates for 72 h (corresponding to 0% GI) and for 0 h (corresponding to starting cell number, TGI). The predictive performance was assessed by ranking the instances based on their PTGS scores, and the ROC curve was plotted (FIG. 8) based on their toxicity, i.e. whether their measured concentration-dependent toxicity was positive or not.

QSAR Analysis

PTGS was compared with predictive models based on the chemical structures of the compounds. Various quantitative structure-activity relationship (QSAR) approaches were tried: partial least squares (PLS), decision trees, and supervised Kohonen maps (Willighagen E L 2006). PLS models were found to perform equally well or better than decision trees and Kohonen maps, and only those details are reported. No support was found for the presence of non-linear patterns. The training set was defined by chemical structures from the NCI-60 data set. For a few compounds it was not possible to confidently map the chemical name to a structure, resulting in structures for 201 of the 222 chemicals (448 of the 492 instances). The validation set was based on the experimental validation data, and resulted in 35 structures of the 38 chemicals (85 of the 91 instances). Chemical structure representations were formed based on theoretical descriptors and molecular signatures. These descriptors were calculated with the Chemistry Development Kit (R-package rcdk47, version 3.1.21). This resulted in 185 descriptors and 2400 signatures with non-zero variation within the test and training sets.

PLS models were trained for the NCI-60 data set correlating the compound structures with their toxicity using PLS. While compounds were classified based on the concentration-dependent toxicity for PTGS, the QSAR models were built to correlate the chemical structure with their GI50 values. Here, a −5 log 10 M cut-off was used, below which compounds were classified as toxic, following previous studies 48. This difference is justified because the concentration dependent toxicity and GI50 values are highly correlated in this data set, as is clear from the small differences between the class labels. Cross validation was used to estimate the suitable number of latent variables for the final PLS models: the smallest number of latent variables was selected that gave performance within one standard deviation of the highest mean performance. The regression models were then used to predict the toxicity classes of the test set compounds (toxic or non-toxic). This performance in the test set, as measured by ROC curves, was compared with PTGS component predictions (FIG. 8), and y-randomization models were used to establish a baseline. To ensure conformity between the complete and reduced data set (85 versus 91 instances), the performance of the PTGS approach was additionally evaluated in exactly the same setup where the QSAR was run, resulting in the AUC value of 0.92, equal to the reported PTGS performance. The QSAR modeling results were determined not to result in models significantly better than random models generated with y-randomization, and were thus always worse than the predictions based on the PTGS components. Tanimoto similarity measurements between the compounds were made to evaluate the hypothesis that the diversity between the compounds in the data sets makes it impossible for the PLS to find structural differences that correlate with differences in toxicological activities using similarity measurements.

In Silico Toxicity Predictions

To assess the validity of the PTGS score and the individual components against external data using both in vivo and in vitro measurements, liver-related treatments from the Open TG-GATEs (Uehara 2010) database were employed. The in vivo data consisted of treatments of Sprague-Dawley rats with three dose levels (i.e. low, medium and high in the 1:3:10 ratio), with time-matched controls, sacrificed at 24 hr after the last dose of repeated administration for 3, 7, 14, and 28 days. Livers from the rats were profiled for gene expression with 3 animals in each group, and corresponding pathological findings were determined by histological examination. Two types of in vitro studies consisting of primary hepatocytes from Sprague-Dawley rats and from human donors were used. They were treated with three dose levels (i.e. low, medium, high with 1:5:25) with time-matched controls, and harvested for gene expression analysis at 8, 24 hr after treatment.

For normalization and preprocessing of human hepatocyte gene expression data, non-normalized CEL-files were obtained (http://toxico.nibio.go.jp/). After RMA normalisation with the R/Bioconductor package simpleaffy (v. 2.40.0) using mappings of Affymetrix® hgu133-plus-2 array probes to Ensembl gene identifiers from custom cdf files (hgu133plus2hsensgcdf version 17.1.0, see materials and methods: "Pre-processing of the Connectivity Map dataset") differential expression was computed as a log 2-ratio, relative to the time-matched control measurements. Rat in vitro hepatocyte and in vivo profiles were downloaded from the CAMDA 2013 challenge web site (http://dokuwiki.bioinf.jku.at/doku.php/contest_dataset) as FARMS normalized pre-processed differential expression data (log 2 fold change relative to respective control treatments), with replicates collapsed to a single treatment instance. Uninformative genes according to the FARMS metric (0.1 threshold) were filtered out of the dataset. In total, data for 157 compounds was obtained from human hepatocytes (782 instances); and for 131 compounds in both rat hepatocytes (1177 instances) and rat livers (1568 instances). Pathological findings for the rat in vivo data were downloaded (http://dbarchive.biosciencedbc.jp/en/open-tggates/download.html), findings were coded from 1 to 5 based on severity: 1=P (present), 2=minimal, 3=slight, 4=moderate, 5=severe and severity scores from biological replicates belonging to each instance were summed up. The findings were dichotomized using the summarized severity score of at least 2 as the threshold. In total there were 1148 pathological findings connected to 637/1568 instances.

To compute the PTGS component probabilities, GSEA was run on differential expression analysis results using the R/Bioconductor limma version 3.20.9 and, as for the CMap data, the output was quantised. The p(component|instance)-distribution for the component model was estimated using 100 Gibbs sampler iterations for each treatment sample using the p(gene set|component) probabilities learned from the CMap data. Based on the estimated component distributions, the individual component probabilities and the PTGS scores were computed and used for toxicity prediction. Withdrawn drugs associated with drug-induced liver injury concern (Liver Toxicity Knowledge Base; Chen et al. 2013) were identified.

To study the ability of PTGS scores from the rat liver gene expression data to predict pathological findings, receiver operator curves (ROC) were computed for each finding relative to the PTGS score using the pROC version 1.7.2 (http://web.expasy.org/pROC). Significance for the AUCs obtained was computed using two-tailed univariate Wilcoxon rank-sum statistics in R between the effected and non-effected groups.

In order to study which individual components are predictive of liver pathologies, 20 elastic net regularized regression models, one for each type of finding, were fitted with the 14 component probabilities as input (x-variables) and the dichotomized pathological findings as the output (y-variable) and models trained using repeated five-fold cross-validations. A recently developed test for covariance of inference in adaptive linear modeling, implemented in the covTest R package version 1.02, enabled calculation of component-wise p-values (Lockhart et al. 2014). Only findings with more than 10 instances were included in the analysis and the multiple testing correction procedure.

Data Processing and Visualizations

Data were processed and analysed using the statistical programming language R34 (http://www.r-project.org/). Various R/Bioconductor (http://www.bioconductor.org/) packages were used for analysis and processing of gene expression data. Figures were produced with the ggplot250 (R package version 0.9.3.1). The eye diagram source code is available online (http://research.ics.aalto.fi/mi/software/eyediagram/). The R scripts and data for computing the PTGS will be made available online at the time of publication.

Results

Probabilistic Modeling for Generating the PTGS

The PTGS was defined with probabilistic component modeling of the combined CMap and NCI-60 data, as the minimally sized component space that captured dose-dependent toxicity within the complete data set; FIG. 1 depicts the analysis strategy that generated the PTGS. The protocol extracted and reduced the number of data points, chemicals and genes, providing ultimately combined gene expression and toxicity data coverage for 492 CMap microarray data instances (an instance represents a chemical treatment of one cell line) relative to the toxicity effect of 222 CMap chemicals. Positive concentration-dependent data indicated that the CMap measurement instances had been produced at higher concentration than their GI50 value and therefore reflected a growth-inhibitory and potentially intoxicating response. Probabilistic component modeling 25 decomposed the entire pre-processed CMap data, consisting of 3062 instances, to 100 partially overlapping components (FIGS. 1-4). Superimposing the NCI-60 data enabled thereafter a selection of an optimally sized set of 14 components for predicting toxicity of the 492 instances (FIG. 3, see Methods for details). Most components were proportionally active in all cell lines, while only components B and I showed over-representation for a particular cell line (HL60 and PC3, respectively). Hierarchical clustering of the PTGS revealed clustering of the components into one group comprising a majority of the components (G, H, C, I, A, B and N), another less distinct cluster (E and K coupled to J, D and F), and one outlier component (L), demonstrating that most of the components had overlapping gene activities.

Defining the Toxicity Scoring Concept from the PTGS

Activation of any of the PTGS components indicated dose-dependent toxicity (FIGS. 3, 5b). The toxicity effects of the chemicals correlated with the transcriptional variation (Pearson correlation is 0.69; p-value<$2.2*10^{-16}$; FIG. 5a). The 14 components primarily become active at or above the GI50-dose (FIG. 5b). The components covered a wide range of dose-dependent responses (FIG. 5 c-e, 7). Some CMap instances represented toxicities above the TGI level; such instances tended to have many differentially expressed genes and highly active PTGS components, primarily A-C (FIG. 7a,b). On the other hand, instances belonging to the smaller cluster and especially component E but also K and M tended to be active at around the GI50 growth-inhibitory level and displayed smaller numbers of differentially expressed genes (FIG. 7c). Few instances reflected cell-killing doses (FIG. 5e, 7a). To rank chemicals for probability of toxicity, a PTGS score was defined as the sum of the contributions of the 14 components (FIG. 6a,b). PTGS scores relative to concentration-dependent toxicity serve to indicate how gene expression profiles couple to toxicity (FIG. 6a). The proportion of CMap instances with PTGS score higher than the cut-off set at the GI50-level is used to set a threshold for considering an instance being "toxic". The preferred cut-off (0.12) was set to a level where 50% of CMap instances are above the GI50-level of growth inhibition (FIG. 6b).

The PTGS Reflects Diverse Cellular Toxicity Mechanisms

To assess the mechanisms and modes of action ascribed to the PTGS (FIG. 2e), the 14 overlapping components were annotated with the most active genes for each component (1331 genes in total). Mechanistic validation of these PTGS-associated genes showed enrichment for a variety of basic biological and metabolic processes known to be associated to growth inhibition, cellular toxicity and stress response pathways. Further analysis pointed to 35 transcription factors regulating the genes within the components. Generally the components within the most largest PTGS cluster enriched for TP53, NR3C1, RELA, NFKBIA, HIF1A and STAT3 regulatory factors, and inflammation-related gene ontology categories, such as toll-like receptor signalling pathways, as well as stress from DNA damage and reactive oxygen. Components E and K enriched cell cycle and cell division related categories, e.g., S phase of mitotic cell cycle and DNA strand elongation involved in DNA replication, as well as related regulators including MYC, CDKN2A, RB1 and E2F1. Of all the regulators, P53, EP300 and CDKN2A were associated with the largest numbers of components.

Toxicity Testing Related Cytopathological Changes are Captured

The analysis of external toxicity-related gene sets indicated enrichment for genes associated with pathological changes in major internal organs, typically involved in adverse drug reactions and those seen in repeated-dose toxicity studies of laboratory animals (Natsoulis 2008, Uehara et al. 2010). Genes associated with components A-C enriched most strongly for liver necrosis/cell death, renal necrosis/cell death and PPARa/RXRa activation, whereas components E and K enriched for G1/S checkpoint regulation, aryl hydrocarbon receptor signaling and p53 signaling. Various components in the largest cluster, including the component G, strongly enriched for cardiac and hepatic fibrosis and cell death related genes. Some components enriched for particular structural and functional classes among the CMap compounds, e.g., components A-C enriched protein synthesis inhibitors and cardenolide glycosides, components E and K enriched HSP90 inhibitors, and components D and F for DNA topoisomerase. Although without marked component-association, 199 PTGS_Core genes had strong PTGS. Supporting the value of the component-driven approach, the majority of enrichment from this gene set are recovered from individual components, and the component-level enrichment analysis produced overall higher significance p-values. Analysis of single components therefore serves for grouping and read-across. For example, Connectivity Map compounds with highly active component G contain mostly DNA-binding topoisomerase I or II inhibitors; 1,4-chrysenequinone and CP-645525-01, with unknown toxicities, are inferred by association to be DNA binding with predicted toxicities similar to DNA topoisomerase inhibitors, e.g., camptothecin. In addition or alternatively, the whole PTGS can operate to group together compounds with similar toxicities, either based on single components or on the activity patterns of components. Correlation measures, e.g., the Pearson correlation coefficient, can then be used to match activity patterns for assessing toxicity by read-across (FIG. 17).

The PTGS Outperforms QSAR Predictions

Cell culture experiments aimed at validating the component model showed that the PTGS-based score outperformed data generated from quantitative structure-activity relationships (QSAR) (FIG. 8). Assessment of 38 non-NCI-60-assessed chemicals profiled as part of the CMap for cytotoxicity at concentrations between 10 nM to 100 µM demonstrated a wide range of toxicity effects. A separate set of data from 16 NCI-60-assessed chemicals verified the quality of the applied cytotoxicity assay relative to the NCI-60 results. The PTGS score predicted the toxicity of the non-NCI-60-assessed chemicals with a high sensitivity and specificity (FIG. 8). The QSAR analysis encompassed structures for 201 of the 222 chemicals (448 of the 492 instances). The validation set was based on the experimental validation data, and resulted in 35 structures of the 38 chemicals (85 of the 91 instances). QSAR modeling did not result in models significantly better than random models, and always performed worse than the predictions based on the PTGS components. Poor performance of the QSAR analysis is potentially related to high structural diversity, as evaluated using the Tanimoto similarity measurements between the compounds in the data sets.

The PTGS Predicts Dose-Dependency within the TG-GATES Data

Further validation analyses demonstrated that the PTGS scores increased with the treatment concentration of the compounds profiled in human hepatocytes within the TG-GATEs toxicogenomics database (783 instances were analysed) supporting similar dose-dependent gene expression changes in dividing tumour-originating CMap cell lines as in non-dividing normal tissue-originating hepatocytes. Interestingly, the distributions at all concentrations points in human in vitro treatments exhibit a bimodal-like distribution and a saddle point at around PTGS score=0.12, which coincides with the toxicity threshold where at least 50% of observations in the CMap cell lines exhibit a toxicity above the GI50 level. Furthermore, drugs withdrawn from market due to unexpected hepatic adverse effects 27 produced strong positive scores, including bendazac, benzbromarone, benziodarone, chlormezanone, iproniazid, moxisylyte, nimesulide and perhexiline. A total of 3 of 20 liver pathological scores (i.e., necrosis, acidophilic change and fibrosis), generated significant positive associations for the PTGS within the TG-GATEs repeated-dose toxicity studies in rats. Decomposing the results to the component level, regularised logistic regression analysis of rat repeated dose liver treatments for up to 28 days using the individual component scores as inputs indicated that the components G, H, N and I (together and in various combinations) are especially prominent among models that successfully predict liver pathology after cross-validation, including acidophilic changes, fibrosis, cellular infiltration, necrosis and swelling.

One Fifth of the Overall Gene Response is Toxicity Predictive

The outcome of the analysis strategy (depicted in FIGS. 1-2) in regards to the alterations of the data points, instances, chemicals, components and genes are shown in FIG. 4. The millions of data points extracted from the CMap were thus reduced, transformed and decomposed to 0.7% of the original data size. Altogether, 11% of the genes (22% of the responsive genes, i.e., 1331 versus 6064 genes) were ultimately connected to toxicity-related transcriptomic changes (FIG. 4).

Discussion

The composite analysis underlying the generation of the PTGS surprisingly demonstrated that it performs well in predicting dose-dependent effects across several cell types and toxicity endpoints. The predictive performance of the complete component set is likely based on coverage of a broad collection of compounds with different modes of action and a multitude of toxicity mechanisms. The pathways, regulator relationships and gene ontology categories that characterized the PTGS components agreed with its ability to capture toxicity effects, and validations relative separate CMap instances outperformed analyses based on QSAR. Furthermore, the PTGS score correlated with the compound dosing coupled to human hepatocyte profiling assessments, and scoring relative longer-term animal studies connected the PTGS to few but severe toxicity outcomes like necrosis and fibrosis. Thus, the data-driven modeling approach taken likely served to remove or minimize gene expression changes that related to the pharmacological (non-intoxicating) actions of the drugs tested in the CMap. Different to the common belief that biological responses to chemicals are determined by many undefined interactions with cellular components and processes, the results indicate that overall a relatively limited set of gene-activity components or pathways might account for cellular toxicity reactions.

Cultured tumour cell lines are distinguishable from differentiated hepatocytes in many respects, including related to compound metabolism, often considered an obstacle to generation of reliable toxicity evaluations across models in vitro. Measurement of ATP production, membrane leakage, partial or complete growth inhibition, or decreases in cell numbers are common practices for assessment of toxicity in vitro, and the possibility to validate transcript profiling data across such analyses argues for wide applicability of the PTGS. Interestingly, the bioinformatics annotations covered cellular stress pathways and organismal toxicity often seen from adverse drug reactions and repeated-dose systemic toxicity testing of chemicals in animals (Simmons et al. 2009, Uehara et al. 2010, Natsoulis 2008). Indeed, comparisons between CMap and the TG-GATEs data sets and connectivity mapping studies overall have shown that disparate model systems can trigger similar modes of action at the gene activity level (Lamb et al. 2006). Data-rich modeling of gene expression changes in short-term experiments, as in the current study, might thus serve also for prediction of certain longer-term organismal outcomes. Subject to further studies, the PTGS might partly reflect also unexplored toxicity mechanisms, as comparisons indicated substantial differences versus published toxicity outcome-related gene sets, including those annotated to the ToxCast assays. Important to future application of the PTGS, the component activities and PTGS score can be computed from any gene expression profile with genome-wide coverage.

The analysis strategy dissected and transformed a large genomics data mass extracting thereby essential mechanistic features for probabilistic prediction of dose-dependent toxicity (cf. FIG. 1). The result is a novel extension to the genomics-driven connectivity mapping that so far addressed primarily the pharmacological actions of drugs. Defining potentially all, or most, of the gene activities that underlie toxicity mechanisms, the approach leading to the PTGS might be seen as a first attempt of describing a PTGS-component derived toxome. Scoring-based evaluations of chemicals are needed in regulatory toxicology (Thomas et al. 2013) and collections of PTGS scores could serve as a genomics-driven basis for defining exposure regions of safety outside of regions of adversity for chemical compounds. The PTGS score or the individual component scores could be integrated with approaches such as the ToxPi, as the omics-based component for evaluation of toxicity (Reif et al. 2013). A multitude of future tasks would substantiate the value of the current study with novel data, including considering the integration of the component models and PTGS scoring concept into emerging pathway-based risk assessment strategies (Vinken et al. 2013). To this end, the PTGS would enable relating gene expression changes to a toxicity-indicating score based on the genomic profile itself, serving ultimately as an internal control relative to toxicity assays or cytopathological data in a chosen cell model or organism. The intriguing possibility that the PTGS could serve as an early, in vitro screening-based indicator for certain types of drug-induced liver injury needs further study, and if proved useful, would have implications to drug development. Future analyses of so far not available gene expression data sets from exposures to environmental pollutants, industrial or agricultural chemicals, including profiles assayed at concentrations lower than the typical for CMap, would likely provide results that extend the applicability of the PTGS.

Finally, the PTGS and the modelling strategy used are likely broadly applicable outside the area of predictive toxicology. This analysis presents a previously untested, novel means of applying "omics" data to prediction of dose-response toxicity relationships. It also forms a basis for a proposed Reduce-Model-Characterize-Predict strategy for biomarker development that offers solutions to the well-known incoherence of results in the biomarker derivation field with the following steps: i) Data reduction to boil the data down to a more easily managed size and to bring in biological prior knowledge for increased reliability; ii) Probabilistic data-driven unsupervised component modelling to identify the most robust patterns in the data, irrespective of their use; iii) Characterization of the component models using external data to assign them to modes of action or to biological or toxicological end-points; iv) Use of the components, as appropriate, either singly or in combination for prediction, including derivation of predictive scores for phenotype ranking. Unsupervised methods are used because traditional toxicogenomics datasets, especially those using animal models for toxicity, including the TG-GATEs and DrugMatrix datasets are not sufficiently large to cover all mechanisms of toxicity and larger sets such as the CMap are needed. But larger sets tend to be unlabelled and therefore require an unsupervised strategy for biomarker development. Dedicated toxicogenomics datasets can be used as test data, as shown. Increases in the amount of data will further widen the scope of what can be predicted and modelled successfully. This study introduces the concept and the modelling technology from the point of view of predictive toxicology and pharmacology. But it also demonstrates how cancer biology and personalized medicine oriented datasets can be repurposed for toxicity prediction by integrating with other types of data e.g., high-throughput cellular screening data and general toxicogenomics datasets. The integrative data-driven modelling approach as demonstrated adheres fully to the concept of optimizing the replacement of animal testing protocols with toxicogenomics and human cell culture-based experiments.

Example 5

A method for predicting and mechanistically characterizing toxicity related responses of biological samples using PTGS-associated genes was devised.

Deriving PTGS-Associated Genes

The PTGS and each of the 14 components were characterized by the set of instances and set of genes that are the most active given that the component is active. The most active genes were obtained for each component as follows: top instances having the largest p(instance|component) were chosen, thresholding at cumulative probability reaching 0.2. The same was done for the gene sets. For all genes included in the top gene sets, their differential expression was evaluated within the top instances with a standard two-sided t-test. A set of PTGS-associated genes was defined based on t-test p-value cut-off 0.01, after Bonferroni correction for multiple testing (labelled PTGS_Core). These 199 genes thus strongly associated to the PTGS in general but were not divided into groups by component. A total of 1331 most active genes, as indicated by the p-values, characterizing the individual components were used for functional enrichment analysis. To generate a component-specific list, and considering that Bonferroni correction would be too conservative, a ranked list of genes thresholded at the 0.01 level was derived, with the rationale that the higher a gene is on the list, the more evidence there is for it being informative in characterizing the component. The gene lists for the 14 components and the PTGS overall set are included herein.

Figure 9:
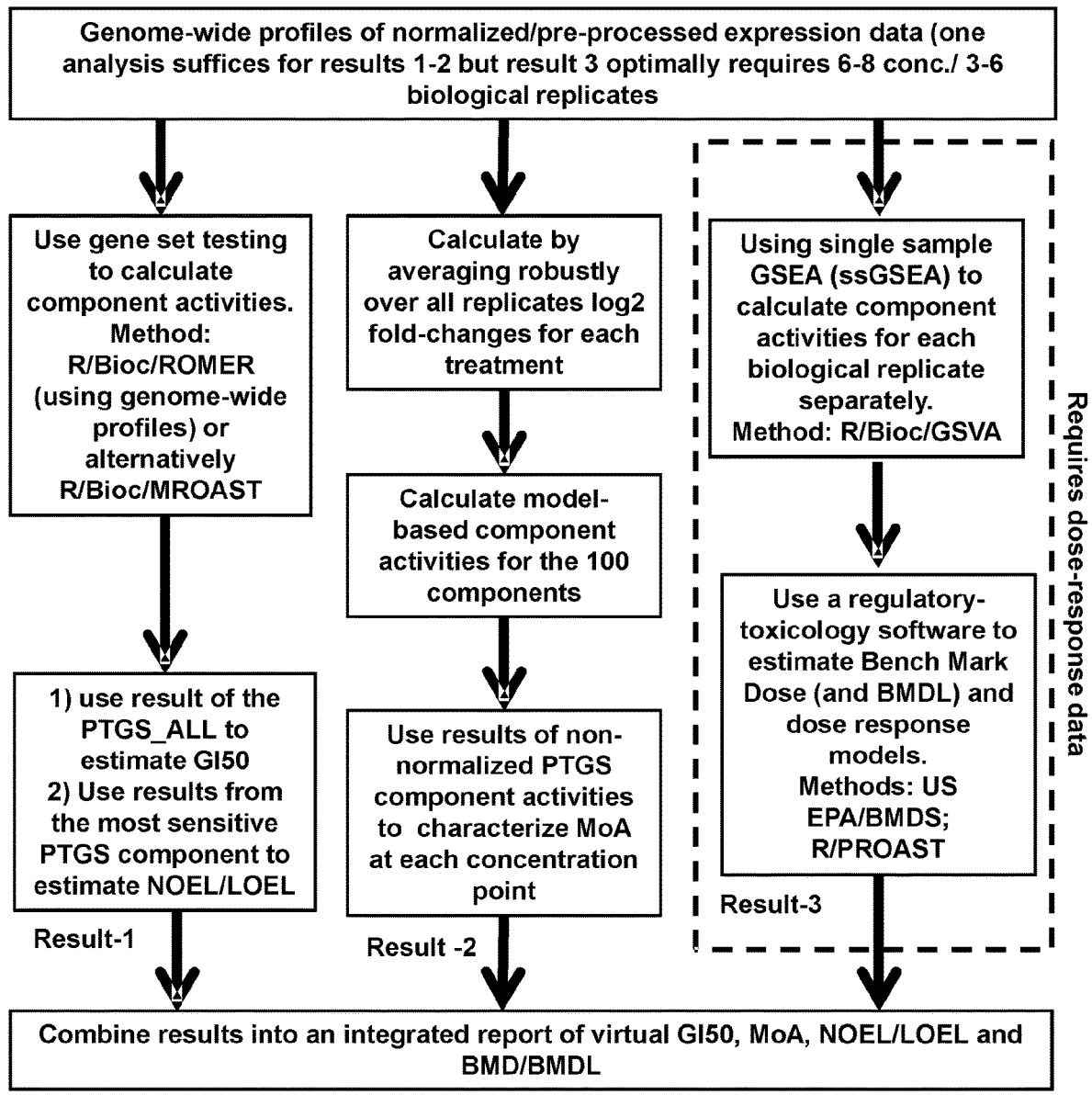

Developing the PTGS-Associated Gene-Based Combined Workflow for Toxicity Evaluation These gene lists (referred to as "PTGS-associated genes" from here on) were then used to derive PTGS-associated predictions using methods commonly referred to as gene set testing or gene set analysis. A multitude of gene set analysis methods exist but there is an agreement in the literature that they can be divided into the following major classes: 1) competitive/self-contained, 2) absolute/directional, 3) multi-sample/single sample, 4) methods which account for inter-gene correlations/methods which are susceptible to errors arising from this source. Using PTGS-associated genes as sets, an investigation was carried out to assess their ability to predict various forms of cellular and organ-based toxicity. The gene set testing methods mentioned above were then combined with PTGS-component derived methods previously described (examples 1-4) into a workflow using a preferred and advantageous combination of methods for toxicity evaluation (FIG. 9). Workflow was validated using the cross-over of Connectivity map gene expression and NCI-60 DTP cell-based screening data and a "Toxicity Testing for $21^{st}$ Century" case study data set (Clewell et al. 2014). Three analysis streams generate for each concentration point a virtual GI50 estimation (result 1-1) and LOEL/NOEL estimation (result 1-2), component-level mode-of action (MoA) (result 2), and BMD/BMDL estimation (result 3). Each of the streams is described in turn below (FIG. 9).

Data Normalization and Pre-Processing

The Connectivity Map (CMap) raw data CEL-files (http://www.broadinstitute.org/cmap/) were robust multi-array (RMA) normalized with R-package aroma. Affymetrix 33,34 and mapped to Ensembl gene identifiers (custom cdf version 12, http://brainarray.mbni.med.umich.edu/Brainarray/Database/CustomCDF/CDF_download.asp) to decrease the low-intensity noise in the data. This left a total of 7056 arrays for analysis. A "Toxicity Testing for $21^{st}$ Century" case study data set was downloaded from the Gene Expression Omibus (GEO) database using the GEO Series accession number GSE59368. A total of 145 microarrays were RMA normalized using the R/Bioconductor simpleaffy package and mapped to Ensembl gene identifiers (custom CDF version 19, see above).

Workflow for Virtual GI50 Value and LOEL/NOEL Estimation (Combined Workflow Results 1-1 and 1-2)

A virtual GI50 estimation and LOEL/NOEL estimation using the PTGS-associated genes approach (FIG. 9): 1) Normalize data to remove systematic variation. 2) Fit treatments and controls to a linear model using R/Bioconductor limma package to calculate the gene set analysis test statistics (limma/eBayes moderated t-statistic; Ritchie et al. 2015). 3) Calculate activities of the PTGS-component derived gene sets and the PTGS_ALL gene set (which contains all of the PTGS-associated genes), applying the limma Rotation gene set testing for linear models (MROAST) Gene Set Analysis (GSA) tool. Alternatively, the R/Bioconductor limma ROtation testing using MEan Ranks (ROMER) gene set analysis tool (Ritchie 2015) or the R/Bioconductor Gene Set Variation Analysis (GSVA) (Hänzelmann et al. 2013) tools can be used. 4) Use the most sensitive GSA result for LOEL calculation and PTGS_ALL to predict GI50 level of activation. The use of each of the different gene set analysis methods is demonstrated in turn to represent different ways of calculating gene set statistics from the PTGS-associated genes for the purposes of toxicity evaluation.

Virtual GI50 and LOEL/NOEL Estimation (Combined Workflow Results 1-1 and 1-2)

The virtual GI50 score afforded by the PTGS is a new concept for toxicity prediction. It is often not possible to assess mild forms of toxicity such as cell growth reduction in more complex life-like cellular models (e.g., human hepatocytes) because these are generally non-dividing cells. But this work implies that chemicals induce, in a concentration dependent manner, similar gene expression changes in cells capable or not capable of dividing. Hence the more abundant data from simpler cellular models can be used to model toxicity between and among various test systems, including from in vitro to in vivo. Extrapolation between in vitro toxicity analyses are hampered from use of different protocols, e.g., seeding density, time until execution of experiment from cell transfer, etc., making an intrinsic virtual toxicity estimate highly valuable for omics experiments.

Figure 10:
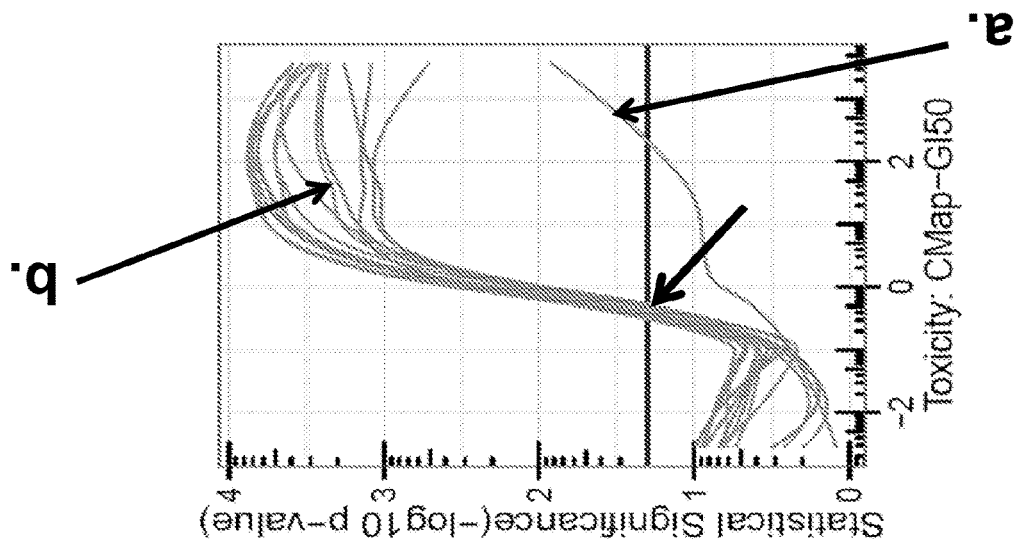
FIG. 10. PTGS-associated gene-based analysis of CMap data using the ROMER method predicts the transition to toxicity above GI50—chemicals with component adjusted p-value<0.05 are classified as potentially toxic. The arrow points to an intersection point between −log 10 of the adjusted p.value<0.05 (statistical significance cut-off) and a LOESS (locally weighted scatterplot smoothing) fit through the ROMER results, indicating that results from instances measure above the GI50-level of toxicity tend to be statistically significant. Similar results were obtained using from the limma R/Bioconductor package both a self-contained Gene Set Enrichment Analysis (GSEA) with the MROAST function and with a competitive GSEA, as shown, using the ROMER function. (a) Component L is an outlier, and less sensitive to dose relative to GI50 than (b) other components A to K, M and N.
Figure 10:
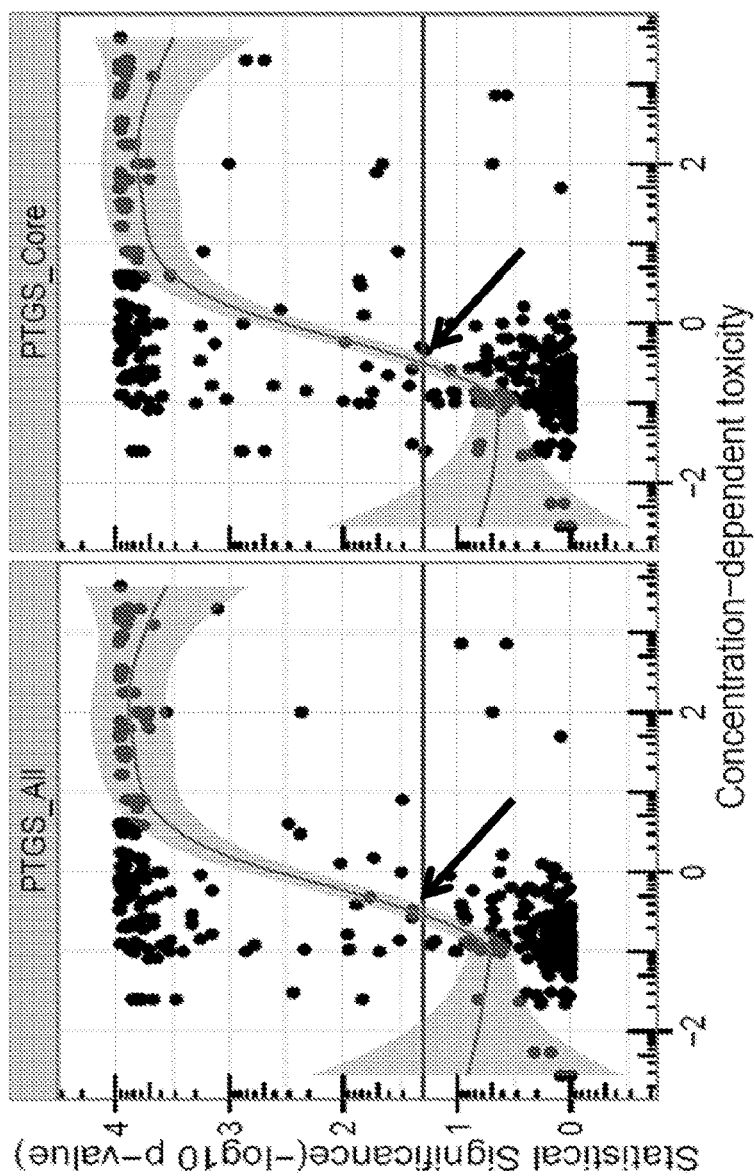

A virtual GI50 estimation of the Connectivity Map data was carried out using the PTGS-associated genes-based method and the R/Bioconductor limma MROAST and ROMER functions. The CMap measurements had been made in batches, with batch-specific control measurements. Since the ROMER and MROAST methods require biological replicates, only CMap batches with a minimum of 3 control measurements were used in the analysis. Treatments with compounds that are part of the 222 compound CMap and NCI-60 DTP cross-over dataset (example 4), were chosen for analysis. After taking into account instances with sufficient replicate measurements in the dataset (typically 5 controls and 1 treatment in each batch), a total of 800 measurement instances covering 186 compounds could be studied. In CMap each measurement is typically repeated 2-3 times in a different batch but biological replicates were analysed separately in this case. Analyses were done with the MROAST and ROMER (FIG. 10) methods in turn, using limma linear modelling with default settings as the test statistic. Analysis using the "PTGS-associated gene-based" method confirms that the PTGS_ALL component gene set and of the component-specific signatures 13/14 become active in 99% of the compounds (184) at statistically significant levels (p<0.05; horizontal line) at or slightly below GI50 level of toxicity (arrow). Both ROMER and MROAST give similar results. Similar results were also obtained for all three CMap cell lines (MCF7, HL-60 and PC-3) with results for the MCF7 cell line shown (FIG. 10).

Figure 11:
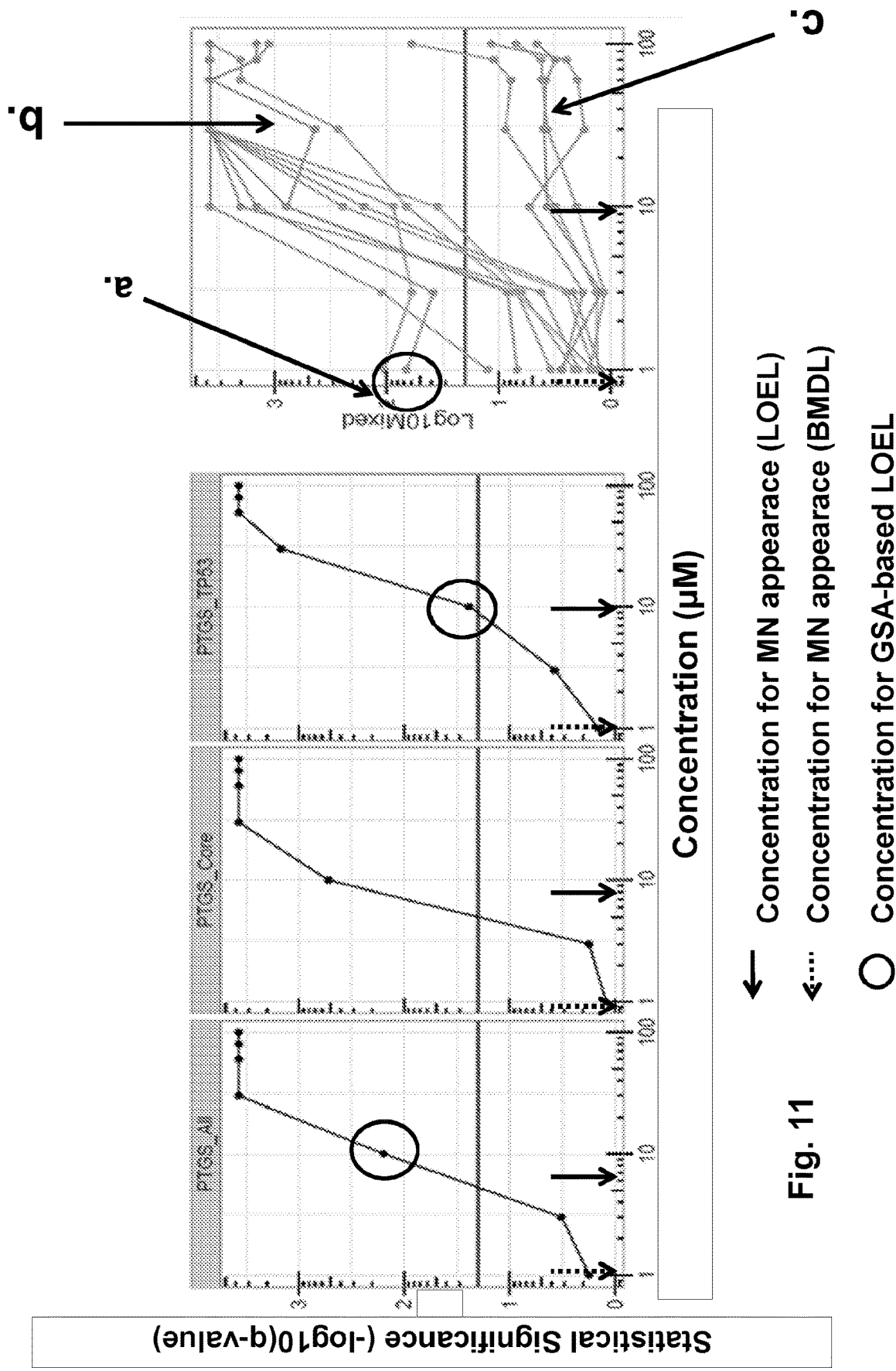
FIG. 11. PTGS-associated gene-based (ROMER) analysis, applying the PTGS_ALL, component subsets and single components, adheres to a distinct dose response and demonstrates its applicability to capture the BMDL for the micronuclei assay. Circles identify LOEL values where the component score (−log 10 of adjusted p-value) becomes statistically significant. (a) Most sensitive components (N and I), (b) Medium sensitive components (A-D, F-H and J), (c) Least sensitive components (E, K-M). Lowest Observable Effect Level (LOEL) at 1 µM with PTGS_I. Similar results were obtained using the MROAST function (Clewell et al. 2014).
Figure 12:
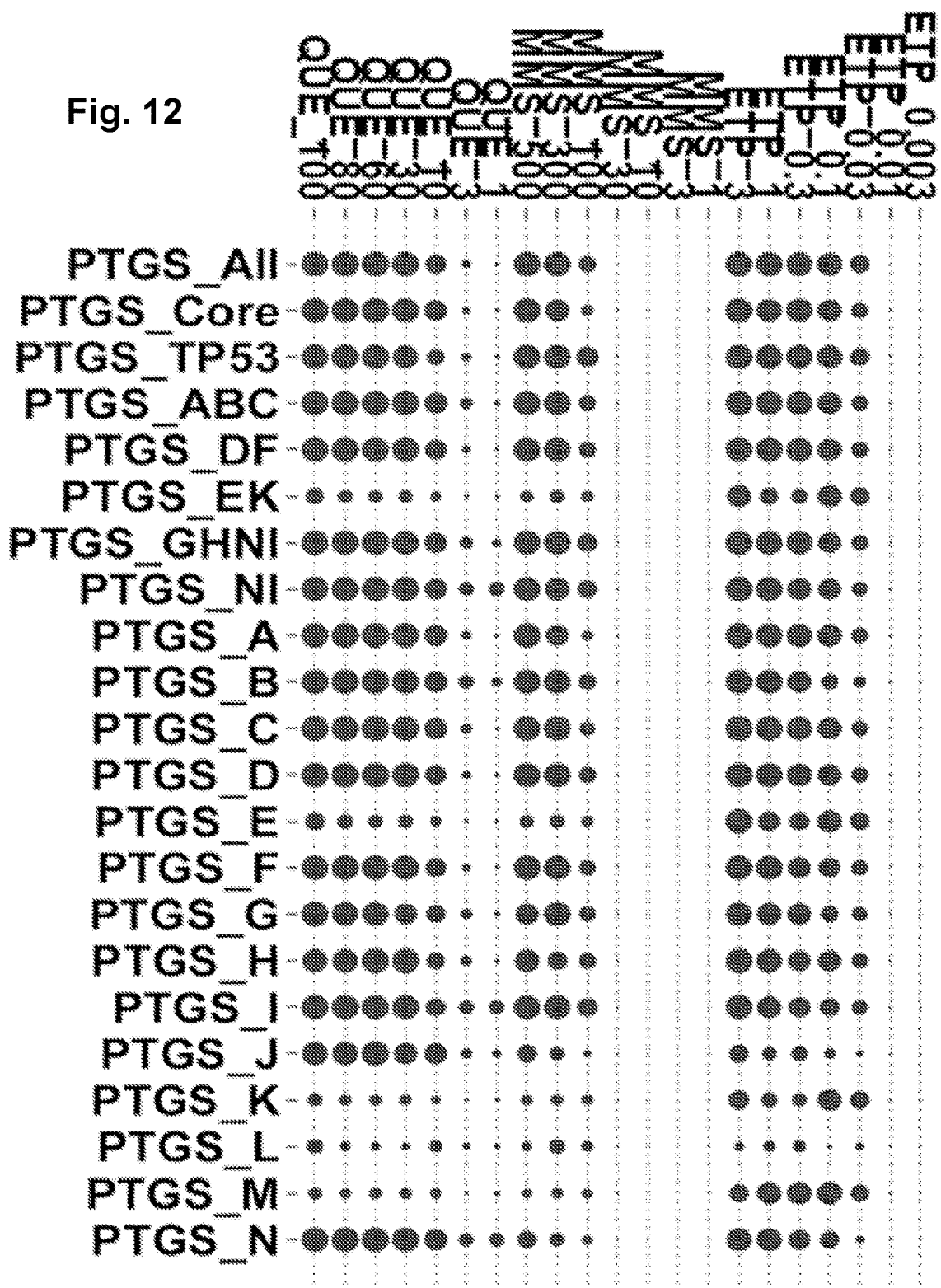
FIG. 12. Activity of PTGS component-associated gene sets by the PTGS-associated gene-based (ROMER) method demonstrates discernible dose response over three distinct compounds assessed over a wide concentration range and the predictable behavior of component combinations relative to their single component parents. PTGS_ALL=All 1331 PTGS genes. PTGS_Core=199 most strongly differentially expressed genes among the PTGS-associated genes; PTGS_TP53=subset of PTGS-associated genes predicted to be direct target genes of the TP53 transcription factor. ETP=etoposide; QUE=quercetin; MMS=methyl metanosulphate, Concentrations (µM) are shown next to the compound abbreviations. Similar results were obtained using the MROAST function in terms of dose response, although with MROAST components responded in a more similar way (Clewell et al. 2014).
Figure 13:
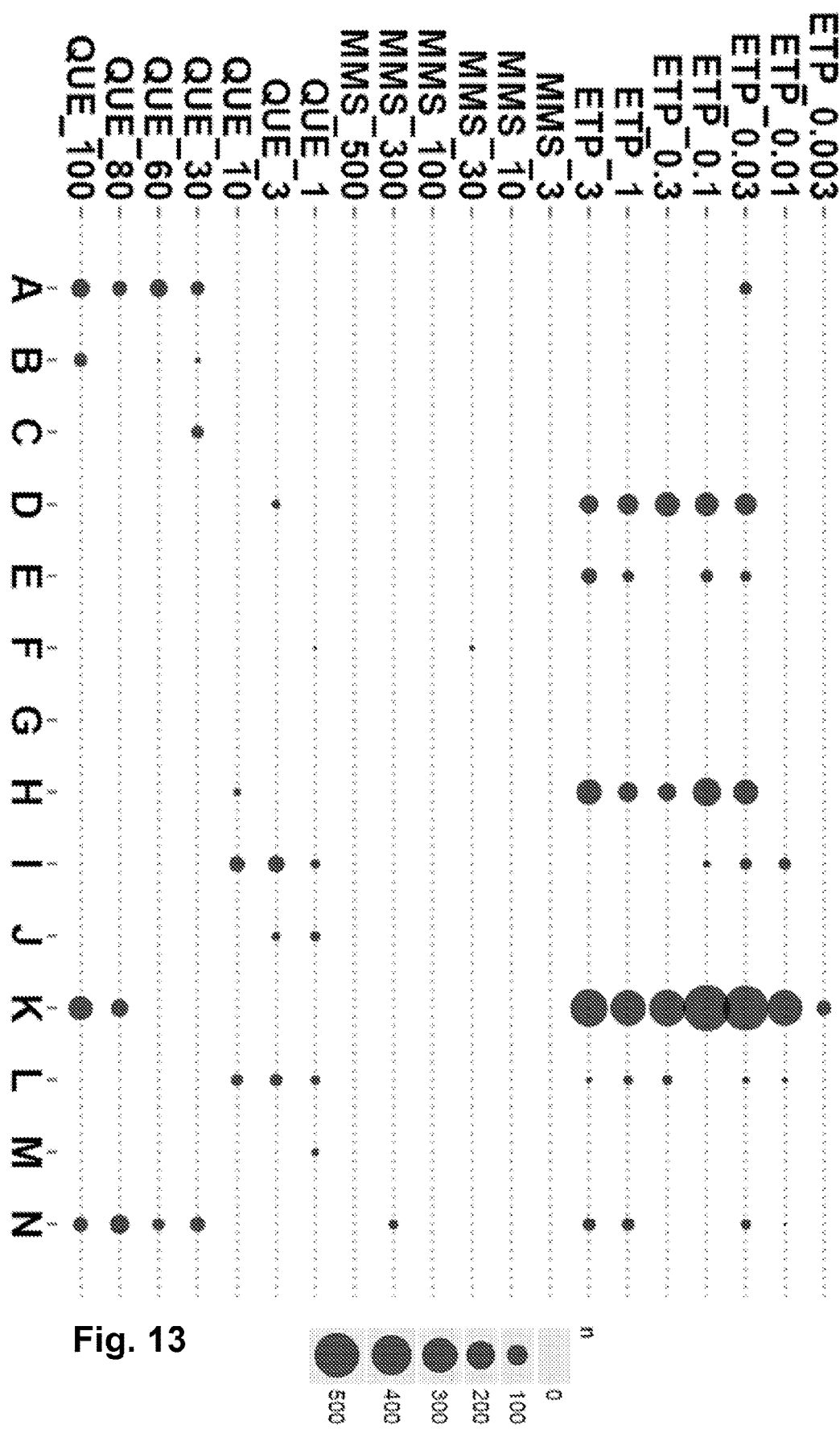
FIG. 13. Activity of the 14 toxicity coupled PTGS components used for understanding mechanisms of toxicity calculated using the PTGS component-derived method (Clewell et al. 2014).

A "21st Century Toxicology-inspired" pathway-based risk assessment case study to support low-dose extrapolation from in vitro test results (animal experiments are questionably relevant to this task) was used to test the workflow (FIG. 9) in its entirety. The premise of the study was to investigate a central gene-mediated toxicity-related mechanism, i.e., the p53 DNA damage response toxicity pathway, following exposure to three agents known to activate this pathway. The HT1080 (cell line expressing wild-type p53) was treated with etoposide, quercetin or methyl methanesulfonate for 24 h, and gene expression analysed over a range of concentrations. As part of the PTGS workflow, a virtual GI50 estimation and LOEL/NOEL estimation using the PTGS-associated genes approach was first carried out. Using normalized data from the study, P-values for the component-associated gene sets were estimated using either the MROAST or the ROMER (FIGS. 11-12) method and the "floormean" gene set summary statistic with 9999 rotations. Multiple testing correction was carried out (false discovery rate) to derive adjusted p-values, that were then −log 10 transformed to derive a positive score between 0 and 4. The most sensitive PTGS component was used for LOEL calculation and the PTGS_ALL component was used to estimate the virtual GI50 value. Results were compared to other methods, including gene expression based by non-PTGS methods. Analysis using the PTGS-associated genes-based method with the ROMER function adheres to a distinct dose response and demonstrates its applicability to capture the p53 pathway-activating concentration. More specifically, most components, including the intersection of PTGS-associated and TP53 target genes become active at a concentration below where TP53 gene expression increases; which is consistent with the mechanism of activation of TP53 protein in response to DNA damage. Gene expression-based LOEL was defined as the lowest concentration where any differential expression was observed (q<0.05 after false-discovery rate multiple testing correction). PTGS-associated gene-based and gene expression based LOELs coincide exactly after the reanalysis of the expression data, indicating that gene set testing is able to detect PTGS activation as soon as any differential gene expression is detected. The PTGS gene sets also predict LOEL at the BMDL of the most sensitive non-gene expression assay in the study, namely the micronucleus assay (FIG. 11). Moreover, the PTGS_ALL component activity predicts the virtual GI50 value at exactly the concentration where GI50 level of intoxication is observed at the 48 hour time point (10 µM).

R/Bioconductor package GSVA (Gene Set Variation Analysis) was used as a further method for gene set testing based chemical characterization. Conceptually, GSVA transforms a p-gene by n-sample gene expression matrix into a g-gene set by n-sample pathway enrichment matrix. This facilitates many forms of statistical analysis in the 'space' of pathways rather than genes, providing a higher level of interpretability (Hänzelmann et al. 2013). The resulting PTGS gene set-based pathway matrix was then analysed, similarly as a gene expression matrix, using the R/Bioconductor limma package employing standard options to produce adjusted p-values for PTGS-based gene set enrichment. The −log 10 of the adjusted p-values (false discovery rate correction) are computed for each gene set and each concentration point. Values below 0.0001 are floored to that value, and used as a positive score taking values between 0 and 4.

Comparing the various gene set testing methods indicates that they give similar results, with the MROAST method displaying clearest monotonically increasing dose response and the GSVA method exhibiting the most specific or at least most variable component activities while still maintaining relatively consistently a monotonic response to increasing dose. ROMER seems to be intermediate in both sensitivity and chemical specificity, and being thus well suited for characterization of the toxicity response (FIGS. 11-12) was thus chosen as the primary method for the combined workflow.

Defining Modes-of-Action (MoA) (Combined Workflow Result 2)

PTGS captures responses (toxicity mechanisms) of 1217 compounds and GI50 toxicity information from 222 compounds and thus is likely to capture many or even most of mechanisms involved in responses to chemicals at the cellular level that lead to changes in cell growth rates, including common homeostatic responses to cellular stress (for details see Example 4).

The activity of the 14 toxicity coupled PTGS components used for understanding mechanisms of toxicity by applying the PTGS-component derived approach to toxicity characterization (FIG. 9; result 2). Starting from normalized data spanning 145 microarrays (Clewell et al. 2014) log 2 fold-change values were determined using the R/Bioconductor limma package, taking into account the study's experimental design and weighing treatments according to estimates relative quality for each array. GSEA was run on the differential expression vector and the output was quantised, as for the CMap data. The p(component|instance)-distribution for the component model was estimated using 100 Gibbs sampler iterations for each treatment sample using the p(gene set|component) probabilities learned from the CMap data to calculate individual component activities. Unlike when calculating the PTGS scores, non-normalized component activities are displayed (FIG. 13) in order to visualize the activity levels of the component-associated mechanisms without influence from activities outside the PTGS. Alternatively the PTGS-associated gene-based approach can be used to define component-related modes of action. The GSVA single sample GSEA method, calculated as above to obtain "combined workflow results 1", offers greatest discriminative ability between the different components and is therefore recommended for this task from among the tested GSA methods which included the MROAST, ROMER and the GSVA.

Calculating the Bench Mark Dose (BMD) and BMDL (Combined Workflow Result 3)

The BMD approach is applicable to all toxicological effects. It makes use of all of the dose response data to estimate the shape of the overall dose-response relationship for a particular endpoint. The BMD is a dose level, derived from the estimated dose-response curve, associated with a specified change in response, the Benchmark Response (BMR). The BMDL is the BMD's lower confidence bound, and this value is normally used in risk assessment studies (as the Reference Point; RP). Any BMD analysis should be reported in such a way that others are able to follow the process leading to the proposed RP. The following set of information should be provided for the critical endpoint analysed: 1) A summary table of the data for the endpoint(s) for which the analysis is reported, 2) The value of the BMR chosen and, when deviating from the default, the rationale for it, 3) The software package used, including the version number, 4) The settings and assumptions of the model fitting procedure, in particular when deviating from the defaults of the software used, 5) The table presenting the models used and their log-likelihoods, information on fitting and accepting models, and the BMDs/BMDLs for the accepted models. The table should be accompanied by a legend providing much of the above required information on the modelling performed, 6) At least one plot of a fitted model to the data for the critical endpoint(s), including the one for the lowest BMDL and 7) The conclusion regarding the BMDL selected.

Benchmark dose calculations were carried out using the PTGS-associated genes approach: 1) Single sample gene set enrichment analysis (ssGSEA) is used to derive for each PTGS component and each biological replicate measurement in the study an enrichment factor. As an example the use of the R/Bioconductor package GSVA (Gene Set Variation Analysis) was tested. Conceptually, GSVA transforms a p-gene by n-sample gene expression matrix into a g-gene set by n-sample pathway enrichment matrix. This facilitates many forms of statistical analysis in the 'space' of pathways rather than genes, providing a higher level of interpretability, 2) Each measurement is then compared to their respective control to derive a quasi-fold-change as a gene set score: GSVAscore=GSVAtreat−GSVAcont. For each distinctive treatment the sample number, mean and standard deviation in GSVAscore is obtained (study included 5-6 biological replicates), 3) Using e.g., the EPA Bench Mark Dose software as instructed in user documentation (BMDS Wizard v1.10-continuousStDev.xlsm is used in this example) and following instructions (e.g., European Food Safety Authority; 2011. EN-113. Available online: www.efsa.europa.eu) the BMD and BMDL concentrations were calculated from models recommended by the software, 4) The analysis is recommended to be repeated for all PTGS components and the best supported component is selected as the endpoint for defining the Reference Point. In an example the subset of TP53 regulated genes among the PTGS-associated genes (termed PTGS_TP53) is used for calculating the BMDL for a compound, Quercetin, using data obtained from the Clewell et al. 2014 study (FIG. 14). Dose-response models and selection criteria for the models for quercetin were: Hill model, which was selected because it had Lowest BMDL, Lowest AIC, BMD/BMDL ratio>5, BMDL 3× lower than lowest non-zero dose. Quercetrin BMD (at 0.95 confidence level) was determined as 5.37 µM and BMDL as 0.77 µM. Thus the values for BMD/BMDL determined by the PTGS-associated gene-based approach for the PTGS_TP53 gene set coincide closely with values for micronucleus assay, at 3 µM (BMD) and 1 µM (BMDL), identified as the most sensitive biomarker for TP53 pathway perturbation (Adelaye et al. 2014). This indicates that gene expression data analysed using the PTGS could have been equally used as the Reference Point for toxicity characterization.

Alternatively bench mark dose calculations can be performed using the PTGS-component derived approach: 1) For each biological replicate calculate log 2-fold-changes separately, 2) Calculate for each measurement GSEA-profile using the Broad Institute tool (utilizing the MSigDB version 2.5), 3) Calculate from the PTGS model component activities for the 100 components, 4) Using Gibbs sampling estimate component activities from the CMap-derived model, 5) Normalize component activities to 1: component=component/sum(all components), 6) Calculate PTGS scores for all replicates by summing up the normalized activities of the PTGS components, 7) Use a regulatory-toxicology software to estimate Bench Mark Dose (and BMDL) and dose response models for the PTGS score to obtain the Reference Point dose as the BMDL value e.g., by employing the US EPA BMDS software or the R/PROAST-package.

The results of example 5 demonstrate the applicability of the invention to benchmark dose analyses. Thus the combined toxicity predictive workflow (FIG. 9) enables a "21st Century Toxicology-inspired" pathway-based risk assessment to be carried out using gene expression omics data. Since the workflow is using the PTGS-associated genes to elucidate Adverse Outcome Pathway (AOP)-related toxicity pathway activations (e.g., TP53 pathway activity) while operating within a space of genes and processes that are toxicity predictive, this approach can be termed and defines the PTGS-AOP conceptual framework.

Example 6

Undesirable toxicity is a major reason for the attrition of anticipated drug molecules in pharmaceutical R&D. The liver is specifically a known target for drug-induced liver injury (DILI) in humans, and moreover, the liver is often the primary target tissue in costly and ethically questionable safety testing in laboratory animals. Failure of drugs in the late part of the drug discovery process costs the pharma industry billions of dollars per year. Drug-induced liver injury (DILI) is the leading reason for post-market drug withdrawal as the current preclinical testing regimens do not accurately predict the risk of DILI.

Analysis of the Open TG-GATEs (Toxicogenomics Project-Genomics Assisted Toxicity Evaluation System) indicates that PTGS activation correlates strongly with liver pathological changes observed in rats after repeated dosing of drugs and chemical compounds at toxic concentrations, and can thus be said to predict those changes. Furthermore, gene expression profiles measured in human and rat hepatocytes can be used to identify drugs with potential to cause drug induced liver injury (DILI) in human patients at concentrations above a 10-100-fold safety margin relative to the drug therapeutic $C_{max}$ blood concentration.

Open TG-GATEs Data Normalization and Pre-Processing

Liver-related treatments from the Open TG-GATEs (Uehara et al. 2010) database were employed to assess the predictive ability of the PTGS-associated gene sets against external data using both in vivo and in vitro data. The in vivo data consisted of treatments of Sprague-Dawley rats with three dose levels (i.e. low, medium and high in the 1:3:10 ratio) with time-matched controls, and sacrificed at 24 hr after the last dose of repeated administration for 3, 7, 14, and 28 days. Liver was profiled for gene expression analysis with 3 animals in each group. Other data obtained include histological examination, blood chemistry, hematology, body weight, organ weight and general symptoms. Two types of in vitro study, primary hepatocytes from Sprague-Dawley rats and from human donors, were used. They were treated with three dose levels (i.e. low, medium, high with 1:5:25) with time-matched controls, and harvested for gene expression analysis at 2, 8, 24 hr after treatment. The human hepatocyte data was downloaded (http://toxico.nibio.go.jp/) and after RMA normalisation with the R/Bioconductor package simpleaffy (v. 2.40.0) using mappings of Affymetrix® hgu133 plus 2 array probes to Ensembl gene identifiers from custom cdf files (hgu133plus2hsensgcdf version 17.1.0). Pathological findings for the in vivo data were downloaded (http://dbarchive.biosciencedbc.jp/en/open-tggates/download.html), numbers of findings were cumulatively summed in the order of severity, i.e. P (present), minimal, slight, moderate and severe, to obtain severity scores for each unique treatment instance. In order to have sufficient samples for analyses, the findings were dichotomized using the summarized severity score of at least 2 as the threshold.
Analysis of Liver Pathology Caused by Repeated Dosing of Chemicals Data consisting of 6765 genome-wide microarrays (78 million data points) assaying toxicity of 143 chemicals from repeated dose treatments of rats for up to 28 days was downloaded from the Open TG-GATEs data base, normalized and subjected to GSEA using the PTGS-associated gene sets. Gene set activities were computed using 9999 rotations with the MROAST or the ROMER method and the "floormean" gene set summary statistic. The –log 10 of the adjusted p-value (false discovery rate correction) was used as the toxicity predictor. ROC curves for the predictive ability of the PTGS_ALL gene set (1331 genes) relative to the severity grade of pathological changes observed in replicated treatments for the MROAST and ROMER methods, respectively indicated highly successful predictive ability. Results for MROAST (AUC) in the ascending order of magnitude of the pathological changes (with sample number n in parentheses) were 0.75 ($p<6.3\times10^{-63}$) P (present) (n=570), 0.74 ($p<1.7\times10^{-58}$) minimal (n=552), 0.82 ($p<9.4\times10^{-70}$) slight (n=320), 0.88 ($p<1.4\times10^{-40}$) moderate (n=113), 0.93 ($p<3.1\times10^{-15}$) severe (n=29). In total n=1689 distinct treatments were analysed. Changes were summed cumulatively from the lowest level indicated, meaning that a level of severity at least as great as the one indicated was predicted. Analysis using PTGS-associated gene sets (MROAST method) demonstrates that all components are able to predict the degree of severity of pathological changes in rat liver (FIG. 15a). The average cut-off (mean+/–SE) of the optimal decision threshold to predict more severe changes also increases with severity, allowing differentiation of pathological grades (units of the threshold: –log 10 of the adjusted p-value) (FIG. 15b). PTGS-associated gene sets were also used to predict 45 pathology endpoints (combination of severity grade and finding) with at least 15 observations in the data set. All endpoints surveyed are statistically significantly predicted (AUC>0.5, p-value by Wilcox rank sum<<0.05) by all of the PTGS components. Similar results were obtained with the ROMER method, though with reduced statistical significance. Severity of all pathological changes was also successfully predicted (AUCs 0.65-0.79; p-values $10^{-8}$ to $10^{-35}$). This indicates that a method defining predictive scores from PTGS-associated genes that are less specific, such as the self-contained gene set test MROAST, can achieve higher predictive ability; possibly due to a more clearer dose response and possibly because it captures more and more diverse mechanistic influences.

Predicting Human Drug-Induced Liver Injury (DILI) Using PTGS

Figure 16:
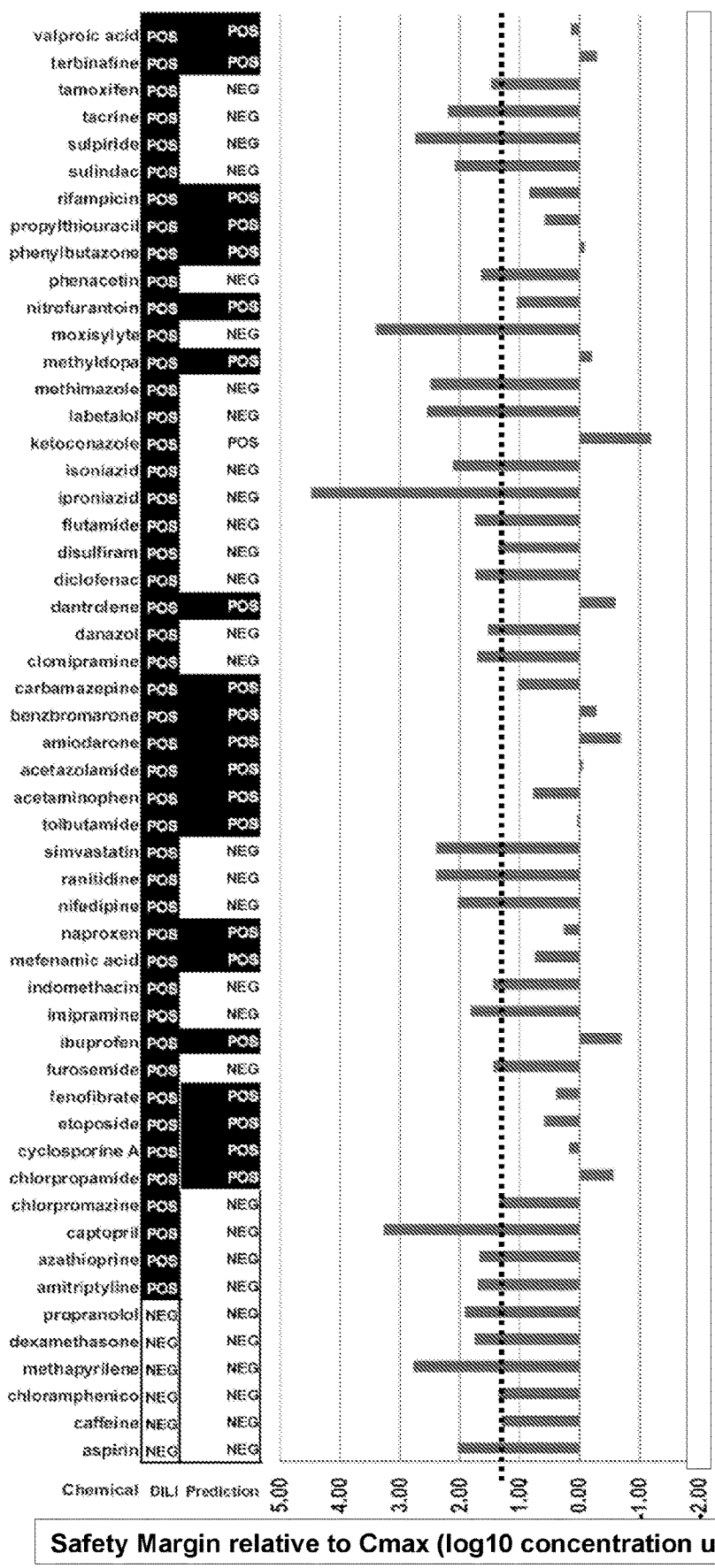
FIG. 16. PTGS-component derived prediction of dose/concentration in blood causing human drug-induced liver injury (DILI) from hepatocyte omics experiments (100% specificity, 45% sensitivity, 53 DILI-classified chemicals tested). Total of 6 negative controls were employed. Safety margin is the difference between measured concentration and therapeutic $C_{max}$ concentration in humans.

PTGS score PTGS-component derived prediction of dose/concentration in blood causing human drug-induced liver injury (DILI) from hepatocyte omics experiments achieves 100% specificity, 45% sensitivity with 53 DILI-classified chemicals tested (FIG. 16). Raw data (2605 Affymetrix microarrays) were downloaded from the Open TG-GATEs database (Uehara et al. 2010), normalized and the PTGS PTGS-component derived score was calculated as previously described in example 5. Using data measured at the 8 hour time point, LOEL values for TG-GATEs human hepatocyte data were derived applying the threshold of PTGS score>0.12 for an effect, as previously discussed herein (FIG. 5-6). LOEL values were compared to $C_{max}$ values derived from literature (Xu et al. 2008) and classified either as causing DILI or not causing DILI using the literature (see for instance, Xu et al. 2008) or the FDA Liver Toxicity Knowledge Base (LTKB) database (Chen et al. 2013). In the literature on in vitro testing to predict DILI, a 100-fold threshold relative to the therapeutic $C_{max}$ is considered adequate for safety. However the concentrations in the TG-GATEs dataset were not designed as multiples of the therapeutic $C_{max}$ values, so DILI negative controls were used to normalize the threshold level to between 10-fold and 100-fold above the $C_{max}$ while ensuring that 100% of the negative controls were identified as DILI negative. Subsequently, the sensitivity to detect known DILI positive could be calculated using the same threshold. A threshold of 1.25 on log 10 scale (17-fold) was chosen. A sensitivity (true positive rate) to detect DILI, of 45% was then obtained, same as the sensitivity obtained in a prototypic paper (Xu et al. 2008), prior to the use of machine learning modeling to optimize the result. P-value for detecting DILI correctly was calculated as p<0.02 using chi-squared testing with standard options.

Gene set testing with PTGS-associated genes using profiles measured at 8 hours enables detection of 56% of DILI positive compounds based on human hepatocyte profiles in TG-GATEs. Raw data (2605 Affymetrix microarrays) were downloaded from the Open TG-GATEs database, normalized and GSA statistics computed for 941 comparisons (three doses; 2 hr, 8 hr and 24 hr time points) using the MROAST method from the R/Bioconductor limma package. The most sensitive GSA result was used (threshold p<0.01 or –log 10P>2 for activation). Cmax values (maximal blood concentration) were derived from literature and compared to assay concentrations in the TG-GATEs. Selecting instances where the TG-GATEs hepatocyte applied chemical concentration is below the 15-fold safety margin relative to Cmax and when 100% of the negative controls are predicted to be DILI negative, 56% of 39 DILI positive compounds are predicted to cause DILI. Thus using human hepatocyte data the GSA omics-based DILI test has equal sensitivity relative to a prototypic paper (Xu et al. 2008), while maintaining 100% specificity.

PTGS-associated gene-based approach enables using profiles measured at 8 hours enables detection of 58-62% of DILI positive compounds based on rat hepatocyte profiles in TG-GATEs. Raw data (3370 Affymetrix microarrays) were downloaded from the Open TG-GATEs database, normalized and GSA statistics computed using the MROAST method for 1395 comparisons (three doses; 2 hr, 8 hr and 24 hr time points). $C_{max}$ values (maximal blood concentration) were derived from literature (Xu et al. 2008) and compared to assay concentrations in the TG-GATEs. The most sensitive GSA result (among components A to N) was used as the LOEL to predict DILI (threshold p<0.001 or –log 10P>3 for activation), similarly to Example 5. Alternatively with a composite gene set combining genes associated only with components G, H, N and I, a lower threshold was employed (threshold p<0.01 or –log 10P>2 for activation). Components G, H, N and I are the most strongly liver pathology linked, as identified in modeling studies of liver pathology using TG-GATEs rat repeated dose treatments for up to 28 days (Example 4). A safety margin of 20-fold relative to the therapeutic $C_{max}$ was chosen. When 100% of the negative controls are predicted to be DILI negative, 58-62% of 43 DILI positive compounds (depending on scoring method, see above) were predicted to be DILI positive. Thus using rat hepatocyte data the GSA omics-based DILI test has equal or greater sensitivity relative to a prototypic paper (Xu et al. 2008), while maintaining 100% specificity.

The results of example 6 demonstrate the applicability of the invention to assess risk of agent-induced (e.g., chemicals, drugs, . . . ) liver toxicity, including the consideration of dose-response relationships as well as the in vitro versus in vivo extrapolation, i.e., from rat and/or human hepatocyte experiments to organ effects in vivo of rats and/or humans.

Example 7

Probabilistic modeling was applied to the overlay of the Connectivity Map and the NCI-60 DTP Human Tumor Cell Line Screen. It generated a genomics space of 14 overlapping components annotated with 1331 genes for wide generalized prediction of the dose-dependency of toxicity effects. Particularly, it served for generating a virtual GI50 scoring method useful for predicting various types of liver toxicity in humans and laboratory animals. The PTGS of this invention overall serves as an omics-based adverse outcome pathway (AOP) framework (PTGS-AOP). The concept, as defined in the example 5 and elaborated in examples 1-4 and 6, enables matching of results derived from omics profiles to Adverse Outcome Pathways (AOPs) by using PTGS components as Key Events (KE), correlated through KE relationships (KER) to Adverse Outcomes (AO). PTGS can be employed in combination with AOPs defined e.g., in the AOP Knowledge Base (AOP-KB), substituting PTGS-component derived results where they occur in e.g., AOP-KB schemata. Relationships to liver pathology-related AOs have been demonstrated in example 4 and 6 along with use of PTGS for virtual GI50 estimation; LOEL/NOEL, BMDL and for dose-dependent elucidation of PTGS-coupled transcription factor mediated toxicity pathways (e.g., TP53-mediated; Adelaye et al. 2014) in examples 1-5. Examples of the use of the PTGS concept applied in this invention, for example, as workflows are detailed in FIGS. 9 and 17.

Below is an example of how to apply PTGS products, for example, as a contract service for predicting the safety of customer test agents from omics profiles (FIG. 17). As alternative methods (in silico and in vitro) for chemical safety testing evolve, an increasing proportion of funds could be spent on such new methods as opposed to traditional costly animal testing. This is also evident as the European Chemicals Agency (EChA) advocates a flexible and extensible 'conceptual framework' coupled with reproducible science as a basis for rational combination of information derived from new predictive tools and existing evidence. Innovative predictions through the "Big Data" machine learning analytics, like ones that generated the PTGS, can serve to build up a WoE-enriched Integrated Approach to Testing and Assessment (IATA), with rules detailed in Registration Evaluation and Authorization of Chemicals (REACH) Annexes VII-X (column 2) and XI. Use of PTGS improves on mainly structure-based methods for read-across by implementing more advanced and toxicity-specific methods giving higher weight to expression of toxicity-related pathways and biological processes (example 4). Making the PTGS-based product(s) available in, for example, a cloud platform reduces the burden of procuring and maintaining an IT hardware infrastructure; the costs are easy to quantify and manage, and will enable to scale resources based on planning and demand. The workflow can be used either wholly, or in part, according to the customers' needs. Possible levels of analysis include, for instance, that (FIG. 17):

A) a customer submits a profile for analysis, e.g., generated either by the customer directly or in partnership with a contract research laboratory, or other service providers that can generate gene expression data. Data quality control, pre-processing, normalization and basic bioinformatics is carried out to identify, minimally, differentially expressed genes and biological pathways;

B) in order to facilitate reliable data analysis the raw and normalized data, metadata and protocols can be described according to emerging regulatory standards (e.g., ISA-Tab);

C) preferably, both the combined PTGS-component derived and the PTGS-associated gene-based workflow is run to derive overall and individual component activities (details FIG. 9);

D) in addition to the results from the workflows covered by step C above, component-level results (combined workflow result-2) are used for read-across versus toxicogenomics databases with pre-calculated component activities according to the protocols and databases of this invention. Read-across uses in this case correlation measures (e.g., Pearson correlation) for ranking compounds according to similarity profiles of toxicity-related components (details in example 4 for grouping);

E) the concept enables matching of the results to Adverse Outcome Pathways (AOPs) by using PTGS components as Key Events (KE) correlated through established KE relationships (KER) to Adverse Outcomes (AO). Relationships (KER) to liver pathology-related AOs have been demonstrated (FIGS. 15-16) and F) the toxicity evaluation to support decision making further includes: 1) a PTGS-based virtual GI50 score applicable to toxicity estimation and ranking (FIG. 6, 10); 2) analysis of in vivo pathology based on in vitro data e.g., rat liver pathology and human DILI estimation (FIGS. 15-16); 3) supporting threshold of toxicological concern rating with in vitro data (FIGS. 5-7; 10); 4) dose-response estimation including deriving NOEL/LOEL (FIGS. 6, 11-14); 5) Mechanistic analysis using pathway-based methods applying the PTGS components (FIGS. 7, 13); 6) biological similarity estimation e.g., for grouping/read across between compounds (FIG. 13) and 7) ab initio toxicity prediction of compounds based on the PTGS-AOPs conceptual framework (FIG. 9-14, 17). Parts A, C and D as described above can be fully automated as part of a toxicity evaluating computer system, B is likely to require human curation, part E can be also fully automated, but benefits from human evaluation of the data. In part F, a toxicity report can be generated in a fully automated way for expert evaluation of the results (e.g., for evaluating DILI potential of drugs under development or for regulatory decision making on chemical safety).

REFERENCES

Adeleye Y, Andersen M, Clewell R, Davies M, Dent M, Edwards S, Fowler P, Malcomber S, Nicol B, Scott A, Scott S, Sun B, Westmoreland C, White A, Zhang Q, Carmichael P L. Implementing Toxicity Testing in the 21st Century (TT21C): Making safety decisions using toxicity pathways, and progress in a prototype risk assessment. Toxicology. 2014 pii: 50300-483X(14)00032-8.

Alexa, A., Rahnenfuhrer, J., and Lengauer, T. Improved scoring of functional groups from gene expression data by decorrelating GO graph structure. Bioinformatics 22, 1600-1607 (2006).

Bengtsson, H., Simpson, K., Bullard, J. & Hansen, K. aroma.affymetrix: A generic framework in R for analyzing small to very large Affymetrix data sets in bounded memory. Tech. Rep. 745, Dept. of Statistics, University of California, Berkeley, (2008).

Blei, D. M., Ng, A. Y., and Jordan, M. I. Latent dirichlet allocation. J. Mach. Learn. Res. 3, 993-1022 (2003).

Caldas, J., Gehlenborg, N., Faisal, A., Brazma, A., and Kaski, S. Probabilistic retrieval and visualization of biologically relevant microarray experiments. Bioinformatics 25, i145-i153 (2009).

Chen M, Zhang J, Wang Y, Liu Z, Kelly R, Zhou G, Fang H, Borlak J, Tong W. The liver toxicity knowledge base: a systems approach to a complex end point. Clin Pharmacol Ther. 2013; 93 (5):409-12.

Clewell R A, Sun B, Adeleye Y, Carmichael P, Efremenko A, McMullen P D, Pendse S, Trask O J, White A, Andersen M E. Profiling dose-dependent activation of p53-mediated signaling pathways by chemicals with distinct mechanisms of DNA damage. Toxicol Sci. 2014 November; 142 (1):56-73.

Freshney R I. *Culture of Animal Cells: A Manual of Basic Technique*. 6th ed. Hoboken, Wiley-Blackwell N.J. (2010).

Goeman J J, Bühlmann P. Analyzing gene expression data in terms of gene sets: methodological issues. Bioinformatics. 2007 Apr. 15; 23 (8):980-7.

Hänzelmann S, Castelo R, Guinney J. GSVA: gene set variation analysis for microarray and RNA-seq data. BMC Bioinformatics. 2013 Jan. 16; 14:7.

Kramer, A., Green, J., Pollard, J., and Tugendreich, S. Causal analysis approaches in Ingenuity Pathway Analysis. Bioinformatics, btt703+ (2013).

Lamb, J. et al. The Connectivity Map: using gene-expression signatures to connect small molecules, genes, and disease. *Science* 313, 1929-1935 (2006).

LINCS: The Landmark Genes. http://lincscloud.org/the-landmark-genes/(2012).

Lockhart, R., Taylor, J., Tibshirani, R. J., & Tibshirani, R. (2014). A significance test for the lasso. The Annals of Statistics, 42 (2), 413-468.

Lockhart et al. (1996), Nat Biotechnol 14:1675-1680.

McGall et al. (1996), Proc Nat Acad Sci USA 93: 13555-13460.

Munro I C, Renwick A G, Danielewska-Nikiel B. The Threshold of Toxicological Concern (TTC) in risk assessment. Toxicol Lett. 2008 Aug. 15; 180 (2):151-6.

Nam D, Kim S Y. Gene-set approach for expression pattern analysis. Brief Bioinform. 2008 May; 9 (3):189-97.

Nam D. Effect of the absolute statistic on gene-sampling gene-set analysis methods. Stat Methods Med Res. 2015 Mar. 2. pii: 0962280215574014.

Natsoulis, G. et al. The liver pharmacological and xenobiotic gene response repertoire. *Mol. Syst. Biol.* 4 (2008).

R Core Team. R: A language and environment for statistical computing. (R Foundation for Statistical Computing, Vienna, Austria, 2014).

Reif D M, Sypa M, Lock E F, Wright F A, Wilson A, Cathey T, Judson R R, Rusyn I. ToxPi GUI: an interactive visualization tool for transparent integration of data from diverse sources of evidence. Bioinformatics. 2013 Feb. 1; 29 (3):402-3.

Ritchie M E, Phipson B, Wu D, Hu Y, Law C W, Shi W, Smyth G K. limma powers differential expression analyses for RNA-sequencing and microarray studies. Nucleic Acids Res. 2015 Apr. 20; 43 (7):e47.

Shoemaker, R. H. The NCI60 human tumor cell line anti-cancer drug screen. *Nat. Rev. Cancer* 6, 813-823 (2006).

Simmons, S. O., Fan, C. Y. & Ramabhadran, R. Cellular stress response pathway system as a sentinel ensemble in toxicological screening. Toxicol Sci. 111, 202-25 (2009).

Subramanian, A. et al. Gene set enrichment analysis: A knowledge-based approach for interpreting genome-wide expression profiles. P. Natl. Acad. Sci. USA 102, 15545-15550 (2005).

Thomas, R. S. et al. Incorporating new technologies into toxicity testing and risk assessment: moving from 21st century vision to a data-driven framework. Toxicol Sci. 136, 4-18 (2013).

Uehara, T. et al. The Japanese toxicogenomics project: Application of toxicogenomics. *Mol. Nutr. Food Res.* 54, 218-227 (2010).

Vinken, M. The adverse outcome pathway concept: a pragmatic tool in toxicology. *Toxicology* 312, 158-165 (2013).

Willighagen, E. L., Wehrens, R., and Buydens, L. M. C. Molecular chemometrics. Crit. Rev. Anal. Chem. 36, 189-198 (2006).

Xu J J, Henstock P V, Dunn M C, Smith A R, Chabot J R, de Graaf D. Cellular imaging predictions of clinical drug-induced liver injury. Toxicol Sci. 2008 September; 105 (1):97-105.

The invention claimed is:

1. A method of defining a predictive toxicogenomics space, PTGS, score indicative of a toxicity prediction for an agent, said method comprising:

transforming gene data defining, for each instance of a plurality of instances, differential gene expression of genes in a test biological sample induced by a test agent into gene set data defining, for each instance of said plurality of instances, an activation value for each gene set of a plurality of gene sets, wherein an instance defines a unique pair of a test agent and a test biological sample;

performing a probabilistic component modeling on said gene set data to define multiple components representing a respective specific compound-induced transcriptional response pattern active for a subset of test compounds and test cell lines, said multiple components encapsulating said genes of said plurality of gene sets;

determining, for a portion of said test agents, a concentration-dependent toxicity reflective of whether a concentration of a test agent applied to a test biological sample to induce a differential gene expression in said test biological sample is above, equal to or below a defined toxicity level; and identifying, based on said concentration-dependent toxicities, multiple prediction components as a subset of said multiple components, wherein the multiple prediction components are predictive of toxicity, wherein said PTGS score is defined as a proportion of differential gene expression, induced by an agent, that belongs to said multiple prediction components, and wherein said PTGS score is indicative of a toxicity prediction for the agent.

2. The method according to claim 1, wherein transforming said gene data comprises transforming said gene data into said gene set data defining, for each instance of said plurality of instances, a positive activation value and a negative activation value for each gene set of said plurality of gene sets, wherein said positive activation value represents a probability value for increased differential gene expression of individual genes in said gene set as induced by a test agent in a test biological sample and said negative activation value represents a probability value for decreased differential gene expression of individual genes in said gene set as induced by said test agent in said test biological sample.

3. The method according to claim 2, wherein transforming said gene data comprises computing gene set enrichment analysis, GSEA, on said gene data to get, for each gene set of said plurality of gene sets, said positive activation value based on a false discovery rate q-value, FDRq, representing the strength and direction of positively activated genes of said gene set and said negative activation value based on a FDRq value representing the strength and direction of negatively activated genes of said gene set.

4. The method according to claim 1, wherein performing said probabilistic component modeling comprises performing Latent Dirichlet allocation, LDA, modeling on said gene set data to define said multiple components; and
wherein performing said LDA modeling comprises:
defining, for each instance i of said plurality of instances, a probabilistic assignment vector p(z|i) to component z;
defining, for each component z of said multiple components, a probabilistic assignment vector p(z|gs) to a gene set gs; and
selecting a minimum number of components while maximizing mean average precision of said LDA modeling based on said probabilistic assignment vectors.

5. The method according to claim 1, wherein determining said concentration-dependent toxicity comprises calculating, for each test compound of said portion of said test agents, a difference of the logarithmic concentration of said test agent as applied to said test biological sample to induce said differential gene expression in said test biological sample and a concentration value inducing a measurable effect on cell growth or viability in said test biological sample.

6. The method according to claim 1, wherein identifying said multiple prediction components comprises:
ranking said multiple components based on their probability-weighted mean concentration-dependent toxicity values $TOX_z$ over said portion of said test agents as training instances i, wherein $TOX_z=\Sigma_i[p_n(i|z) \cdot TOX_i]$ and the normalized probabilities $p_n$ (i|z) for said training instances i to belong to component z is computed as $$p_n(i|z) = \frac{p(z|i)}{\Sigma_{i'} p(z|i')};$$

evaluating cumulative concentration-dependent toxicity classification performance for said multiple components in ranked order by calculating area under receiver operating characteristic curve (AUC) value for each component count; and
identifying said multiple prediction components as the highest ranked components resulting in an AUC value corresponding to a defined percentage of the highest AUC value.

7. The method according to claim 1, wherein
performing said probabilistic component modeling comprises performing said probabilistic component modeling on said gene set data to define 100 components representing a respective specific compound-induced transcriptional response pattern active for said subset of test compounds and test cell lines; and
identifying said multiple prediction components comprises identifying, based on said concentration-dependent toxicities, 13 or 14 prediction components as a subset of said 100 components and being predictive of toxicity.

8. The method according to claim 1, wherein
transforming said gene data comprises transforming said gene data derived from the U.S. Broad Institute Connective Map, CMap, dataset of gene expression induced by drugs in human breast cancer cell line MCF-7, human prostate cancer cell line PC3 and human promyelocytic leukemia cell line HL60 into said gene set data; and
determining said concentration-dependent toxicity comprises calculating, for each test compound common to said CMap dataset and the NCI-60 DTP Human Tumor Cell Line Screen, a difference of the logarithmic concentration of said test agent as applied to said MCF-7, PC3 or HL60 cell line according to said CMap dataset and a concentration value inducing 50% growth inhibition, GI50, in said MCF-7, PC3 or HL60 cell line according to said NCI-60 DTP Human Tumor Cell Line Screen.

9. The method according to claim 8, further comprising:
robust multi-array, RMA, normalizing raw data derived from said CMap data set;
selecting RMA normalized raw data obtained using microarray platform HT-HG-U133A for said MCF-7, PC3 and HL60 cell lines;
removing gene expression data corresponding to the 5% of the genes displaying highest variance in control measurements for said MCF-7, PC3 and HL60 cell lines; and
calculating differential gene expression as $\log_2$ ratio between drug-induced gene expression and control gene expression for said MCF-7, PC3 and HL60 cell lines.

10. A method of predicting toxicity of an agent, said method comprising:
obtaining gene expression data defining differential gene expression of genes in a biological sample induced by said agent; and
calculating, based on said gene expression data, a predictive toxicogenomics space, PTGS, score indicative of a toxicity prediction for said agent, wherein said PTGS score represents a proportion of said differential gene expression in said biological sample, induced by said agent, that belongs to multiple prediction components identified by:
transforming gene data defining, for each instance of a plurality of instances, differential gene expression of genes in a test biological sample induced by a test agent into gene set data defining, for each instance of said plurality of instances, an activation value for each gene set of a plurality of gene sets, wherein an instance defines a unique pair of a test agent and a test biological sample;
performing a probabilistic component modeling on said gene set data to define multiple components representing a respective specific compound-induced transcriptional response pattern active for a subset of test compounds and test cell lines, said multiple components encapsulating said genes of said plurality of gene sets;
determining, for a portion of said test agents, a concentration-dependent toxicity reflective of whether a concentration of a test agent applied to a test biological sample to induce a differential expression of genes in said test biological sample is above, equal to or below a defined toxicity level; and identifying, based on said concentration-dependent toxicities, said multiple prediction components as a subset of said multiple components, wherein the multiple prediction components are predictive of toxicity.

11. The method according to claim 10, wherein obtaining said gene expression data comprises obtaining genome-wide gene expression data defining said differential gene expression of genes in said biological sample induced by said agent.

12. The method according to claim 10, wherein obtaining said gene expression data comprises:

measuring gene expression of genes in said biological sample induced by said agent; and determining said gene expression data as differential expression values for said genes between said measured gene expression of said genes in said biological sample induced by said agent and control gene expression of said genes in said biological sample.

13. The method according to claim 10, wherein calculating said PTGS score comprises calculating, based on said gene expression data, said PTGS score representing a proportion of said differential gene expression in said biological sample, induced by said agent, that belongs to 14 prediction components A-N, wherein component A comprises the following genes: CHST3, BICD1, NDST1, VRK1, RBBP6, CYP27B1, GZMB, STIL, MAP2K3, MKLN1, B4GALT7, ZFX, RBM5, ARID4B, ABHD14A, FADS1, SOCS2, PML, MAP3K14, PIR, RBM16, AMOTL2, SNAPC1, ZNF212, FOXJ3, FNBP4, IFI30, CTSH, ABCC10, IMPA2, MTHFD1, MAP2K4, BCL10, KIF18A, UBE2L3, ZC3HAV1, IL1RAP, INTS6, NUP210, JUN, MCM3, TIMP1, BLZF1, RYBP, ZBTB24, CLK1, FBXL5, POLR3F, NDUFA9, SCYL3, KLF7, GADD45A, RPA3, NDUFB7, PRR3, PSPC1, SUV420H1, TGFB3, SLTM, PPIG, GLB1, GAL, DUSP10, DUT, PRKAB1, MORC3, ZCCHC8, EED, KLF6, AHCY, PRKRIP1, AURKA, RAB27A, TOP1, YTHDC1, TFAP2C, IDH1, TNFRSF12A, BAZ2B, ZNF44, DUSP1, GTF2B, CENPC1, JRK, TFRC, RGS2, MYBL1, NFKB1, HIST1H2AC, FKBP4, SMCHD1, IARS, TUFT1, EP300, KLF10, CSTF2T, FAM48A, USP9X, PDIA4, GRB7, NFIB, TSC22D3, BNIP1, KIAA0020, ASNS, PPP1R12A, DLX2, PHB, NEDD9, CAPN1, KIAA1033, TSC22D1, ZFP36, MEIS1, ID3, NFKBIE, ID2, ORC1L, EHD1, PRDX4, ELF3, SDCCAG1, NUDT1, ZNF131, PER1, CYP1B1, TBX3, UST, ISG20, SFRS12, NDST3, EIF2B5, ADM, SETDB1, CKAP4, PLAU, GNL2, E2F3, MAGED1, KIAA0100, LRP8, CYR61, NCK1, ITGA2, CPOX, MYCBP, ADCY9, TFE3, GARS, MGMT, RPN2, MCM6, UCHL3, TLK2, MYD88, SERPINB1, EZH2, MTHFD2, KIN, GRHL2, ZNF217, H2AFV, TCP1, ASNA1, RBM15B, DNAJB1, SAMHD1, SUOX, MAPK6, F3, PPP1R15A, FBXO38, PYCR1, IGFBP2, PRPF38B, PAPOLA, CLIC1, RCHY1, TNFAIP3, CBX5, TUBB, ERCC5, TMEM97, PEX1, CHST7, BIRC3, ICAM1, CNOT8, PGS1, CDKN1B, CTDSP2, DNMBP, NISCH, MATN2, THUMPD2, CHKA, LIMS1, WDR67 and ZCCHC6;

component B comprises the following genes: RELB, HBEGF, CCNL1, TNFAIP6, NFKBIE, REL, ARIH1, SOS1, NFKB2, TIPARP, PPP1R15A, BIRC3, FAM48A, TNFAIP3, NR4A2, THUMPD2, CNOT2, ZNF23, PTX3, HIVEP1, DPP8, PPP2R2A, NFE2L2, ELF1, KIF18A, BCL3, EED, SLC20A1, TAP1, CXCL1, ZNF267, BTG1, BTN2A1, SRP54, JUNB, RAC2, AGTPBP1, CCL11, FOS, GLRX, NUPL1, IFI16, HLA-A, RNF111, RBM15, SLC25A6, ZFP36, RYBP, AKAP10, ADORA2B, DAAM1, HLA-E, NFKBIA, IL1B, CD83, RBCK1, LF10, MAFF, RBM5, SEC24A, ZNF45, INTS6, CLK4, CHD1, AZIN1, FAM53C, TLR2, NFKB1, TXNIP, TAPBP, TNFRSF1B, MORC3, CD9, GTF2B, ZCCHC6, WAC, PSPC1, FOSB, CEBPB, IFIH1, NOC3L, NCOA3, RBM38, HLA-B, SIAH2, ATP1A1, PRKRIP1, YY1AP1, KLF6, CREB5, SOD1, PTGS2, RRAD, CDH2, PLAU, EGR1, ING3, ZNF136, TLK2, KRT10, GALNT3, XPC, IGFBP7, PMAIP1, DLX2, FSCN1, IGFBP3, LYN, MICAL2, DUSP6, BTN3A3, PPP1R16B, BAMBI, UPP1, MAP2K3, CLK1, UBC, BAG3, CASP1, IER2, CYR61, FBXO38, MTHFD2, KIN, NR4A1, PNRC1, COL15A1, CHAC1, IL8, CX3CR1, ACTG1, CCL7, NRBF2, PHF1, TRADD, ARNTL, TNF, LAMP3, FTH1, RABGAP1L, WEE1, LCP2, OTUD3, ID3, GABARAPL2, ALAD, GBP1, RABL3, WDR67, TRIB1, ZCCHC10, CREM, IL7R, FNBP4, NR4A3, TUFT1, RLF, NBN, SRPR, GEM, PRPF3, GABARAPL1, CENPC1, MX2, IKBKE, TRAF3, PDLIM7, SLTM, ETS2, AHR, PPP1R12A, ZNF180, IER3, RBM39, HLA-C, PTTG1, TBK1, EGR3, DUSP8, ID2, ERCC1, PLAUR, IGFBP2, CCL4, BCL2L11, PTN, IL15, SPTBN1, MTHFD2L, SDC4, PALM2-AKAP2, BRCA2, EHD1, ZNF588, TAF2, SFPQ, PTPRE, IRF1, IRF7, IL1RAP, COL6A1, EGFR, BAZ1A, USP12, PDGFA, NFIL3, ABCC1, OLR1, PELI1, MAP3K14, ZNF195, DUSP1, RIPK2, BCL10, SUV420H1, CCNT2, JRK, STC2 and TFEC;

component C comprises the following genes: CLK4, DUSP1, KLF10, DLX2, EFNA1, NUPL1, POU2F1, NFYA, PSPC1, ZNF263, CLK1, BTG1, TSC22D1, BCL7B, FBXO9, STX3, WEE1, PPM1A, MAFG, SLC38A2, KLF6, ZNF292, IRS2, RBM15, HSF2, DUSP4, BCL6, MKLN1, CYR61, ZNF435, STK17B, AMD1, ZNF281, CCNL1, ZNF239, NEU1, HEXIM1, THUMPD2, UBE2H, PRKRIP1, ZNF23, CD55, TAF5, RBM5, FSTL3, JUND, PITX2, IER5, ZBTB5, CARS, IER2, RABGGTB, STAT3, SIP1, AKAP10, MAP1LC3B, WDR67, NCOA3, ZFP161, BAG3, LRP8, BCL10, FNBP4, PNRC1, PPAT, CETN3, DMTF1, NR4A2, UBE2M, RYBP, YTHDC1, PDGFA, ATP2B1, TIA1, RGS3, PPP1R15A, PRNP, KLF5, CHKA, TMCC1, EPHA2, ELF1, ELF4, THUMPD1, MAFF, ZNF14, SRF, EPAS1, CLK3, EIF2B5, CALU, NRIP1, ID3, H3F3B, REL, SLC3A2, PRKAA1, LDLR, ZBTB43, PBEF1, E2F1, FOXJ3, TNRC6B, MEF2A, TOP1, HSPA1L, ELF3, TFAP2C, ADM, MYD88, TNFRSF12A, PEX13, ILF3, TCEA2, HIST1H2AE, SETDB1, WAC, THBD, IFIT5, NLE1, ARHGEF9, TIPARP, MORC3, PPM1D, DUSP8, EGR1, TCF7L2, SNX5, DNAJB4, DNAJB9, PIAS1, ZNF232, FAM48A, RRAS2, TFE3, ZNF45, PSMD8, SLC20A1, TUFT1, E2F3, DCTN6, KIAA0528, RRS1, GTF3A, SMNDC1, RIPK2, RLF, OTUD3, NOL7, PIK3R1, CCNT2, CLDN4, KIF18A, ZFP36, CFLAR, ZCCHC8, JUNB, TSC22D2, MTMR11, HIVEP1, PCK2, PPP2R1A, JUN, FAM53C, SEC24A, ZNF432, IGFBP3, CYP1B1, BACH1, RNF111, RAB5A, SMAD7, RAB3GAP1, SDCBP, EPHA4, JRK, CNOT8, POP7, TAF5L, PLSCR1, BUB3, NECAP1, BTG2, ZNF136, RIC8B, TADA2L, ZNF22, NMI, YY1AP1, GTF2A2, GRB7, RCHY1, TCF12, NR4A1, NEDD9, NFKBIB, POLR2C, SRRM2, SLCO4A1, SDC4, SHOC2, GEM, SPRY4, ERF, KCNK1, SMCHD1, STAT6, KIAA0907, SMTN, MTERF, NBN, TBC1D9, FNDC3B, TDRD7, BAZ2B, ZC3HAV1, DUSP10, PELI1, CAPN1, PGS1, BRD2, NF1, FBXO38, TNFAIP3, ANAPC13, GLUL, PLAU, EIF5, HIC2, NFKBIA, EFNA5, SURF1, CDC42EP4, GADD45A, CDKN1A, SEMA4C, DYNLL1, BTN2A1, BAMBI, HYAL2, LYPLA2, MARCKSL1, ZFAND5, STK4, INHBB, TLK2, ASNS, VCL, CAP2, SOX15, RAD1, PLAUR, RBM15B, PIK3R3, ATF5, UAP1, RBM39, MYB, MYBL1, DNAJB1, TXNL4A, PIR, ABI2, CDC27, ZNF35, SLC25A16, GINS1, ARNTL, UGCG, TFAM, IFRD1, FGFR1OP, LIMA1, DAAM1, E2F5, AGTPBP1, SCYL3, MTF1, SP1, PMS2L1, TPP1, ID2, RUNX1, MXD1, KIAA0802, FOSL2, PTPN2, CNOT4, EHD1, FOSL1, KLHL2, BAZ2A, RNF7, ZNF282, ZNF195, HSP90AB1, SLC25A37, CTGF, NFIC, SFPQ, HRAS, ID4, PPP1R12A, CSNK1D, TRIO, MAP2K4, MARK3, USP1, ZNF189, TM2D1, TAF1C, GAD1, RAB5C, NCBP2, ITPR1, HIST1H2BN, PTPRE, SERPINB1, OGFR, DNAJB6, UBTF, DCLRE1C, NFIL3, TGFB2, ATF2, RAB11FIP2, COL19A1, H2AFX, SNRK, OTUD4, ZFX, CHUK, E2F4, TGFBI, SFRS12, MAP3K1, TNIP1, DTNA, H1FX, ING3, MKRN1, DIXDC1, NUP98, TXNRD1, BNIP1, MAP3K14, CHAC1, ANXA2, MYBL2, FOXM1, CENPC1, PTGES, COX7A2, DDIT4, STAT1, NONO, MNAT1, SFN, ZNF192, GRHL2, SEC61G, NAB2, DNAJC6, TAF2, PPAP2A, INTS6, CAB39, LZTFL1, KPNA5, BTF3, PPP1R13B, SHOX2, CLTB, FOS, SH3BP2, ZNF187, GTF3C4, ZNF205, CYP2J2, NIPSNAP1, CSRP1, IL11, IL15RA, CASP3, SLC9A1, PMAIP1, EIF4E, TTF1, RAB21, ZNF227, LGALS8, HBEGF, TIAL1, NR4A3, ARHGAP29, NOC3L, SPATA5L1, ZNF44, HIST1H4B, SLC7A5, BSG, CDR2, ARG2, FUSIP1, HES1, MITF, TGDS, CYP27B1, RERE, NFIB, SDCCAG1, TCEAL1, ZNF76, ELL2, ARIH1, SUV420H1, TUSC2, SERPINB5, ADFP, UPP1, PITPNB, USP9X, CPEB3, ZNF267, TRIM21, HERPUD1, CEBPG, GTF2H1, PER1, KLF9, PLK2, CREM, TFAP4, CXCR4, SNRPE, CD97, IL6, FHL1, JMJD1C, CCDC6, NHLH2, PAWR, NRBF2, FOXK2, STC2, ERGIC3, TAP1, CEBPB, FOSB, R1D1, SERPINE1, GAS2L1, PPIG, PHF1, ZNF451, DNAJB5, OXSR1, PRPF38B, ARID4B, DR1, RNF6, ZNF588, RELA and BCAR3;

component D comprises the following genes: ARID5B, KLHL9, POLD3, CENPA, SLC25A12, PTPN3, NPAT, BTAF1, CNOT2, MTMR4, CEP350, BLM, RIF1, RAD54B, TNFRSF1A, GNL2, PUM2, INSIG2, ANKMY2, BAZ2B, POLE2, GNE, NTF3, ATP2C1, SMURF2, ASXL1, CENPF, ZNF318, DTL, NCOA3, RAD51C, SFRS9, TLK2, DOPEY1, LRP6, RPP14, CHD1, SKIV2L2, SOCS6, MAGEF1, ARHGEF7, RBM39, UBR2, PEX14, SFRS3, PANX1, WAPAL, MAT2A, IGF1R, SLBP, FADD, ZBTB24, NUP153, GIPC1, ARIH1, CCT4, MLX, TOPBP1, CASK, DNAJA2, FZD2, BARD1, SACS, ZZZ3, ADORA2B, XPO1, DHX15, NIPBL, ORC2L, SIRT1, KIF5C, WWP1, CENPE, RANBP2, STARD13, MAPK6, BMPR1A, SRGAP2, TRAM2, PHF3, NCK1, HMGB2, FAM48A, COIL, CENPC1, LPP, KIAA0528, TMCC1, EFNB2, UBN1, PSMC2, TARDBP, TRIM32, TPST1, BRD8, RABGAP1, KIF11, IFRD1, MYCBP2, MEIS1, RUNX1, NR2F2, PAFAH1B1, LRIG1, HERPUD1, KIF2A, PARP1, KEAP1, SUZ12, PPP2R2A, TXNRD1, UBE2N, GBAS, TNFAIP8, CUL1, KIAA0922, GCC2, CTNND1, SMC4, GTF2E1, DNMBP, ANKRD17, SOS1, PPM1B, NRG1, CASP8, CORO1C, ZNF146, E2F5, SEC24B, PER2, CRK, RNF14, RBM5, PCNA, UBE2G1, HSPA8, MELK, HNRPDL, SMAD4, PLK4, RCOR1, RSBN1, FNBP1L, CCNA2, BCAR3, CAMSAP1L1, USP12, RRS1, CRLF3, ZFAND5, XBP1, MRFAP1L1, NCOA6, APPBP2, DDX10, SRPK2, KIAA0947, PKD2, TUBGCP3, PHF21A, FBXO46, AMD1, DMTF1, PPRC1, WDHD1, PPP1CC, KIAA1279, GCLC, NET1, ZNF638, FCHSD2, FUT8, PDGFB, ABL1, ZNF451, STK3, SLC4A1AP, USP22, HSPH1, PEX1, JMJD1C, HS3ST3B1, OSBP, TCERG1, NUP98, BIRC2, USP1, ELF1, MRPL15, PIP5K2B, WEE1, ARF6, N4BP1, FNDC3A, CRKL, ADNP, SERTAD2, FRYL, MAP3K4, TBK1, PMP22, KIAA0174, UTP18, SSFA2, HMGCR, CHSY1, BAG2, R3HDM1, HIVEP1, BLCAP, PIK3C3, FAF1, REV3L, GCNT1, KIAA1012, RAB5A, FOXK2, MAP3K5, MLH3, CEP55, TRIM33, ATF2, ANKS1A, GAPVD1, MGLL, CEP135, ID1, KIF14, ZNF281, SON, R3HDM2, CKAP5, POGZ, XRCC5, TBC1D8, NAP1L1, TRIM2, SUPV3L1, SHOC2, THUMPD1, KIF23, NOC3L, CTCF, MYO10, LHFPL2, USP8, CDH2, PSMD12, IRS1, PTK2, ARID3A, WDR7, AURKA, MEGF9, EGFR, PDCD10, RASA1, RABGGTB, FBXL7, GBE1, PAPPA, USP6, LRRC42, KBTBD2, STXBP3, MORC3, USP10, STAM, MEIS2, TFAP2C, PCCA, RBM15B, PGRMC2, G6PD, TIAM1, CDC6, TRIM37, TAF5L, USP6NL, NASP, FZD1, PDE4B, MTX2, TRIP4, ENOSF1, BAZ1A, DYRK2, INPP5F, ZBED4, ELF4, SFRS4, SPOP, MAP2K1, ITSN2, MPHOSPH6, PTPRK, SMAD3, AKAP9, DICER1, PFTK1, R140, RFTN1, LARP4, MPHOSPH9, PSMD14, MTM1, TOP2A, USP3, IL4R, NFE2L2, CBLB, CTDSP2, RARS, ARHGAP29, IL7R, BAT2D1, KIAA1128, ACVR1, DCUN1D4, EMP1, GTF2H1, BACH1, TCF12, RBM25, RBM16, DYRK1A, PITPNB, FNTA, ATP6V1B2, MNAT1, ZFP36L2, ARHGEF2, GATA2, STX3, ACVR2A, RAB11A, MTMR3, RNGTT, KIAA0232, SLK, PMM2, PHC2, PCNT, GTF2F2, NPEPPS, ITSN1, CPT1A, SLC25A17, ZNF292, CUL2, GULP1, CREBBP, MAP1B and STK38;

component E comprises the following genes: SERPINH1, MCM7, RFC4, HSPA4L, DNAJA1, MCM3, E2F1, AHSA1, MAFG, MCM6, DDX11, RFC5, NASP, CDC45L, PRIM1, BRCA1, RBM5, ATP6V1G1, MSH6, MCM5, FEN1, MCM4, TMEM97, ZFAND5, GTF3C3, MCM10, TPP1, CCNB1, CDC25A, CHEK1, RAD51C, APEX1, BAG2, BLM, POLE2, ATAD2, UNG, CCND1, RMI1, PLOD1, USP1, DNAJB6, EXO1, RAD51, CDC2, CDC7, PMS1, PCNA, PRNP, VRK1, CDCA4, ME1, CHAF1A, KCNK1, HDAC6, TMEM106C, CCNE1, DLEU1, MLLT11, CEBPG, XRCC5, POLD2, UBE2B, EED, RFC2, UMPS, PKMYT1, PA2G4, TYMS, MNAT1, PPIH, PSMD11, POLD1, FLAD1, TFE3, CDKN2C, FKBIA, MAZ, CDK4, CCNE2, RECQL4, EZH2, TRIP13, MCM2, INTS6, TFDP1, RAB27A, CCNH, DNTTIP2, DDB2, RELA, HDAC2, FANCL, PTTG1, CDK7, PIK3R1, SOD1, ATP6V0A1, MSH2, ADFP, SLBP and IL10RA;

component F comprises the following genes: ARID5B, RLF, FBXL5, KLHL9, MTF2, ZNF435, POGZ, BTN2A1, BRD1, FEM1C, BAZ2B, RANBP6, COIL, BACH1, ZNF3, RBM4B, ZNF45, ARID4B, ARHGEF7, CSTF1, CLK4, NCOA3, CENPC1, NCK1, NFIL3, RPP38, CHD9, ZNF180, ZNF588, ZNF131, CDC42EP2, RNF113A, TLK2, ZNF44, RIC8B, KBTBD2, BAG5, RBM39, RBM15, ZBTB24, NEDD9, STARD13, SCYL3, ZNF432, SEC31A, INTS6, JMJD1C, ZNF14, TCF21, ZNF23, FOXJ3, NUP153, ZNF217, CLK1, DUSP4, KIF2A, ZNF195, RIPK2, GTF2E1, ZNF451, TIPARP, PGS1, MYC, NGDN, PNRC2, PRPF3, CRKL, ADNP, ZNF292, MORC3, POLS, RBM5, ZCCHC8, ZNF274, ZCCHC6, KIAA0907, TBK1, IER2, ZNF187, STC2, RNF111, KLF6, CNOT2, CHD1, DYRK2, ZNF146, SUV420H1, DCLRE1C, FNBP4, ZNF267, CEP76, CDKN1B, MGMT, MEIS1, KIAA0174, ZNF148, IRS1, DMTF1, E2F3, BCL10, SHOC2, CCNT2, CDK7, SMAD3, TNFAIP8, THUMPD2, EIF5, ING3, RBM16, FADD, ETFB, WEE1, SETDB1, RND3, AMOTL2, ID2, SIX1, ARIH1, DUSP8, AKAP10, MAST4, FAM48A, NTF3, PSPC1, DNMBP, SOCS2, NRBF2, ANKRD46, JUNB, WSB1, CENPA, TNFRSF1A, IFRD1, NFKBIA, BIRC2, ZNF227, KIF18A, TSC22D1, BCL7A, CCNL1, CEBPB, EPM2AIP1, TUFT1, ITPKB, HF3, FBXO38, REV3L, WDR67, ADORA2B, HMGCR, RRS1, NR2F2, ZNF165, N4BP1, PPWD1, RCHY1, KIN, BRD8, CTCF, CEBPG, YY1AP1, KLF5, POLR3F, SPOP, ETS2, NOC3L, FZD2, ASB1, PELI1, TCF7L2, SIAH1, RYBP, SFRS12, PIM1, DDIT4, OLFM4, ZZZ3, ZNF35, PGRMC2, AMD1, AHDC1, JUN, UMPS, BICD1, CSTF2T, TSPYL5, WAC, RABGGTB, SOX4, GAS1, KIAA1462, SIAH2, SLC25A44, ASNS, ZNF331, SKIV2L, YTHDC1, SACS, PRKRIP1, HSPB3, PRR3, BRWD1, RBBP6, PPP1R12A, PHC2, ZCCHC10, FRMPD4, NFKBIE, IL4R, KLF7, MARK3, CITED2, TRAM2, BLCAP, MYST3, ERCC5, PRPF38B, AURKA, OSR2, MYO10, GNRH1, CASP8, PTN, SDCCAG1, TRAF4, HMGB2, FAM53C, GATA3, PTGS2, CEP68, ZNF136, TNFRSF9, PIK3R4, HSPB6, KLF10, PIWIL1, SCHIP1, SLK, SNAI2, VPS13D, CYR61, ERF, MAFF, GCNT1, BDKRB2, DYRK1A, CHAC1 and ZNF629;

component G comprises the following genes: EGR1, JUN, FOS, DDIT3, TNFAIP3, PMAIP1, NFKBIA, GADD45A, NR4A1, GEM, DUSP1, FOSL1, SLC3A2, IER2, EIF1AX, KLF10, KLF2, GINS2, FHL2, FOSB, AKT1, NR4A2, JUNB, HES1, CD55, IER3, DNAJB9, IL8, PCNA, DUSP4, TIMP3, PLAU, SLC39A14, RGS2, TSC22D1, CEBPB, ALAD, SNAI1, HIST1H3B, DAG1, IRF7, CREM, CD59, BCL6, AHR, BTG2, BRCA2, HMGCR, NR4A3, MAPK9, FSCN1, HBEGF, EGR3, MVD, LIF, KLF4, CDC45L, ARMET, HIST1H2BC, BAIAP2, PRNP, ETS2, POP4, SHC1, ELF3, OASL, C10orf119, CPEB3, CSTF2, FGFR3, CCL5, CRKL, BRAF, ISG20, TSFM, KIAA0146, JUND, GLA, GTF2B, ITPR1, CYP1B1, SYK, MAP1B, RELB, STAT3, LITAF, PPAN, SLC9A1, GLRX, NR1D1, EGR4, NP, ABCF2, FST, CSE1L, FTSJ3, HIST1H3G, RDH11, MYD88, RANBP1, C8orf4, CTGF, RXRA, GRB7, NFKB2, MAFG, TRAP1, TOMM20, CDKN2C, ANGPTL4, HDAC5, RRAD, PPARA, SF3A3, EGR2, FGF18, FBP2, TXNIP, MRPS18B, CTH, SLC12A7, CBFA2T3, ID3, ASAH1, PES1, C21orf33, F11R, SULF1, GAL, PIK3R1, KRT17, SRF, BCR, CLDN4, FOSL2, RUNX1 and SAC3D1;

component H comprises the following genes: OPTN, CD8B, IGFBP3, LAMA4, BTG1, TF, YKT6, ANXA2P3, CTSL2, ALDOA, IGFBP2, KRT7, RHOB, RREB1, NEU1, GRN, CDKN1A, S100P, IFI30, SERPINE1, ERCC2, KCNA1, GEM, TGM2, ITM2B, RPS27L, DUSP1, CSRP1, AKR7A2, MDK, RNASET2, ACAA1, ADM, GPS2, CEBPB, SNAI1, ZFP36, NR4A2, KLF4, CITED2, B2M, ECHS1, TNFAIP3, EIF4E, CD44, MPV17, ASNA1, LITAF, LCN2, BSG, MMP1, PTGES2, MAP1LC3B, ARMET, HRSP12, TNFSF9, ID2, CLTB, SOX15, AAMP, FOS, CTGF, SERPINB2, SIPA1, GUK1, TPP1, TSPYL2, PSAP, NR4A1, ERCC1, HADHB, CD9, FURIN, IMP2, FOSB, RPS6KB2, CGREF1, IL18RAP, JUNB, C10orf119, LENG4, CLU, WDR12, SCG5, FTSJ1, NFKB2, PHLDA2, GABARAPL1, SH3BGRL3, HBEGF, TGFBI, SCD, ULBP2, RELA, RPS4Y1, SURF1, KRT17, GADD45A and CACNA1G;

component I comprises the following genes: INPP4B, PDGFB, PHC2, SMAD3, KRT7, IGFBP3, IFNG, STC2, IL18, DKK1, LIMA1, SLC2A1, ACTG1, PLAT, SMURF2, CYR61, UAP1, CTSE, IL8, EFEMP1, PLK2, IL7R, BIK, SERPINE1, NMT2, HDAC9, ADORA2B, CXCL1, DUSP14, TACSTD2, CST6, BASP1, TGFB2, PTX3, GPRC5A, MT2A, TGM2, TNFAIP3, PHLDA1, CDH2, PLA2G4A, TMEM47, CXCL2, LIPG, GADD45A, TSG101, PLOD2, MAPK9, NFKBIA, LAMB3, CTGF, CXCL6, FHL2, LAMA5, EPHA2, FGF2, PLAU, TUFT1, GLIPR1, MAP2K3, CDKN1A, TEK, IFRD1, PTGS2, ID2, MLLT11, BNIP3, BAG3, ATP1B1, NCF2, IGF2, CXCR7, ADM, FLRT2, CD83 and IGF2BP3;

component J comprises the following genes: PSPC1, NEDD9, CAB39, RYBP, SEC31A, PPP1R15A, MAFF, PCDH9, JUN, DAAM1, CNN1, ZCCHC6, ADM, DIXDC1, TNFAIP3, PMAIP1, ADFP, TSC22D3, ZNF432, ZNF267, AGTR1, NFIL3, BCL6, ZNF588, KLF6, PTPRE, TNFRSF9, RLF, SFPQ, PER1, ADORA2B, ASNS, NCOA3, PPAP2A, CLK1, INTS6, FEM1C, MEF2A, TPM2, ELF1, DUSP1, FBXO38, ZNF3, GLUL, DMTF1, BBC3, BACH1, USP12, CRY1, SFRS12, TXNIP, LIMK2, RBM15, RAC2, ENC1, SCYL3, JMJD1C, NAT1, TBCC and SEC24A;

component K comprises the following genes: RPA1, EZH2, MCM5, RFC3, TOPBP1, MCM3, FLAD1, CDC7, MCM2, PRC1, E2F8, UNG, DCK, MAD2L1, TYMS, POLG, BRCA1, HELLS, BARD1, CCNE1, DDX11, MCM7, ORC1L, CDC45L, FEN1, MSH2, TFDP1, FOXM1, CHAF1A, ILF2, KIF4A, MCM4, ASF1B, PCNA, ORC6L, RAD51, RACGAP1, CDK2, MYBL2, RAD51AP1, PRPS1, RFC5, RRM2, POLD3, CCNE2, NEK4, NASP, GMNN, DDX23, UCHL5, USP1, MCM6, MCM10, TRIP13, SNRPD1, RFC2, SLBP, TSFM, RFC1, POLE, KIF20A, POLE2, TFAM, DTL, KIF11, POLD2, BLM, RFC4, MKI67, MRPS12, POLA1, CDC20, SMC2, DTYMK, ZWINT, PRIM1, SLC29A1 and RAD51C;

component L comprises the following genes: HMGCL, ABAT, ADH5 and PGD;

component M comprises: EIF4EBP1, ASS1, MARS, LARS2, PSPH, SARS, EPRS, PHGDH, XPOT, CEBPG, PCK2, GARS, TARS, SLC1A5, CARS, SLC1A4, FYN, AARS, ASNS, VLDLR, CEBPB, MTHFD2, WARS, HAX1, YARS, HARS, ITGB3BP, LAPTM5, MAP1LC3B, TRIB3, IARS and NARS; and component N comprises the following genes: RELB, NFKBIA, SUOX, TNFAIP3, ETS2, NFKB2, HIVEP1, NFKBIE, CD83, RXRA, CEBPB, JUNB, IKBKE, NFKB1, BIRC3, ICAM1, ADAM8, IER3, TNIP1, CXCL2, PTX3, BCL3, GADD45A, TAP1, TNFAIP2, PDGFA, IL8, CFLAR, JUN, BTG2, PLXNB2, ARID5B, SDC4, IL1B, RGS16, KRT14, IL7R and CXCL3.

14. The method according to claim 10, further comprising:
identifying said toxicity representing genes as genes belonging to said multiple prediction components; and
predicting toxicity of said agent based on a percentage of said toxicity representing genes that are significantly differentially expressed in said biological sample as induced by said agent.

15. The method according to claim 14, further comprising:
obtaining gene expression data defining differential gene expression of toxicity representing genes or at least a defined portion of said toxicity representing genes in a biological sample induced by said agent, wherein said toxicity representing genes comprises the genes RELB, HBEGF, CCNL1, TNFAIP6, NFKBIE, REL, ARIH1, SOS1, NFKB2, TIPARP, PPP1R15A, BIRC3, FAM48A, TNFAIP3, NR4A2, THUMPD2, CNOT2, CLK4, DUSP1, KLF10, DLX2, EFNA1, NUPL1, POU2F1, NFYA, PSPC1, ZNF263, CLK1, BTG1, TSC22D1, BCL7B, FBXO9, STX3, WEE1, PPM1A, MAFG, SLC38A2, KLF6, ZNF292, IRS2, RBM15, HSF2, DUSP4, BCL6, MKLN1, CYR61, ZNF435, STK17B, AMD1, ZNF281, ZNF239, NEU1, HEXIM1, UBE2H, PRKRIP1, ZNF23, CD55, TAF5, RBM5, FSTL3, JUND, PITX2, IER5, ZBTB5, CARS, IER2, RABGGTB, STAT3, SIP1, AKAP10, MAP1LC3B, WDR67, NCOA3, ZFP161, BAG3, LRP8, BCL10, FNBP4, PNRC1, PPAT, CETN3, DMTF1, UBE2M, RYBP, YTHDC1, PDGFA, ATP2B1, TIA1, RGS3, PRNP, KLF5, CHKA, TMCC1, EPHA2, ELF1, ELF4, THUMPD1, MAFF, ZNF14, SRF, EPAS1, CLK3, ARID5B, KLHL9, POLD3, CENPA, SLC25A12, PTPN3, NPAT, BTAF1, MTMR4, SERPINH1, MCM7, RFC4, HSPA4L, DNAJA1, MCM3, RLF, FBXL5, MTF2, POGZ, BTN2A1, BRD1, FEM1C, BAZ2B, RANBP6, COIL, BACH1, ZNF3, RBM4B, ZNF45, ARID4B, ARHGEF7, CSTF1, CENPC1, NCK1, NFIL3, RPP38, CHD9, ZNF180, ZNF588, ZNF131, CDC42EP2, RNF113A, TLK2, ZNF44, RIC8B, KBTBD2, BAG5, RBM39, ZBTB24, NEDD9, STARD13, SCYL3, ZNF432, SEC31A, INTS6, JMJD1C, TCF21, FOXJ3, NUP153, ZNF217, KIF2A, ZNF195 RIPK2, GTF2E1, ZNF451, PGS1, MYC, NGDN, PNRC2, PRPF3, CRKL, ADNP, MORC3, POLS, ZCCHC8, ZNF274, ZCCHC6, EGR1, JUN, FOS, DDIT3, PMAIP1, NFKBIA, GADD45A, NR4A1, GEM, FOSL1, SLC3A2, EIF1AX, KLF2, GINS2, FHL2, FOSB, RPA1, EZH2, MCM5, RFC3, and said defined portion of said toxicity representing genes comprises at least 50% of said toxicity representing genes; and
predicting toxicity of said agent based on a percentage of said toxicity representing genes that are significantly differentially expressed in said biological sample as induced by said agent.

16. The method according to claim 14, further comprising:
obtaining gene expression data defining differential gene expression of toxicity representing genes in a biological sample induced by said agent, wherein said toxicity representing genes comprise at least one gene regulated by each transcription factor selected from the group consisting of TP53, EP300, CDKN2A, PPARG, HIF1A, RELA, RB1, NR3C1, NFKBIA, ESR1, STAT5A, JUN, STAT3, SP1, SMARCA4, SMAD7, RARB, MYC, JUNB, EGR1, E2F1, CTNNB1, BRCA1, ATF2, RBL1, NFKB1, FOS, E2F3, CREBBO, SRF, NCOR2, HTT, ELK1, CYLD, and CREM; and
predicting toxicity of said agent based on a percentage of said toxicity representing genes that are significantly differentially expressed in said biological sample as induced by said agent.

17. The method according to claim 14, wherein predicting toxicity of said agent comprises predicting said agent to be toxic if at least 25% of said toxicity representing genes are significantly differentially expressed in said biological sample as induced by said agent.

18. The method according to claim 14, wherein obtaining said gene expression data comprises:
measuring gene expression of said toxicity representing genes in said biological sample induced by said agent; and
determining said gene expression data as differential expression values for said toxicity representing genes between said measured gene expression of said toxicity representing genes in said biological sample induced by said agent and control gene expression of said toxicity representing genes in said biological sample.

19. A computer program stored in non-transitory computer readable media and comprising instructions, which when executed by a processor, cause said processor to:
transform gene data defining, for each instance of a plurality of instances, differential gene expression of genes in a test biological sample induced by a test agent into gene set data defining, for each instance of said plurality of instances, an activation value for each gene set of a plurality of gene sets, wherein an instance defines a unique pair of a test agent and a test biological sample;
perform a probabilistic component modeling on said gene set data to define multiple components representing a respective specific compound-induced transcriptional response pattern active for a subset of test compounds and test cell lines, said multiple components encapsulating said genes of said plurality of gene sets;
determine, for a portion of said test agents, a concentration-dependent toxicity reflective of whether a concentration of a test agent applied to a test biological sample to induce a differential gene expression in said test biological sample is above, equal to or below a defined toxicity level; and
identify, based on said concentration-dependent toxicities, multiple prediction components as a subset of said multiple components, wherein the multiple prediction components are predictive of toxicity, wherein said PTGS score is defined as a proportion of differential gene expression, induced by an agent, that belongs to said multiple prediction components, and wherein said PTGS score is indicative of a toxicity prediction for the agent.

20. A computer program stored in non-transitory computer readable media and comprising instructions, which when executed by a processor, cause said processor to:

obtain gene expression data defining differential gene expression of genes in a biological sample induced by said agent; and calculate, based on said gene expression data, a predictive toxicogenomics space, PTGS, score indicative of a toxicity prediction for said agent, wherein said PTGS score represents a proportion of said differential gene expression in said biological sample, induced by said agent, that belongs to multiple prediction components identified by:

transforming gene data defining, for each instance of a plurality of instances, differential gene expression of genes in a test biological sample induced by a test agent into gene set data defining, for each instance of said plurality of instances, an activation value for each gene set of a plurality of gene sets, wherein an instance defines a unique pair of a test agent and a test biological sample;

performing a probabilistic component modeling on said gene set data to define multiple components representing a respective specific compound-induced transcriptional response pattern active for a subset of test compounds and test cell lines, said multiple components encapsulating said genes of said plurality of gene sets;

determining, for a portion of said test agents, a concentration-dependent toxicity reflective of whether a concentration of a test agent applied to a test biological sample to induce a differential expression of genes in said test biological sample is above, equal to or below a defined toxicity level; and identifying, based on said concentration-dependent toxicities, said multiple prediction components as a subset of said multiple components, wherein the multiple prediction components are predictive of toxicity.

* * * * *